(12) United States Patent
Gordon

(10) Patent No.: US 11,175,285 B2
(45) Date of Patent: *Nov. 16, 2021

(54) ULTRA-SENSITIVE BIOANALYTE QUANTIFICATION FROM SELF-ASSEMBLED QUADRUPLEX TAGS

(71) Applicant: Neil Gordon, Hampstead (CA)

(72) Inventor: Neil Gordon, Hampstead (CA)

( * ) Notice: Subject to any disclaimer, the term of this patent is extended or adjusted under 35 U.S.C. 154(b) by 391 days.

This patent is subject to a terminal disclaimer.

(21) Appl. No.: 15/783,197

(22) Filed: Oct. 13, 2017

(65) Prior Publication Data

US 2018/0106791 A1    Apr. 19, 2018

Related U.S. Application Data

(60) Provisional application No. 62/408,803, filed on Oct. 16, 2016.

(51) Int. Cl.
| | | |
|---|---|---|
| *G01N 33/53* | (2006.01) | |
| *C12Q 1/6825* | (2018.01) | |
| *C07H 21/00* | (2006.01) | |
| *C12Q 1/6876* | (2018.01) | |
| *G01N 33/543* | (2006.01) | |

(52) U.S. Cl.
CPC ......... *G01N 33/5308* (2013.01); *C07H 21/00* (2013.01); *C12Q 1/6825* (2013.01); *C12Q 1/6876* (2013.01); *G01N 33/54386* (2013.01); *C12Q 2525/204* (2013.01); *C12Q 2525/30* (2013.01); *C12Q 2545/114* (2013.01); *C12Q 2600/16* (2013.01)

(58) Field of Classification Search
CPC .................................. C12Q 1/68; C07H 21/00
See application file for complete search history.

(56) References Cited

U.S. PATENT DOCUMENTS

| | | | | | |
|---|---|---|---|---|---|
| 5,948,897 | A * | 9/1999 | Sen | ......................... | C12N 15/10 435/6.12 |
| 6,900,300 | B1 * | 5/2005 | Erikson | ................ | C12Q 1/6839 435/6.12 |
| 9,624,532 | B2 * | 4/2017 | Gordon | .................. | C12Q 1/682 |
| 2004/0018483 | A1 * | 1/2004 | Neidle | .................... | C07H 21/04 435/4 |
| 2004/0152116 | A1 * | 8/2004 | Davenport | ............. | C12N 15/11 435/6.18 |
| 2008/0153103 | A1 * | 6/2008 | Yam | ..................... | C07D 487/04 435/6.14 |
| 2009/0298703 | A1 * | 12/2009 | Gough | .................. | G06T 7/0012 506/8 |
| 2010/0173306 | A1 * | 7/2010 | Yaku | ........................ | C12Q 1/48 435/6.18 |
| 2013/0288380 | A1 * | 10/2013 | Miyoshi | ............... | C12Q 1/6809 436/94 |
| 2013/0295129 | A1 * | 11/2013 | Irvine | .................... | A61K 39/21 424/194.1 |
| 2014/0142147 | A1 * | 5/2014 | Henary | ................ | C07D 209/14 514/367 |
| 2015/0197804 | A1 * | 7/2015 | Willner | ................ | C12Q 1/6844 435/6.12 |
| 2016/0046932 | A1 * | 2/2016 | Phan | ..................... | C12N 15/113 435/6.11 |
| 2016/0194641 | A1 * | 7/2016 | Kumar | ................. | C12N 15/115 514/44 R |
| 2016/0310519 | A1 * | 10/2016 | Phan | ................... | A61K 31/7115 |
| 2018/0106791 | A1 * | 4/2018 | Gordon | ................. | C07H 21/00 |
| 2018/0275120 | A1 * | 9/2018 | Lee | ....................... | C12N 15/115 |
| 2019/0079084 | A1 * | 3/2019 | Gordon | ............... | C12Q 1/6844 435/6.12 |

FOREIGN PATENT DOCUMENTS

| | | | | | |
|---|---|---|---|---|---|
| WO | WO-2014175836 | A1 * | 10/2014 | ............. | C07H 21/00 |
| WO | WO-2014189468 | A1 * | 11/2014 | ............. | G01N 33/68 |

OTHER PUBLICATIONS

Bruskov et al., Heat-induced formation of reactive oxygen species and 8-oxoguanine, a biomarker of damage to DNA Nucleic Acids Research 30(6) : 1354 (Year: 2002).*
Choi et al., Label-free dual assay of DNA sequences and potassium ions using an aptamer probe and a molecular lightswitch complex. Chemical Communications 2009, 7419-7421 (Year: 2009).*
Ge et al., A Robust Electronic Switch Made of Immobilized Duplex/Quadruplex DNA. Agnew. Chem. Int. Ed.49: 9965 (Year: 2010).*
Chiorcea-Paquim et al.,Self-assembled G-quadruplex nanostructures: AFM and voltammetric characterization. Phys. Chem. Chem. Phys. 15 :9117-9124 (Year: 2013).*

(Continued)

*Primary Examiner* — Ethan C Whisenant

(57) ABSTRACT

This invention allows ultra-low levels of virtually any biological analyte to be detected and quantified rapidly, simply and inexpensively with an electrochemical biosensor using a novel electrochemically detectable tag that replaces optical labels. The tag binds to an analyte directly, or indirectly using one or more ligands and particles, and consists of a quadruplex electrochemically detectable oligonucleotide rich in guanine, or a single-stranded electrochemically detectable oligonucleotide rich in guanine that self-assembles into a quadruplex electrochemically detectable oligonucleotide when exposed to cations that enable quadruplex self-assembly. Quadruplex electrochemically detectable oligonucleotide tags are exposed, adsorbed or hybridized at the surface of a biosensor working electrode. An electrochemical technique facilitates the quadruplex tags to produce 8-oxoguanine oxidation signals proportional to the analyte level in the samples. The resulting analyte levels measured from 8-oxoguanine oxidation signals are 1,000 times lower than analyte levels measured from guanine oxidation signals.

19 Claims, 23 Drawing Sheets

(56) References Cited

OTHER PUBLICATIONS

Chiorcea-Paquim et al., Redox behaviour of G-quadruplexes. Electrochemica Acta 126 : 162-170 (Year: 2014).*
Chiorcea-Paquim et al.,Guanine Quadruplex Electrochemical Aptasensors. Chemosensors 4, 13 20 pgs. (Jul. 2016) (Year: 2016).*
Diculescu et al., Applications of a DNA-electrochemical biosensor. Trends in Analytical Chemistry 79 :23-36(May 2016) (Year: 2016).*
Doluca et al., Molecular Engineering of Guanine-Rich Sequences: Z-DNA, DNA Triplexes, and G-Quadruplexes. Chemical Reviews113 : 3044 (Year: 2013).*
Gray et al., Folding and Unfolding Pathways of the Human Telomeric G-Quadruplex. J. of Molecular Biology 426 : 1629 (Year: 2014).*
Guo et al., A G-quadruplex based label-free fluorescent biosensor for lead ion. Biosensors and Bioelectronics 35 :123-127 (Year: 2012).*
Hagihara et al.,Antisense-Induced Guanine Quadruplexes Inhibit Reverse Transcription by HIV-1 Reverse Transcriptase. JACS 132 : 11171 (Year: 2010).*
Hianik et al., Detection of aptamer-protein interactions using QCM and electrochemical indicator methods. Bioorganic & Medicinal Chemistry Letters 15 : 291 (Year: 2005).*
Jayamohan et al., Highly Sensitive Bacteria Quantification Using Immunomagnetic Separation and Electrochemical Detection of Guanine-Labeled Secondary Beads. Sensors 15:12034-12052 (Year: 2015).*
Labuda et al.,Electrochemical nucleic acid-based biosensors: Concepts, terms, and methodology (IUPAC Technical Report). Pure Applied Chemistry 82(5) : 1161-1187 (Year: 2010).*
Li et al., Carbon Nanotube Nanoelectrode Array for Ultrasensitive DNA Detection. Nano Letters 3(5) : 597 (Year: 2003).*
Long et al., Determination of 8-oxoguanine in human plasma and urine by high-performance liquid chromatography with electrochemical detection. J. of Chrom. B 731:241-249 (Year: 1999).*
Lu et al.,Structure and Stability of Sodium and Potassium Complexes of dT4G4 and dT4G4T. Biochemistry 31: 2455 (Year: 1992).*
Ohno et al., Quantitative Analysis of Oxidized Guanine, 8-Oxoguanine, in Mitochondrial DNA by Immunofluorescence Method. Ch. 13 in Mitochondrial DNA, Methods and Protocols 554 : 199 (Year: 2009).*
Pontinha et al., Quadruplex Nanostructures of d(TGGGGT): Influence of Sodium and Potassium Ions. Analytical Chemistry 86: 5851 (Year: 2014).*
Prat et al., Effect of Guanine Stacking on the Oxidation of 8-Oxoguanine in B-DNA. JACS 120 : 845-846 (Year: 1998).*
Sun et al., Porous platinum nanotubes labeled with hemin/G-quadruplex based electrochemical aptasensor for sensitive thrombin analysis via the cascade signal amplification. Biosensors and Bioelectronics 57 :16-21 (Year: 2014).*
Bourdoncle et al, JACS 128: 11094 (Year: 2006).*
Burge et al., Nucleic Acids Research 34(19) : 5402 (Year: 2006).*
Hagihara et al., JACS 132 : 11171 (Year: 2010).*

* cited by examiner

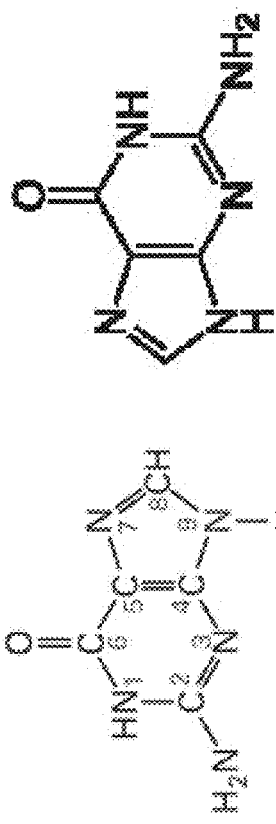
FIG. 2A
FIG. 2B
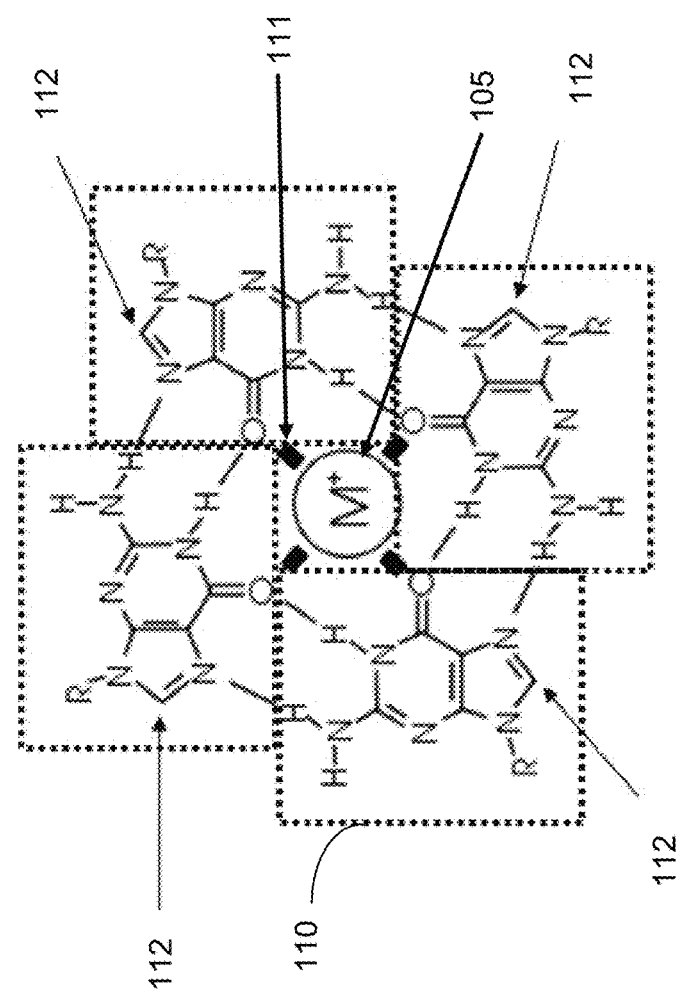
FIG. 2C
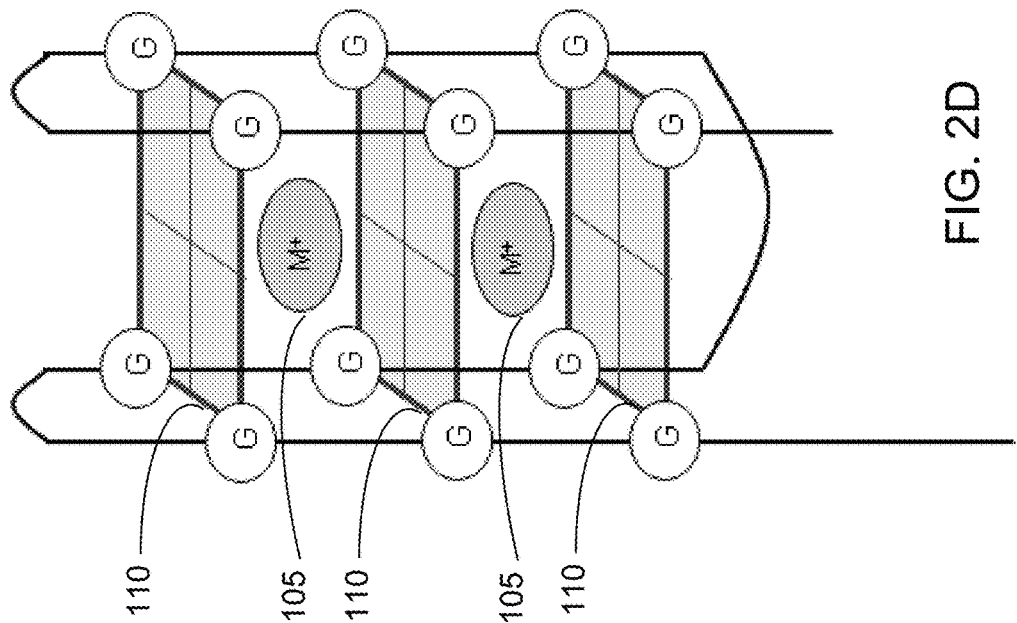
FIG. 2D

ULTRA-SENSITIVE BIOANALYTE QUANTIFICATION FROM SELF-ASSEMBLED QUADRUPLEX TAGS

CROSS-REFERENCE TO RELATED APPLICATIONS

This application claims benefit under 35 U.S.C. § 119(e) of U.S. provisional patent application Ser. No. 62/408,803 titled "ULTRA-SENSITIVE BIOANALYTE QUANTIFICATION FROM SELF-ASSEMBLED QUADRUPLEX TAGS", filed on Oct. 16, 2016, which, including all figures and tables, is incorporated herein by reference in its entirety.

FIELD OF THE INVENTION

The present invention relates generally to the field of biological assays. More particularly, the invention related to devices and methods that allow ultra-low levels of virtually any biological analyte to be detected and quantified rapidly, simply and inexpensively.

BACKGROUND OF THE INVENTION

The following discussion of the background of the invention is merely provided to aid the reader in understanding the invention and is not admitted to describe or constitute prior art to the present invention. All references, including publications, patent applications, and patents, cited herein are incorporated by reference in full to the same extent as if each individual publication was specifically and individually indicated to be incorporated by reference.

The analysis of biological analytes is critical for human health, safety and the environment. For example, infectious diseases can be diagnosed and treated by identifying the specific causes of the disease. This can be done by analyzing bodily samples using biological assays for the presence of disease-causing biological analytes including cells such as bacteria, protozoa and fungi, virus particles, toxins caused by the infectious materials, as well as biomolecular constituents of the infectious materials such as DNA, RNA and proteins. Diseases, cancers and medical conditions such as cardiac arrest can be identified by the presence and levels of protein antigens and antibodies produced by the human immune system or other bodily mechanism. Genetic markers can also be used to indicate an abnormal state or predisposition to diseases, cancers and medical conditions. Hazardous biological materials can also be transmitted by infected food, plants, water, air, objects such as surfaces or containers, insects, birds, fish, lizards, rodents, animals, and people. Samples can be analyzed for pathogenic cells, virus particles, protein toxins, and biomolecules such as nucleic acids and proteins. Some hazardous biological materials are naturally occurring while others can be intentionally released by bioterrorists. Many other applications and sectors such as biotechnology, pharmaceutical, and forensic also require analysis for the identification, presence and levels or concentrations of biological analytes.

Accurate, timely and practical analysis of biological analytes is extremely complex. Some analytes can be present as substances that are difficult and costly to accurately assay. Some analytes are not specific to a single disease, cancer, or medical condition, and some diseases, cancers and medical conditions are not specific to a single analyte or biomarker. Therefore identification of analytes can require multiplex assays for multiple analytes and in some cases multiple types of analytes for confirmation.

Some analytes can be present in extremely low levels and may not be detected by an assay, resulting in false negative outcomes. This requires highly sensitive assays and preferably the additional use of an amplification or enrichment process to increase the level of analytes before assaying. Some analytes can be surrounded by non-specific materials in several orders of magnitude greater levels, as well as non-specific materials comprising non-specific strains and species of the target analyte which are physically and chemically similar. Non-specific materials can prevent the analytes from being detected by an assay, and result in false negative outcomes. In the case where the analyte is not present in the sample, the non-specific material may be incorrectly detected by the assay, causing a false positive outcome. This requires highly specific assays and preferably the additional use of a purification process to remove non-specific materials before assaying. Even though some analytes may be present in a sample and correctly detected by the assay, some analytes can have an abnormal or harmful level which is higher or lower than a normal level. Some analytes have levels that change over time. This requires assays that can quantify analyte levels or concentrations, accurately and frequently.

Some analytes are highly infectious, extremely harmful, and costly to treat or remediate. These analytes need to be analyzed in a very timely manner to minimize the transmission of the infection. As well, some analytes have an elevated level for a limited period of time. Some assay operators have limited technical proficiency and need assays that are automated and easy to use. Some testing organizations have budgetary constraints and require assays to be low cost for consumables, labor, sample collection, assay equipment and laboratory facilities.

Numerous assays are known for detecting biological analytes in a sample. Four general types of biological analytes are cells, nucleic acids, proteins and redox active species. The technologies and assays directed at detecting these analytes are basically separate and independent. In certain cases different technologies can be used to measure the presence of analytes associated with the same disease. As an example, Table 1 illustrates the relative limits of detection and turnaround times for selected commercial products that use cell cultures, nucleic acid amplification tests and protein immunoassays for detecting analytes associated with certain infectious diseases. Cell cultures and nucleic acid amplification tests have the lowest limits of detection but also have longer turnaround times because of the test complexity, labor-intensity, and laboratory logistics. Protein immunoassays can be done in laboratories, and are also available as simple rapid point-of-care tests that have a higher limit of detection.

TABLE 1

Relative Limits of Detection and Turnaround Times of Different Detection Technologies Used by Commercial Products

| Analyte | Cell Culture | Nucleic Acid Amplification Test | Protein Immunoassay (Lab Test) | Protein Immunoassay (POC Test) |
|---|---|---|---|---|
| | | Limit of Detection | | |
| C. difficile Toxin Protein | 1 pg/mL | 10 pg/mL | 300 pg/mL | 1000 pg/mL |
| Campylobacter C. jejuni Bacteria | $3 \times 10^2$ cfu/mL | $3 \times 10^3$ cfu/mL | $3 \times 10^6$ cfu/mL | $3 \times 10^7$ cfu/mL |

TABLE 1-continued

Relative Limits of Detection and Turnaround Times of
Different Detection Technologies Used by Commercial Products

| Analyte | Cell Culture | Nucleic Acid Amplification Test | Protein Immunoassay (Lab Test) | Protein Immunoassay (POC Test) |
|---|---|---|---|---|
| HIV Virus | Not applicable to viruses | ~15 virions/mL | ~3000 virions/mL | >>3000 virions/mL |
| Turnaround Time | | | | |
| Time between sample and test result | 1-7 days | 1-2 days | 1-2 days | 5-60 min |

Cell assays employ viable cells to reproduce outside of their natural environment to amplify the detection signals. Targets cells reproduce in a growth media incubated at an appropriate temperature, gas mixture and pH. Materials can be included to suppress the growth of non-specific cells. Detectable dyes provide color which intensifies with an increasing number of cells. Cell cultures are sensitive assays, but have a slow turnaround time (2-7 days) for producing a detectable number of cell colonies, and can result in false positive results caused by non-specific strains of the target cells that reproduce in the growth media. Cell assays can fail if target cells are unable to reproduce due to cells being dead or injured, or from contamination of the growth media. Because of the labor-intensive processing, cell assays can also fail from technician error due to an incorrect manual process, or from an inability to distinguish target cells from non-specific materials.

Nucleic acid assays cause a target region of DNA strands to amplify using polymerase chain reaction (PCR) during repeated thermally-induced biochemical processes. DNA fragments are exposed to appropriate denaturing conditions including high temperature to melt double helix DNA into single DNA strands. The temperature is lowered and target regions of the single stands act as templates which anneal with complementary nucleotide primers. The temperature is raised to an activity temperature where a polymerase enzyme causes a chemical reaction to synthesize new single DNA strands complementary to the single strand DNA templates, which form double helix DNA. The process is repeated until a sufficient number of copies are produced. Fluorescent dyes or fluorophore-containing DNA probes create a detectable signal which intensifies with an increasing number of target DNA fragments. Nucleic acid assays are highly specific and increase in sensitivity when more detectable target DNA fragments are produced. Because of the complex processes for sample preparation, amplification, detection and quantification, nucleic acid assays require highly skilled operators using costly equipment and expensive laboratory facilities. This limits the number of organizations that can conduct nucleic acid assays. Bottlenecks can occur at test labs and cause delays in testing, treatment and remediation. Nucleic acid assays can fail when non-specific DNA products amplify due to contamination or improper sample processing in advance of PCR. Failure can also occur if detectable fluorescent dyes or fluorophores are not adequately delivered along with the replicated target DNA fragments.

Protein assays identify and quantify proteins such as hormones and enzymes, by acting as antigens or antibodies in a chemical reaction. One of the most common protein assays is enzyme-linked immunosorbent assay (ELISA). In a direct ELISA an antigen analyte is adsorbed to a plate and a blocking agent is added to block potential binding sites from non-specific materials. An antibody-enzyme complex is added to bind with the antigen analyte and the plate is washed to remove unbound antibody-enzyme complexes. An appropriate enzyme substrate is added to produce an optical signal proportional to the amount of antigen analyte in the sample. In a Sandwich ELISA, a matched pair of antibodies forms a sandwich structure containing a first outer antibody layer to capture the analyte, an internal layer comprising the antigen analyte and a second outer antibody layer to detect the analyte. The capture antibody is initially bound to the plate and then binds with the antigen analyte contained in a test sample. After washing, a detection antibody-enzyme complex is added to bind with the antigen analyte and the plate is washed to remove unbound capture antibody-enzyme complexes. An appropriate enzyme substrate is added to produce an optical signal proportional to the amount of antigen analyte in the sample. Direct ELISA is faster because only one antibody is being used and fewer steps are required. Sandwich ELISA can have a lower detection limit because each capture antibody can contain several epitopes that can be bound by detection antibodies. Sandwich ELISA can also be made more sensitive using avidin-biotin complexes which have several sites for enzymes to provide multiple enzymes per analyte. This can amplify the detection signal by ten to a few hundred times. In contrast, cell cultures and PCR can produce millions or more copies. Protein assays are relatively easy to use, rapid and low cost. A major disadvantage is the inability to significantly amplify protein signals, making it necessary for the subject or its immune system to produce a detectable level of target protein analytes. This waiting period can delay detection and subsequent treatment by weeks or months. If the protein analytes are assayed using immunoassay before a detectable level is secreted, then a false negative detection outcomes will be produced causing the disease to be undetected. Another problem is the specificity of antibodies and antigens. Many antibodies, and particularly polyclonal, can detect a wide range of species; however these can include non-specific strains that produce false positive detection outcomes. The use of highly specific monoclonal antibodies greatly improves the specificity.

All of the abovementioned assays suffer from limitations. None of these assays can identify all types of analytes. Unlike cell and nucleic acid assays, protein assays cannot support significant signal amplification which can limit the sensitivity of protein assays. Amplification used in nucleic acid amplification tests and cell cultures adds time, cost and complexity. Cell and protein assays can have insufficient specificity and can benefit from purification steps such as magnetic separation. This adds to the assay cost and complexity. Quantification can be difficult if done manually or expensive if a transduction system is needed to convert optical signals to electrical signals. Nucleic acid amplification assays are sensitive and specific, however the complex processes used for sample preparation, amplification, detection and quantification require highly skilled operators, costly equipment, expensive laboratory facilities, and time-consuming laboratory logistics. This complexity limits the number of organizations that can conduct nucleic acid assays.

Another general type of biological assay is for redox species and works when a redox analyte electrochemically reduces and/or oxidizes at an electrode. A redox analyte is placed in close proximity to a set of electrodes and undergoes electrical stimulation such as applying a potential. This causes the analyte to lose electrons through oxidation or gain electrons through reduction, which can be measured as an electrical signal at the working electrode. The amount of analyte oxidized or reduced and the corresponding electrical signal reflect the quantity of analyte in the sample. Other materials may be also be present such as a mediator to transport redox electrons, and non-specific materials, both of which can cause electrical noise that interferes with the electrical signal from the analyte. When redox analytes are present in high levels, such as approximately $10^{14}$ glucose molecules in blood associated with 1.1 mmol/L (or mM), redox signals are relatively high compared with background noise and can be directly measured to provide rapid quantification with acceptable sensitivity and specificity. Since the detection signal is electrical, no expensive transduction system is needed to convert optical signals. This allows glucose meters using redox assays to be performed in rapid, easy to use, low cost instruments.

Other redox analytes can be present in very low levels such as approximately $10^4$ to $10^6$ guanine molecules associated with 5,000 copies/mL of HIV RNA in blood as required for clinical use. Low levels of guanine bases in nucleic acids such as RNA and DNA can be oxidized to generate very electrical signals. Direct electrochemical DNA sensing approaches are inherently not highly sensitive. This is because of the low signal-to-noise ratio and significant background current from the high potentials required for the direct reduction or oxidation of electroactive nucleotides such as guanine and adenine.

TABLE 2

Examples of Redox Analytes

| Redox Analyte | Sample | Level Required for Clinical Use | Redox Analytes vailable for Electrochemical Quantification |
|---|---|---|---|
| Glucose | 1 µL whole blood | 1.1 mM glucose (20 mg/dL) | ~$10^{14}$ glucose molecules |
| HIV | 100 µL whole blood | 5,000 RNA copies/mL | ~$10^4$-$10^6$ guanine molecules |

Various approaches have been employed to detect and/or quantify nucleic acid analytes using redox assays by improving the signal-to-noise resolution. One approach reduces the active surface area of a biosensor working electrode by replacing a conventional solid working electrode with a nanobiosensor comprising randomly distributed forests of nanoscale structures on the electrode surface (Thorpe, et al, Lieber, et al). Thorpe further applied a redox-active mediator tris(2,2'-bipyridine)ruthenium(II) $Ru(bpy)_3^{2+}$ to bring the electrons from DNA (mainly guanine residues for oxidation) to the electrode surface. Under the applied potential, $Ru(bpy)_3^{2+}$ is first oxidized to $Ru(bpy)_3^{3+}$ on an electrode. The guanine residues of the DNA then reduce $Ru(bpy)_3^{3+}$ to regenerate $Ru(bpy)_3^{2+}$, thus forming a catalytic cycle.

Another nanobiosensor approach replaces the randomly distributed forests of nanoscale structures with ordered arrays of nanoscale structures spaced at least 1 µm apart to further reduce the surface area of a working electrode (Gordon, et al). These approaches allowed the guanine signal to be better distinguished from noise over conventional solid working electrodes but not to the degree required for direct measurement of the low level of redox species associated with target bio-analytes such as guanine molecules. Fabrication of nanoscale structures, such as 100 nm diameter carbon nanotubes, provides additional complexity over microscale structures that result in the need for specialized production equipment with high cost and limited throughput, poor production yields, and high unit costs for nanobiosensors.

Another approach employs PCR to amplify target DNA before detection by a conventional biosensor (Ozkan, et al). The use of PCR provides added complexity, time and cost which negates the benefits experienced from the glucose redox assay. Another approach employs magnetic separation to purify analytes by removing background interferences before detection by a conventional biosensor. Palesecek et al, and Wang and Kawde capture target sequences using probe DNA immobilized onto magnetic particles. After target hybridization, the particles are magnetically separated from the pool of analytes. The collected DNA is denatured in acidic solutions, and the free guanine and adenine nucleotides are collected and analyzed using anodic stripping voltammetry. Although the noise from other interferents can be reduced, the inherent background signal from water electrolysis always presents. As a result, the guanine oxidation signal is too low for direct measurement in the presence of such large background currents.

The above approaches targeted specific biological analytes and requires a unique ligand and corresponding recognition probe on the biosensor which greatly increased the development cost and reagent cost for assays. Gordon overcame this limitation by employing a generic oligonucleotide tag rich in electroactive guanine and temporarily bound millions of the oligonucleotide tags to a microparticle in a sandwich assay with an analyte and magnetic particle. Eluted tags were measured with a generic biosensor employing a Ruthenium Bipyridine electron transport mediator. The microparticle provided a larger surface than a nanoparticle and users could configure their desired sensitivity with a larger particle size to increase the number of guanine tags per analyte. However the method still suffered from the significant background current from the high potentials required for the direct oxidation of guanine.

There is a need for a simple assay that can determine the presence and quantity of very low level analytes including multiple analytes and multiple types of analytes in the same sample, provide high sensitivity preferably without the time and cost of signal amplification, provide high specificity preferably with purification, and provide the above in a rapid, easy to use and low cost device, including the capability for point-of-care use.

SUMMARY OF THE INVENTION

In accordance with a first aspect of the present invention, there is provided an electrochemically detectable oligonucleotide tag for detecting and/or quantifying the level of one or more target analytes in a fluid sample, wherein the tag consists of a single-stranded electrochemically detectable oligonucleotide that temporarily binds to an analyte directly, or indirectly using one or more ligands and particles, then self-assembles into a quadruplex electrochemically detectable oligonucleotide when exposed to cations that enable quadruplex self-assembly. The majority of the nucleotides within said single-stranded electrochemically detectable oligonucleotide tags are guanine with at least 4 guanines in a consecutive sequence. Sets of 4 guanine self-assemble into square planar tetrad structures bound by eight Hoogsteen hydrogen bonds, wherein two or more square planar tetrad structures are stacked on top of each other and stabilized by pi-pi hydrophobic interactions, wherein between each square planar tetrad structure in the stack is a monovalent cation which is coordinated to the lone pairs of electrons of O6 in each guanine. The quadruplex electrochemically detectable oligonucleotides are exposed, adsorbed or hybridized to a biosensor working electrode surface wherein a redox detection technique oxidizes guanine and produces 8-oxoguanine signals. In addition the majority of the nucleotides within said single-stranded oligonucleotide detection tags are guanine, and when used for detecting and/or quantifying multiple analytes simultaneously from the same sample, the nucleotides within the single-stranded oligonucleotide detection tags are selected from the group consisting of guanine, adenine, thymine, and cytosine, and wherein the combination of said nucleotides produces a unique oligonucleotide tag that is used to detect and/or quantify a specific analyte or group of specific analytes.

In accordance with another aspect of the invention, there is also provided a method for detecting and/or quantifying the level of one or more target analytes in a fluid sample wherein said method consists of the following steps performed sequentially: (a) providing a fluid sample that may contain non-specific materials and one or more analytes; (b) providing one or more sets of a plurality of single-stranded electrochemically detectable oligonucleotide tags that temporarily bind to an analyte directly, or indirectly using one or more ligands and particles; (c) unbinding the single-stranded electrochemically detectable oligonucleotide tags from the analytes with one or more of chemicals, heat and mechanical processes; (d) exposing the single-stranded electrochemically detectable oligonucleotide tags to monovalent cations that enable the single-stranded electrochemically detectable oligonucleotide tags to self assemble into quadruplex electrochemically detectable oligonucleotide tags; and (e) providing one or more working electrodes and adsorbing or hybridizing quadruplex tags to the biosensor working electrodes, wherein each working electrode is associated with a specific analyte or group of specific analytes that may be present in the sample, and an electrochemical detection technique that produces electrochemical signals on each working electrode in proportion to the level of an associated analyte or group of analytes if said analyte or group of analytes is present in the fluid sample based on the electrochemical signal produced by the associated quadruplex electrochemically detectable oligonucleotide tags. The method employs one or more electrochemically detectable oligonucleotide tags for detecting and/or quantifying the level of one or more target analytes in a fluid sample, wherein the tags consists of a single-stranded electrochemically detectable oligonucleotide that temporarily binds to an analyte directly, or indirectly using one or more ligands and particles, then self-assemble into a quadruplex electrochemically detectable oligonucleotide when exposed to cations that enable quadruplex self-assembly. The majority of the nucleotides within said single-stranded electrochemically detectable oligonucleotide tags are guanine with at least 4 guanines in a consecutive sequence. Sets of 4 guanine self-assemble into square planar tetrad structures bound by eight Hoogsteen hydrogen bonds, wherein two or more square planar tetrad structures are stacked on top of each other and stabilized by pi-pi hydrophobic interactions, wherein between each square planar tetrad structure in the stack is a monovalent cation which is coordinated to the lone pairs of electrons of O6 in each guanine. The quadruplex electrochemically detectable oligonucleotides are exposed, adsorbed or hybridized to a biosensor working electrode surface wherein a redox detection technique oxidizes guanine and produces 8-oxoguanine signals. In addition the majority of the nucleotides within said single-stranded oligonucleotide detection tags are guanine, and when used for detecting and/or quantifying multiple analytes simultaneously from the same sample, the nucleotides within the single-stranded oligonucleotide detection tags are selected from the group consisting of guanine, adenine, thymine, and cytosine, and wherein the combination of said nucleotides produces a unique oligonucleotide tag that is used to detect and/or quantify a specific analyte or group of specific analytes.

In accordance with another aspect of the invention, there is also provided a device for detecting and/or quantifying the level of one or more target analytes in a fluid sample, wherein said device consists of: (a) a tag attachment unit configured to bind one or more single-stranded electrochemically detectable oligonucleotide tags directly to an analyte, or indirectly to an analyte using a ligand, or indirectly to an analyte using a particle, if said analyte is present in a fluid sample, (b) a tag discharge unit configured to unbind single-stranded electrochemically detectable oligonucleotide tags from the analytes, (c) a tag self-assembly unit configured to enable single-stranded electrochemically detectable oligonucleotide tags to self-assemble into quadruplex electrochemically detectable oligonucleotide by providing monovalent cations that enable quadruplex formation, and (d) an electrochemical detection unit with at least one biosensor working electrode configured to measure detection signals from the quadruplex electrochemically detectable oligonucleotide tags. The device employs one or more electrochemically detectable oligonucleotide tags for detecting and/or quantifying the level of one or more target analytes in a fluid sample, wherein the tags consists of a single-stranded electrochemically detectable oligonucleotide that temporarily binds to an analyte directly, or indirectly using one or more ligands and particles, then self-assemble into a quadruplex electrochemically detectable oligonucleotide when exposed to cations that enable quadruplex self-assembly. The majority of the nucleotides within said single-stranded electrochemically detectable oligonucleotide tags are guanine with at least 4 guanines in a consecutive sequence. Sets of 4 guanine self-assemble into square planar tetrad structures bound by eight Hoogsteen hydrogen bonds, wherein two or more square planar tetrad structures are stacked on top of each other and stabilized by pi-pi hydrophobic interactions, wherein between each square planar tetrad structure in the stack is a monovalent cation which is coordinated to the lone pairs of electrons of O6 in each guanine. The quadruplex electrochemically detectable oligonucleotides are exposed, adsorbed or hybridized to a biosensor working electrode surface wherein a redox detection technique oxidizes guanine and produces 8-oxoguanine signals. In addition the majority of the nucleotides within said single-stranded oligonucleotide detection tags are guanine, and when used for detecting and/or quantifying multiple analytes simultaneously from the same sample, the nucleotides within the single-stranded oligonucleotide detection tags are selected from the group consisting of guanine, adenine, thymine, and cytosine, and wherein the combination of said nucleotides produces a unique oligonucleotide tag that is used to detect and/or quantify a specific analyte or group of specific analytes.

Other features and advantages of the present invention will be better understood upon reading of preferred embodiments thereof with reference to the appended drawings.

BRIEF DESCRIPTION OF THE DRAWINGS

FIGS. 2A and 2B provide the chemical structure of guanine with and without symbols for carbon (C).

FIG. 2C is a schematic representation of a set of 4 guanine self-assembled into square planar tetrad structures.

FIG. 2D is a schematic representation of a three square planar tetrad structures stacked on top of each other with a monovalent cation in between each tetrad.

DETAILED DESCRIPTION OF THE PREFERRED EMBODIMENTS

Figure 1A:
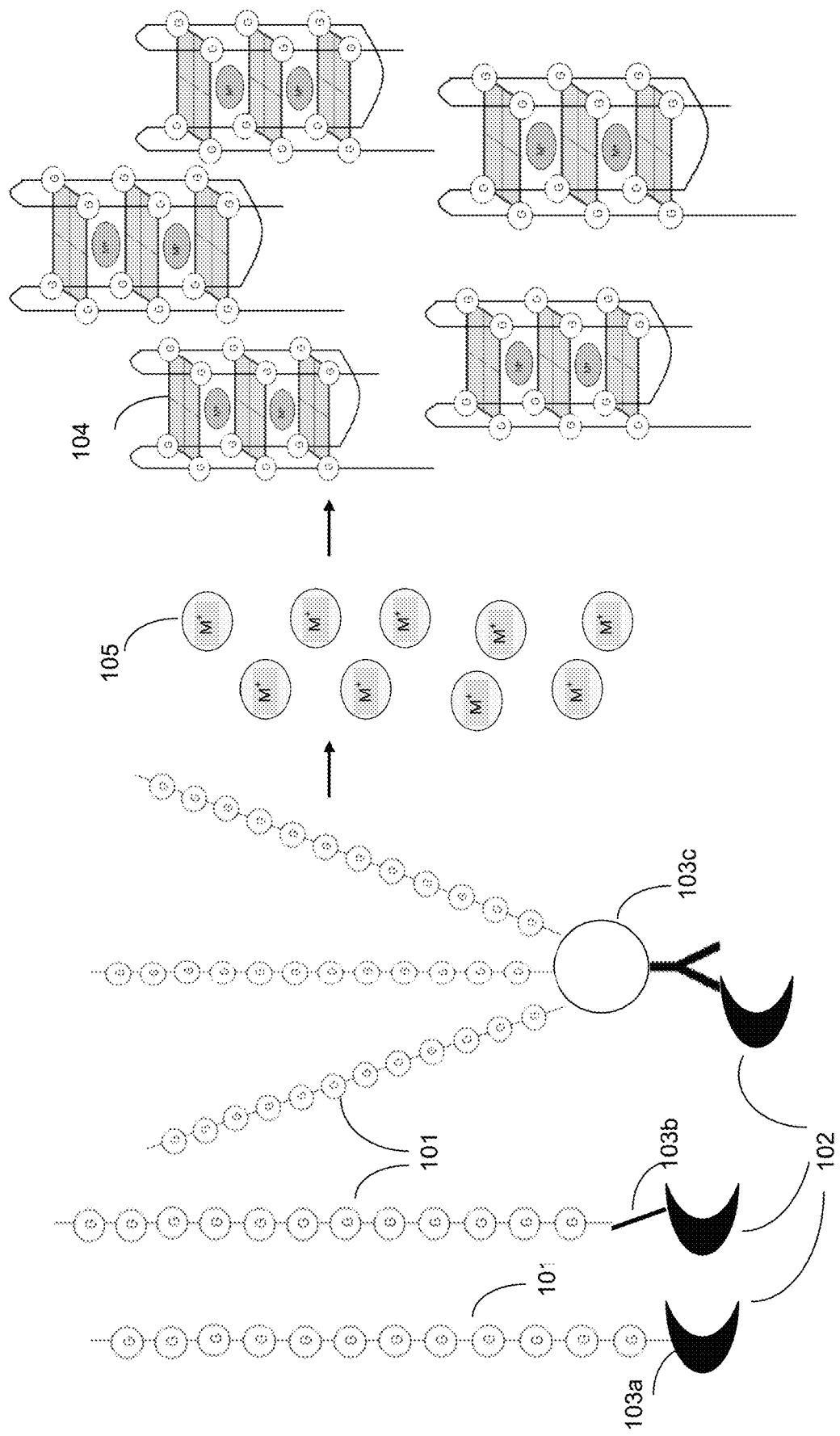
FIG. 1A is a schematic representation of single-stranded electrochemically detectable oligonucleotide tags binding to analytes directly or indirectly using a ligand or particle that self-assemble into quadruplex electrochemically detectable oligonucleotide tags when exposed to cations that enable quadruplex self-assembly.

In this specification, although the preferred embodiments have been described in detail, it should be understood that various changes, substitutions and alterations may be made therein without departing from the spirit and scope of the instant invention. Therefore, the specification is to be regarded in an illustrative rather than a restrictive sense.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

In order to facilitate review of the various examples of this disclosure, the following explanations of specific terms are provided: "Amplification ratio"—The ratio of guanine molecules per target analyte to be detected and/or quantified, where the guanine molecules are provided as bases in electrochemically detectable tags. "Analyte"—A substance of interest being analyzed in an analytic procedure. "Analyte Binding Material"—A natural or synthetic material that can bind with an analyte such as an antibody with an antigen analyte or an oligonucleotide with a nucleic acid analyte. "Biosensor"—An analytical device for detecting a biological analyte using a biological receptor that recognizes the analyte, and a transducer that converts the recognition event into a measurable signal. An example of a recognition event is hybridization. "Electrochemical biosensor"—A biosensor that employs an electrochemical transducer. "Electrochemical detection"—A series of techniques for determining the presence and/or level of a redox species by measuring the electrical signal in a solution between a working electrode and a counter electrode due to the loss or gain of electrons in a redox reaction, and where the reaction is caused by electrical stimulation such as applying an electrical potential. "Electrochemically detectable tag"—A tag used for electrochemical detection comprising at least one redox species such as guanine, and where a tag can be an oligonucleotide. "Electron transport mediator"—A material or molecule that shuttles electrons between biological receptors and working electrodes. "Guanine"—One of the four main nucleobases found in the nucleic acids DNA and RNA and forms a base pair with cytosine. Guanine is a redox species and is the most easily oxidized nucleobase. "Guanine-Quadruplex"—a tertiary structure formed in nucleic acids or oligonucleotides by sequences that are rich in guanine where four guanine bases can associate through Hoogsteen hydrogen bonding to form a square planar structure tetrad, and two or more guanine tetrads can stack on top of each other and stabilized by the presence of a cation between each pair of tetrads. "Oligonucleotide"—A short single-stranded nucleic acid chain that is synthetically produced with a sequence of bases complimentary to a specific biological target. "Recognition probe"—A probe that can act as a biological receptor in a biosensor. In the case of an electrochemical biosensor, the recognition probe typically comprises cytosine which can hybridize with redox active guanine tags. "Redox reaction"—A class of electrode reactions involving oxidation/reduction of two dissolved redox species. "Redox species"—A species of an element which can occur in more than one oxidation state in natural aqueous environments such as glucose, guanine and ruthenium bipyridine. "Signal-to-Noise Ratio"—The ratio of the level of a desired detection signal to the level of background noise.

The present invention generally provides electrochemically detectable tags, methods, and devices and for detecting and/or quantifying extremely low levels of one or more target analytes in a fluid sample. Electrochemical detection is among the easiest, most rapid and least costly biodetection technique on the market and is the gold standard for quantifying glucose, metabolites, electrolytes, and blood gases. However, its applications are limited to the subset of analytes that have redox properties and also are present in concentrations that are high enough to be detected by an electrochemical biosensor.

This invention allows ultra-low levels of virtually any biological analyte to be detected and quantified rapidly, simply and inexpensively with an electrochemical biosensor using a novel electrochemical detection tag that replaces insensitive optical labels. The tag is a guanine-rich oligonucleotide comprising at least 4 consecutive guanines. The tag binds to an analyte as a "single-stranded" electrochemically detectable oligonucleotide tag to "capture" analytes and then the self-assembles into a "quadruplex" electrochemically detectable oligonucleotide tag in the presence of monovalent cations, such as Na+ or K+ for "detection" of the analyte.

The advantages of a singled-stranded electrochemically detectable oligonucleotide tag for capture and a quadruplex electrochemically detectable oligonucleotide tag for detection are numerous. An innovative aspect of this invention is that the singled-stranded electrochemically detectable oligonucleotide tag takes advantage of its small footprint to amplify the number of tags per analyte by binding a plurality of tags to an analyte directly, or indirectly using one or more ligands and particles. The quadruplex tag offers much greater detection sensitivity by oxidizing guanine and producing 8-oxoguanine signals at a lower potential than guanine oxidation thus providing a lower background signal and greatly increased signal-to-noise resolution.

Singled-Stranded Electrochemically Detectable Oligonucleotide Tag

The singled-stranded electrochemically detectable oligonucleotide tag used in this invention is generic and can bind with virtually any analyte using an appropriate ligand. Its small footprint allows a plurality of singled-stranded electrochemically detectable oligonucleotide tags to bind with a single analyte directly or indirectly with a ligand or with a ligand and a particle. The particle can be a nanoparticle or a microparticle with a larger particle having a greater surface area or internal volume to hold a greater number of singled-stranded electrochemically detectable oligonucleotide tags. The single-stranded oligonucleotide tags can also be increased in length to provide more electroactive guanines per analyte. Larger particles and longer oligonucleotides can greatly increase sensitivity. The single-stranded oligonucleotide tags can also be used for multiplex testing of many analytes in the same sample by creating a unique nucleotide sequence for each analyte from guanine and other nucleotides including adenine, thymine, and cytosine.

Quadruplex Electrochemically Detectable Oligonucleotide Tag

The quadruplex electrochemically detectable oligonucleotide tag provides vastly improved detection sensitivity over singled-stranded electrochemically detectable oligonucleotide tags. The quadruplex structure brings guanine molecules closer to the biosensor working electrode to increase the detection signal. This eliminates the need for an electron transport mediator such as Ruthenium Bipyridine to transport guanine oxidation electrons to the electrode surface. Guanine oxidizes at high potentials which also produce significant background current. When a fast voltammetry scan is used such as square wave voltammetry at 1400 mV/s, the quadruplex electrochemically detectable oligonucleotide tag rich in guanine produces an electrochemical signal from 8-oxoguanine oxidation which was not measurable from the single-stranded electrochemically detectable oligonucleotide tag rich in guanine. 8-oxoguanine produces a signal at a lower potential than guanine oxidation, and as a consequence, there is a lower background signal from the solution. This greatly increases signal-to-noise resolution at lower concentrations of tags to provide 3 or more logs lower limit of detection. Another benefit is that 8-oxoguanine is reversible and can oxidize and reduce, to allow an associated biosensor to be used multiple times. Guanine oxidizes but does not reduce, which limits the use of single-stranded electrochemically detectable oligonucleotide tags rich in guanine.

Guanine quadruplex structures are formed by repeated folding of either the single polynucleotide molecule or by association of two or four molecules. The structure consists of stacked guanine tetrads, which are square co-planar arrays of four guanine bases. Guanine quadruplexes are stabilized with 8 Hoogsteen hydrogen bonding between the four guanines within each tetrad. The guanine quartets are stack on top of each other in a helical fashion and are stabilized by pi-pi hydrophobic interactions and by the presence of monovalent cations such as K+ and Na+. The cations are placed in the central helical cavity, in between the guanine quadruplex tetrads, and establish interactions with the carbonyl oxygen from the guanine bases.

Guanine quadruplex structures are used in structural biology, medicinal chemistry, supra-molecular chemistry, nanotechnology, and biosensor technology. They have emerged as a new class of cancer-specific molecular targets for anticancer drugs, since the quadruplex stabilization by small organic molecules can lead to telomerase inhibition and telomere dysfunction in cancer cells. In biosensing, guanine quadruplexes have been used as analytes indicating an oxidative injury to DNA caused by a mutagenic transversion of G to T and observed in cellular malfunction leading to a state of illness, tumor cells, and cancer tissues. (Oliveira Brett, et al).

Guanine quadruplex structures have also been used in DNA electrochemical biosensors with guanine quadruplex structures immobilized on the working electrode surface as recognition probe for detecting analytes. Chiorcea-Paquim et al. classify DNA electrochemical biosensors into two groups as electrochemical aptasensors and as the hemin/DNAzyme electrochemical biosensors. In both groups the guanine quadruplexes are pre-fabricated onto the biosensors before the analytes are delivered. Unlike this invention, none of these technologies involve single-stranded electrochemically detectable oligonucleotide tags to capture analytes then the self-assemble into quadruplex electrochemically detectable oligonucleotide tags to indicate the presence and/or quantify of the analytes temporarily bound to the tags.

Chen describes guanine quadruplex structures to be uniquely determined by the primary nucleotide sequences, in a manner analogous to protein folding being determined by a primary amino acid sequence. In addition, a certain guanine-rich sequence may adopt different guanine-quadruplex structures in the presence of different cations, as in the case of the human telomeric DNA, and a sequence may fold into more than one conformation. Chen cites as examples that the human telomeric DNA sequence was first found to form a basket-type guanine-quadruplex conformation in Na+ solution, a parallel-stranded guanine-quadruplex conformation in the presence of K+ in the crystalline state, and hybrid-type guanine-quadruplexes in K+ solution.

An advantage of this invention is that the single-stranded electrochemically detectable oligonucleotide tags are synthetic and have a wider range of possible quadruplex structures than can be formed compared to naturally occurring human telomeric DNA. The quadruplex electrochemically detectable oligonucleotide tag can change in shape, structure, and performance by modifying one or more of the number of guanines, the number of nucleotides, the sequence of nucleotides, the cation molecule, the cation concentration, the temperature during self-assembly, the pH during self-assembly, the presence of chemicals during self-assembly, and the use of mechanical agitation.

Unique quadruplex structures, self-assembly conditions and mix of reagents can be selected to produce tags that are more advantageous for biodetection, and potentially create other related applications. For example, the biodetection device can be integrated with an associated instrument for the automated delivery of drugs or chemicals and said device measures an analyte's presence and/or quantity which triggers the release of drugs or chemicals.

As another example, most quadruplex applications involve guanine and 8-oxoguanine. However, another advantage of the invention is that it is not limited to guanine nucleotides that self-assemble into guanine quadruplexes along with 8-oxoguaine oxidation signals. In another embodiment the majority of the nucleotides within the single-stranded electrochemically detectable oligonucleotide tags are adenine with at least 4 adenine in a consecutive sequence and the quadruplex electrochemically detectable oligonucleotides are exposed, adsorbed or hybridized to a biosensor working electrode surface wherein a redox detection technique oxidizes adenine and produces 8-oxoadenine signals. In another embodiment the majority of the nucleotides within the single-stranded electrochemically detectable oligonucleotide tags are thymine with at least 4 thymine in a consecutive sequence and the quadruplex electrochemically detectable oligonucleotides are exposed, adsorbed or hybridized to a biosensor working electrode surface wherein a redox detection technique oxidizes thymine and produces 8-oxothymine signals. In another embodiment the majority of the nucleotides within the single-stranded electrochemically detectable oligonucleotide tags are cytosine with at least 4 cytosine in a consecutive sequence and the quadruplex electrochemically detectable oligonucleotides are exposed, adsorbed or hybridized to a biosensor working electrode surface wherein a redox detection technique oxidizes cytosine and produces 8-oxocytosine signals. In another embodiment multiple quadruplex tetrads can be formed from one or more different nucleotides and produce oxo derivative signals from the oxidation of one or more different oxo derivative. In each embodiment, the majority nucleotide forms a square planar tetrad.

This invention also provides methods and devices for detecting and/or quantifying ultra-low levels of virtually any biological analyte in a fluid sample. The methods and devices employ the self-assembling electrochemically detectable oligonucleotide tags to provide extreme sensitivity using a rapid, simple and inexpensive electrochemical biosensor. In one embodiment, the method works like an sandwich ELISA assay and the optical tags and optical reader are replaced with a plurality of the invention's electrochemically detectable tags and an electrochemically reader known as a potentiostat. In one embodiment of the invention, a 100 µL fluid sample that may contain an analyte is added to a microtiter well which is pre-coated with a plurality of a capture antibody that binds with the analyte if it is present. A blocking agent is also used to prevent the binding of non-specific materials that may be in the fluid sample. The sample is incubated for 30 minutes and then a plurality of a detection antibody is added which is also bond to single-stranded electrochemically detectable oligonucleotide tags rich in guanine, such as a 20-mer PolyG oligonucleotide. In one embodiment the detection antibody is bound to a single tag. In another embodiment, the detection antibody is bound to a nanoparticle which is also bound to about 1,000 tags. In yet another embodiment the detection antibody is bound to a microparticle which is also bound to about 1,000,000 tags. These embodiments illustrate the configurability of the use to increase the number of tags per analyte and as a consequence increase the assay's sensitivity since fewer analytes can be detected when they are attached to a greater number of tags. One or more washes can also be used.

The method allows the tags to incubate for 30 minutes then elutes the single-stranded electrochemically detectable oligonucleotide tags with an elution buffer such as 80 mM NaOAc (pH 9) and 95% formamide that contains Na+ cations. This facilitates the self-assembly of the single-stranded electrochemically detectable oligonucleotide tags to quadruplex electrochemically detectable oligonucleotide tags. The elution step is typically conducted at 90° C. to denature the oligonucleotides, increase the rate of self-assembly, and possibly damage the guanine molecules to increase the production of 8-oxoguanine. The quadruplex electrochemically detectable oligonucleotide tags form a supernatant that is removed from the microtiter well and transferred to a biosensor where the tags can bind or hybridize to the surface of a working electrode. A rapid voltammetry scan such as SWV at 1400 mV/s produces an 8-oxoguanine peak signal at around 0.47 V. The net 8-oxoguanine peak signals less the negative control signal is compared to a standard curve for the analyte to convert the signal to a measure of the presence and/or quantity of analytes in the sample.

In another embodiment the tags can be 100 mer PolyG to increase the sensitivity. In another embodiment, the majority of the nucleotides within a set of single-stranded oligonucleotide detection tags are guanine, and when used for detecting and/or quantifying multiple analytes simultaneously from the same sample, the nucleotides within the single-stranded oligonucleotide detection tags are selected from the group consisting of guanine, adenine, and thymine, and wherein the combination of said nucleotides produces a unique oligonucleotide tag that is used to detect and/or quantify a specific analyte or group of specific analytes. The above embodiment works like a modified sandwich ELISA. In other embodiments, the steps can be performed sequentially to work like an adapted direct ELISA, an indirect ELISA, or a competitive ELISA.

In another embodiment, the wells are replaced with magnetic microparticles which contain the capture antibodies. This allows a magnetic separation process to extract analytes from non-specific materials that can inhibit detection or unintentionally bind with detection antibodies to cause false signals. The above methods can be used on numerous device platforms such as a microtiter, cartridge, lateral flow device, point of care device, point of use device, portable or field device, development kit, panel, and high throughput instrument.

Experiments

In the course of discovering this invention, experiments were undertaken to improve the sensitivity for measuring single-stranded electrochemically detectable oligonucleotide tags used for detecting and/or quantifying analytes in a fluid sample. As a primary constraint it was determined for industry usefulness that the improved sensitivity must be achieved using a simple and very low cost biosensor. According to DropSens (Llanera, Spain) various electrochemical biosensors are commercially available based on the biosensor's electrode material, sensitivity as measured by the Limit of Detection (LOD), and price. The most popular DropSens electrochemical biosensor employed screen printed carbon electrodes with a LOD of 100 pM for hydroquinone diphosphate/silver ions HQDP/Ag+. Reduced LOD is available by modifying the biosensor carbon working electrode with carbon nanotubes at 50 pM, or gold nanoparticles at 5 pM. As would be understood by those skilled in the art, these modifications significantly increase the price of the biosensor and the corresponding cost per test. In addition the nanostructures employed on the biosensors increase the complexity of fabrication, which can reduce the production yield, the biosensor reliability and the electrode shelf life making these more sensitive biosensors less appealing to industry.

DropSens' screen printed carbon electrodes were used in experiments to evaluate the sensitivity of single-stranded electrochemically detectable oligonucleotides. Baseline experiments were conducted using single-stranded electrochemically detectable oligonucleotides with 20-mer guanine as a polyGuanine (polyG) sequence, Differential Pulse Voltammetry (DPV) with a 25 mV/s scan rate, 5 pM Ruthenium Bipyridine electron transport mediator, and sodium acetate detection buffer. As known by one skilled in the art, it is possible to increase the amplitudes of the electrochemical signal in voltammetry scans by increasing the scan rate. Therefore in a complement experiment, the same test parameters were evaluated by replacing the DPV scans with Square Wave Voltammetry (SWV) scans employing a scan rate of 1400 mV/s.

Figure 5B:
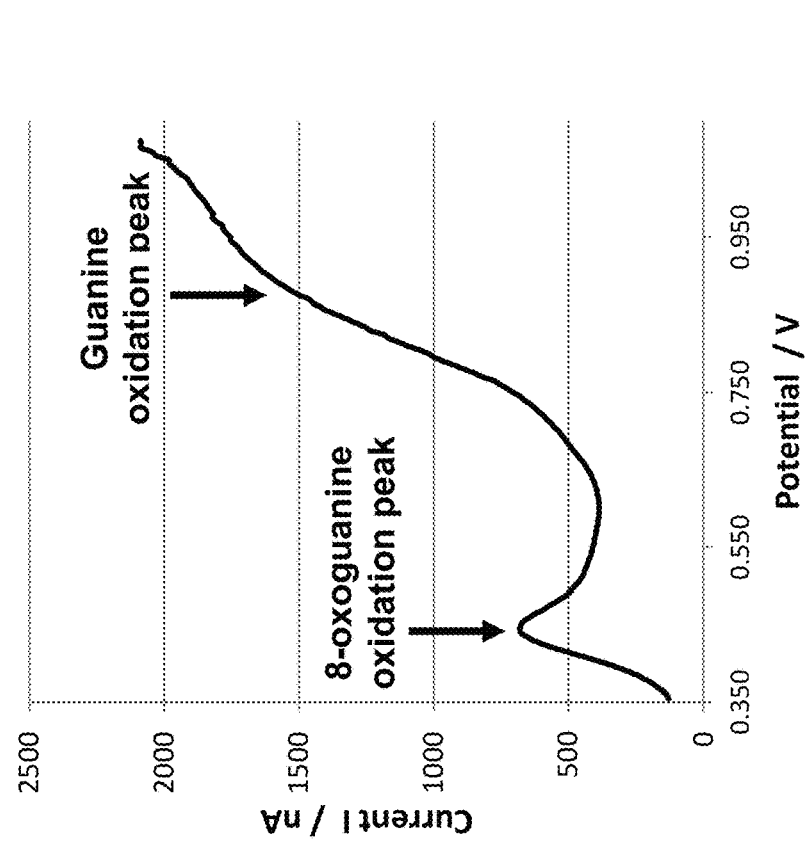
FIG. 5B is a graph of Current vs. Potential for a fast scan rate and 50 pM of electrochemically detectable quadruplex tags.
Figure 5A:
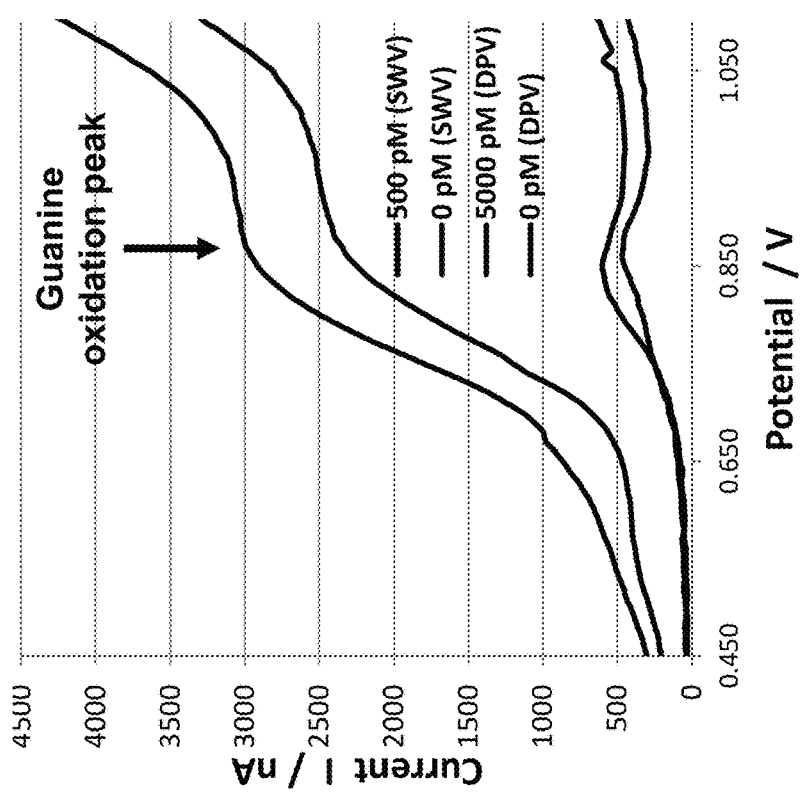
FIG. 5A is a graph of Current vs. Potential for concentrations of electrochemically detectable quadruplex tags using different voltammetry scan rates.

Referring to FIG. 5A, guanine oxidation scans were conducted for solutions containing single-stranded electrochemically detectable tags and negative controls with no tags (noted as 0 pM) using both SWV at 1400 mV/s and DPV at 25 mV/s. Guanine oxidation scans under these conditions produced peaks signal at around 0.9 V. The peak signal currents from highest to lowest are approximately: 3000 nA for SWV from 500 pM of tags in buffer, and 2300 nA for SWV from buffer without tags producing a net signal of 700 nA from 500 pM of tags at 1400 mV/s. The peak signals also provide about 600 nA for DPV from 5000 pM of tags in buffer, and 500 nA for DPV from buffer without tags producing a net signal of 100 nA from 5000 pM of tags at 25 mV/s. This data demonstrated that the faster scan rate produced a net signal that was 600 nA greater for guanine oxidation (i.e. 700 nA-100 nA) and doing so for with a sample that was 1/10th of the concentration (500 pM vs. 5000 pM).

It was next assumed that the concentration of Ruthenium Bipyridine electron transport mediator may not be optimal for the lower tag concentrations detectable with the faster scan rate. In particular, it was thought that lower concentrations of tags may require a proportionately lower concentration of Ruthenium Bipyridine since there were less guanine electrons to transport to the electrode surface. The excess Ruthenium Bipyridine may unintentionally increase the background signal.

Referring to FIG. 5B, the SWV scan of 1400 mV/s was repeated for a 50 pM concentration of single-stranded electrochemically detectable oligonucleotide tags (20-mer PolyG) and a reduced level of Ru(bpy) from 5 pM to 1 nM. The scans produced an oxidation peak at 0.9 V for guanine oxidation, and unexpectedly also produced a second oxidation peak at 0.47 V which corresponded to the guanine derivate 8-oxoguanine (Oliveira-Brett, et al). The 8-oxoguanine peak was not obvious since it did not appear in previous voltammetry scans. More specifically, the novel conditions to produce 8-oxoguanine signals comprised a) increasing the voltammetry scan rate by about 3 logs, and b) reducing the Ru(bpy) concentration by over 3 logs, and c) heating the oligonucleotides to 90° C. for 10 minutes in order to denature the oligonucleotides to prevent oligonucleotides from clumping. Heating is known to damage guanine and facilitate 8-oxoguanine oxidation (Bruskov, et al.)

It was also noted that the detection buffer included 100 μL of sodium acetate which supplied Na+ cations. This provided the cations required for single-stranded electrochemically detectable oligonucleotide tags to self-assemble to quadruplex electrochemically detectable oligonucleotide tags. Referring again to FIG. 5A, the higher concentration of Ru(bpy) may have inhibited the Na+ cations from facilitating the formation of guanine quadruplexes.

Figure 6A:
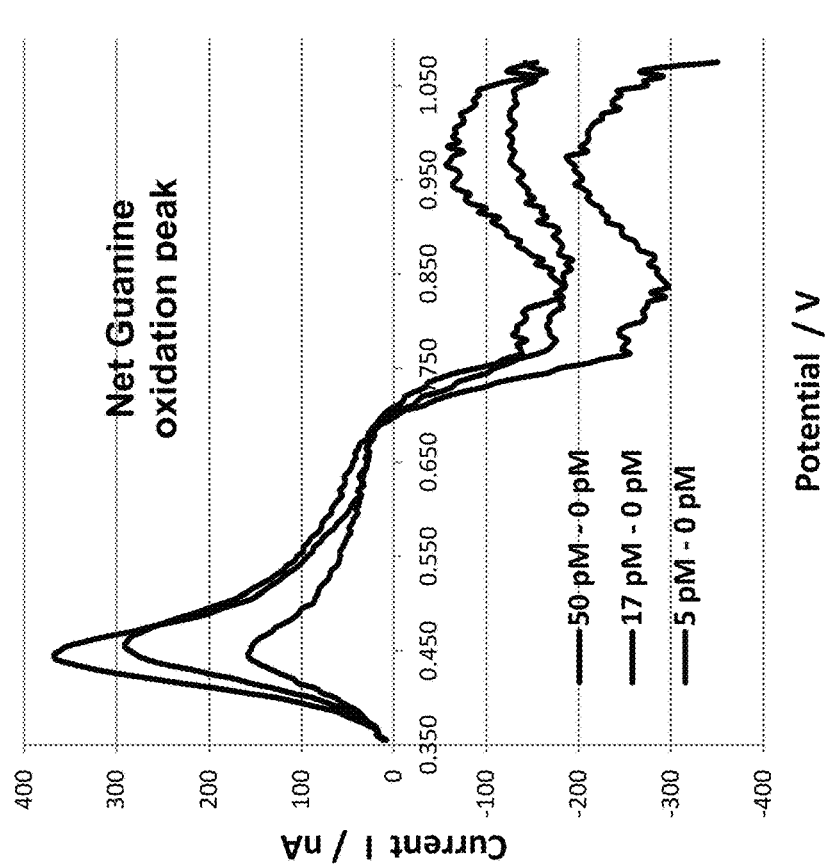
FIG. 6A is a graph of Current vs. Potential for different concentrations of electrochemically detectable tags plus the buffer signal.
Figure 6B:
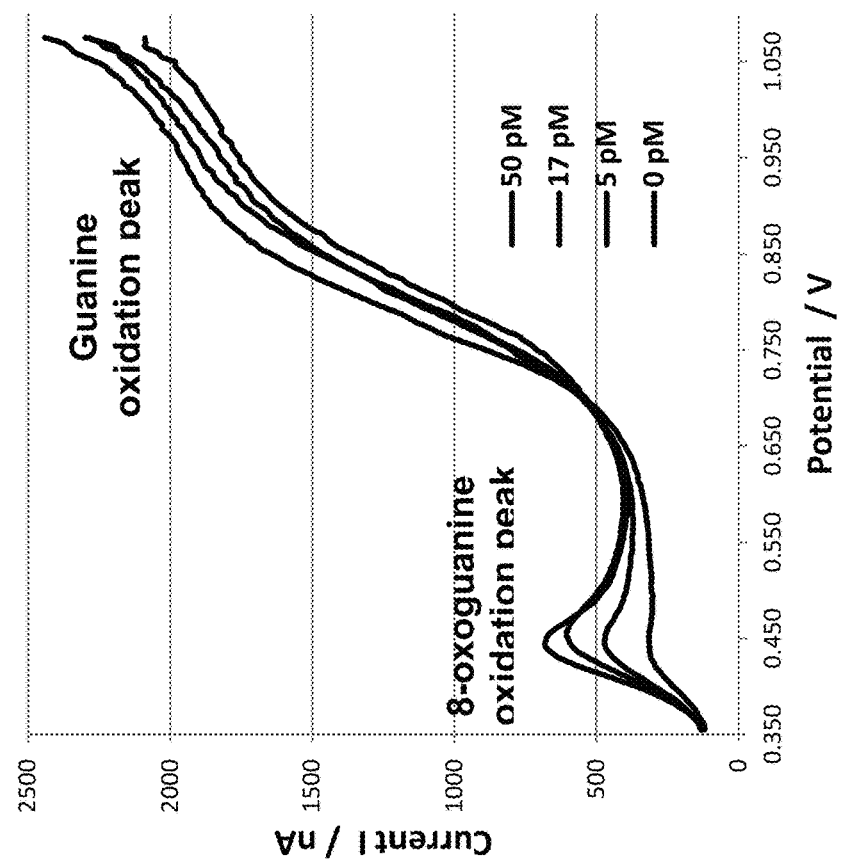
FIG. 6B is a graph of Current vs. Potential for different net concentrations of electrochemically detectable tags minus the buffer signal.

Referring to FIGS. 6A and 6B, concentrations of single-stranded electrochemically detectable oligonucleotide tags were further reduced and included 50 pM, 17 pM and 5 pM, along with a 0 pM negative control and 1 nM of Ru(bpy) electron transport mediator. FIG. 6A plots the absolute signals from the 20-mer PolyG tags and buffer, while FIG. 6B plots the net signals of 20-mer PolyG tags minus the buffer. It is noted that when the tag concentrations are reduced the net signals for guanine oxidation at 0.9 V is negative which indicates that the tags are not distinguishable from noise at 50 pM or lower. In contrast, the 8-oxoguanine signals at 0.47 V are greater than zero for 50 pM, 17 pM and 5 pM and produce signals that are bigger for higher concentrations of PolyG tags.

Figure 7:
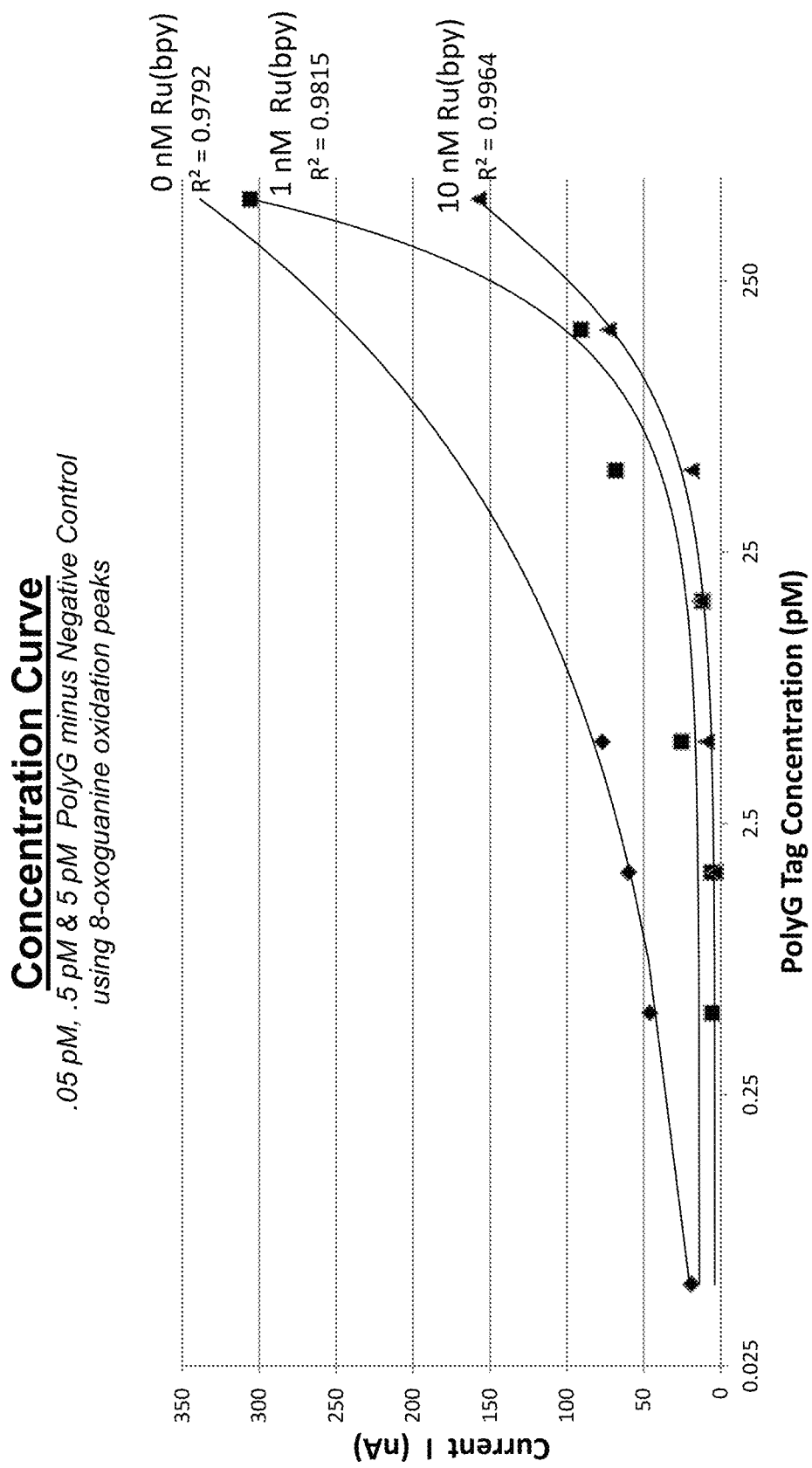
FIG. 7 is a graph of Current vs. Tag Concentration with different concentrations of Ruthenium Bipyridine.

Referring to FIG. 7, 8-oxoguanine oxidation peaks were measured for PolyG tags with concentrations of 0.05 pM, 0.5 pM, and 5 pM in the presence of 10 nM Ru(bpy), 1 nM Ru(bpy) and 0 nM Ru(bpy). Net signals in nA are indicated in Table 3. It was found that even lower concentrations of PolyG tags can be quantified by eliminating the Ru(bpy) electron transport mediator.

TABLE 3

Net PolyG tag signals from 8-oxoguanine oxidation
peaks at different concentrations of PolyG tags
and Ru(bpy) electron transport mediator

| PolyG (pM) | 0 nM Ru(bpy) Current (nA) | 1 nM Ru(bpy) Current (nA) | 10 nM Ru(bpy) Current (nA) |
|---|---|---|---|
| 500 | | 306.0 | 157.6 |
| 165 | | 90.9 | 73.1 |
| 50 | | 68.2 | 19.1 |
| 16.5 | | 11.5 | 13.1 |
| 5 | 77.4 | 25.5 | 9.3 |
| 1.65 | 59.6 | 5.8 | 3.7 |
| 0.5 | 46.4 | 5.4 | |
| 0.05 | 19.4 | | |

While these experiments demonstrated the greatly improved measurable levels of electrochemically detectable oligonucleotide tags, it is also possible to illustrate the corresponding improved sensitivity for measuring low levels of analytes. Analytes may be any biological material of interest which one may wish to identify, detect or quantify. Examples of analytes include cells, bacteria, protozoa, fungi, virus particles, proteins, peptides, enzymes, hormones, haptens, cancer markers, nucleic acids, genes, oligonucleotides, DNA, RNA, small molecules, drugs, pesticides, organic chemicals, industrial chemicals and compounds. Analytes can be species-specific, strain-specific, genotype-specific, or cluster-specific. The use of the term "target" can be applied to indicate one of more specific analytes that one wishes to identify, detect or quantify. The level, amount, copies and/or concentration of an analyte can vary greatly in a sample. As would be understood by those skilled in the art, it is much more difficult to identify, detect and quantity low levels of analytes, particularly in the presence of much greater levels of non-specific materials. The material used for binding analytes with single-stranded electrochemically detectable oligonucleotide tags can include antibodies, monoclonal antibodies, polyclonal antibodies, amino acids, peptides, proteins, haptens, nucleic acids, oligonucleotides, DNA, RNA, aptamers, and combinations thereof.

Referring to FIG. 7, concentration curves were produced from 8-oxoguanine oxidation signals using different concentration standards for 20-mer PolyG electrochemically detectable oligonucleotide tags. In one embodiment the upper concentration curve produced from 20-mer PolyG electrochemically detectable oligonucleotide tags and 0 nM of Ru(bpy) was used to determine an analyte level based the concentration of its associated tags. In one example, there is 1 tag binding per analyte and a 60% recovery or binding efficiency from the antibody matched pairs comprising a set of capture antibodies and detection antibodies. Using this curve, a measurable quantification level of 0.05 pM tags would associate with 1 tag per analyte with 60% binding efficiency. The associated level of analytes is 0.05 pM tags×1 analyte/tag×1/60% efficiency=0.08 pM analytes.

Figure 21A:
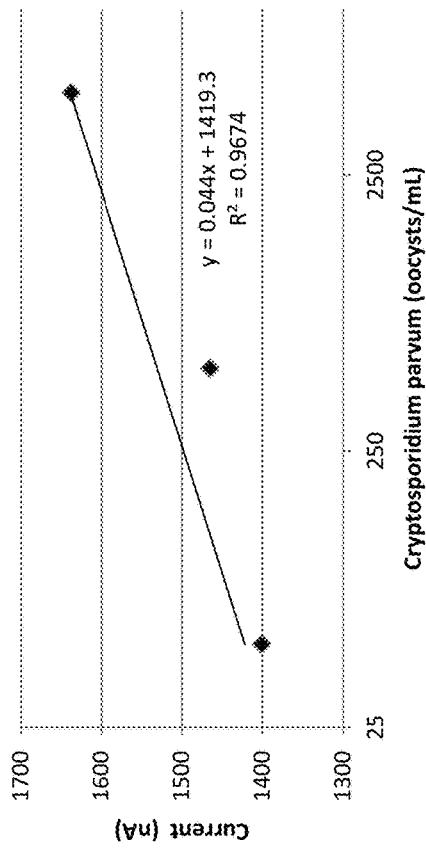
FIG. 21A is a concentration curve developed for cryptosporidium from known samples.

In another embodiment, detection antibodies are bound to nanoparticles which also bind 1000 single-stranded electrochemically detectable oligonucleotide tags. Using same this curve, a measurable quantification level of 0.05 pM tags would associate with 1000 tags per analyte with 60% binding efficiency. Therefore the associated level of analytes is 0.05 pM tags×1/1000 analytes/tag×1/60% efficiency=0.08 fM analytes. In another embodiment, detection antibodies are bound to microparticles which also bind 1,000,000 single-stranded electrochemically detectable oligonucleotide tags. Using same this curve, a measurable quantification level of 0.05 pM tags would associate with 1,000,000 tags per analyte with 60% binding efficiency. Therefore the associated level of analytes is 0.05 pM tags×1/1,000,000 analytes/tag×1/60% efficiency=0.08 aM analytes. Referring to FIG. 21A, in another embodiment the concentration curve is made from known analytes in the sample media to be tested. Some of the other benefits and unique features of the invention include:

Robustness—The invention can be used for a wide range of analyte types and specific protein markers, such as immunoglobulins, surface proteins on bacteria and viruses, protein toxins, hormones, and enzymes. Nucleic acids can also be detected and quantified.

Rapid Detection Time—All process steps can be undertaken in about 1 hour using prefabricated consumables.

Low Cost—By avoiding optional detection and transduction, relatively inexpensive reagents and equipment are needed to conduct a test.

Ease of Use—The invention's process steps invention can be automated and used in a point-of-care device with no operator involvement.

Not only could this invention allow diseases, cancers and medical conditions to be detected at a much earlier stage when treatment options are less expensive and more successful, it could also enable a new generation of diagnostics that can measure extremely low level analytes using a rapid, simple and inexpensive point-of-care device, similar to a glucose meter. However, the truly innovative aspect of the invention is allowing ultra-low levels of virtually any biological analyte to be detected and quantified rapidly, simply and inexpensively with an electrochemical biosensor. A comparison of the measurement capabilities of the invention with other biodetection platforms is provided in the following tables. The values and estimates are sourced from references that describe detection limits for a wide range of similar groups of technologies and platforms. Specific technologies can have values that deviate from the values being reported. The term measurement capability is used as a general term to correlate comparative values reported for sensitivity, limit of detection and limit of quantification.

Relative detection sensitivities of redox electrochemical biosensors are provided in Table 4. Values are reported for glucose meters since the vast majority of commercial redox biosensors are used for the detection of glucose in blood. Values are provided for the lower range of blood glucose measurements, commercial glucose enzyme biosensors, and experimental glucose nanobiosensors. Comparative values from this invention are also provided to illustrate the vastly improved measurement capability from the invention's self-assembly tag capability. The first rows of Table 4 show the lower concentration requirement for measuring glucose in whole blood as 1.1 mmol/L (or 1.1 mM). Some commercial glucose meters such as Abbott FreeStyle® (Abbott Diagnostics Care, Alameda, Calif.) detect glucose from a 0.3 µL sample. Since commercial glucose meters need to measure the lowest required glucose levels, they typically have the additional capability to measure significantly lower levels as a safety margin. Kozar indicates a measurement capability of 0.033 mmol/L (or 33 µM) for Accu-Chek Compact Plus® portable instrument (Roche Diagnostics GmbH, Mannheim, Germany). This converts to about 33 times lower than the lower range of glucose levels.

Lower measurement limits have been achieved with nanobiosensors that employ nanometer-scaled structured materials as the working electrode. Nanobiosensor working electrodes have a smaller electro-active surface area than conventional biosensors. This improves the biosensor's signal-to-noise resolution by allowing small electrical signals generated from lower levels of analytes to be distinguished from background noise. Zhu reports a measurement capability of approximately 0.00001 mmol/L (or 10 nM) for certain nanobiosensors, which converts to about 300 times lower levels than conventional biosensors. Many nanobiosensor are not commercially viable as they encounter high fabrication costs, inconsistency signals from sensor to sensor due to poor fabrication quality at the nanoscale, and difficulties in measuring low nanoAmp and picoAmp signals. In contrast, this invention can attained 0.08 pM-0.08 aM concentrations, which is an 11 order of magnitude improvement over the measurement capabilities of glucose nanobiosensors.

TABLE 4

Relative Measurement Capabilities of Representative Redox Biosensors and the Invention

| Measurement Capabilities | Blood Glucose Lower Limit | Glucose Enzyme Biosensor | Glucose Nano-biosensor | Invention Oligo Tags Direct and With Microparticle |
|---|---|---|---|---|
| LOD or LOQ | 1.1 mM | 3.3 µM | 10 nM | .08 pM-.08 aM |

Table 5 provides the relative measurement capabilities of representative direct ELISA and sandwich ELISA platforms used for the detection of proteins. The values and estimates are provided from ELISA technical documents published by KPL (Gaithersburg, Md.) and Thermo Scientific (Rockford, Ill.). Sandwich ELISAs using horseradish peroxide (HRP) enzymes and colorimetric detection are the most common immunoassays. ELISA measurement capabilities are typically expressed in pg/mL. For a typical protein such as Interleukin 2 (IL-2), the relative detection limits are approximately 2125 pg/mL for direct ELISA and 1.4 pg/mL for sandwich ELISA. ELISA applications requiring sensitivities below 1 pg/mL can be obtained using chemiluminescent or chemifluorescent substrates which are much more expensive and more difficult to use. Because the molecule weights of proteins vary, a better unit to compare detection platforms is pmols (pM). For example, in the case of Interleukin 2 (IL-2) protein with a molecular weight of 17,000 g/mol, 2125 pg/mL can be converted to pM by dividing the concentration of 2125 pg/mL by the molecular weight of 17,000 g/mol and multiplying by 1000 mL/L. This provides detection capabilities of approximately 125 pM for direct ELISA and 0.08 pM for sandwich ELISA.

The sensitivity for sandwich ELISA is higher because of signal amplification. Each primary antibody contains several epitopes that can be bound by the labeled secondary antibody. Sandwich ELISA can also be made more sensitive using avidin-biotin complexes which have multiple sites for enzymes. This allows up to about 200 enzymes per analyte. In comparison, this invention provides many orders of magnitude greater sensitivity with increased signal-to-noise resolution and by binding $10^6$ single-stranded electrochemically detectable oligonucleotide tags per analyte with a microparticle. Using data from the example described earlier, the invention was able to detect 6 orders of magnitude lower levels than sandwich ELISA as illustrated in Table 5.

TABLE 5

Relative Measurement Capabilities of Direct ELISA, Sandwich ELISA and the Invention

| Measurement Capabilities | Direct ELISA | Sandwich ELISA | Invention Oligo Tags Direct and With Microparticle |
|---|---|---|---|
| LOD or LOQ | 125 pM | .08 pM | .08 pM-.08 aM |

Table 6 provides the relative measurement capabilities of emerging biodetection technologies. One group of technologies is bead sandwich ELISA where sandwiches are made using a first bead with a capture antibody, and a second bead with a detection antibody and an optical detectable label. Bead sandwich ELISA replaces a solid substrate from conventional ELISA with beads to provide less surface area for non-specific materials to bind to. The capture bead is typically a magnetic bead that permits magnetic separation to remove non-specific materials that could interfere with detection. The detection bead is typically a polymer and is also attached to an optical label. Singulex (Alameda, Calif.) uses detection beads with fluorescent dyes which are individually counted using an optical measurement device. Quanterix (Lexington, Mass.) uses fluorophores to generate optical signals in individual femtoliter wells. The measurement capabilities reported by Quanterix is about 76 aM shown in Table 6 as an improvement over sandwich ELISA by approximately 5 orders of magnitude. These systems are more expensive and more difficult to use than ELISA. Luminex (Austin, Tex.) has a second type of bead sandwich ELISA (xMAP). xMAP replaces the magnetic bead with a second polymer bead which uses a second fluorescent which is unique to the analyte to allow each analyte to be identified. The xMAP approach is less sensitive than magnetic bead sandwich ELISA but is more effective for high throughput and large multiplexing detection applications.

Another group of emerging detection technologies is immuno-nanobiosensors which use nanobiosensors, antibodies and enzymes to detect proteins. Immuno-nanobiosensors have employed gold nanoparticles, carbon nanotubes, magnetic particles, and quantum dots to improve the detection capabilities over conventional biosensors. Chikkaveeraiah reports that certain immuno-nanobiosensors have been able to detect approximately 0.17 pM levels using multi-label amplification which can have up to a few thousand detectable labels per analyte. However, this limited amplification is unable to reach limits of detection required by clinical applications. Furthermore, none of these technologies come close to attaining the invention's capability of 0.08 aM to detect extremely low levels. This is attained at a fraction of the cost of bead sandwich ELISAs.

TABLE 6

Relative Measurement Capabilities of Emerging Detection Technologies and the Invention

| Measurement Capabilities | Bead Sandwich ELISA | Immuno-Nanobiosensor | Invention Oligo Tags Direct and With Microparticle |
|---|---|---|---|
| LOD or LOQ | 76 aM | 0.17 pM | .08 pM-.08 aM |

In term of its usefulness, the present invention can be valuable for the early diagnosis of diseases, cancers, and medical conditions, as well as in bioterrorism, food and water safety, biotechnology, pharmaceutical, and forensic applications. Representative applications are shown below.

TABLE 7

Representative Infectious Disease Applications

| | Blood/Plasma/Serum | Respiratory Swab/Sputum | Stool |
|---|---|---|---|
| Bacterial Infections | *Yersinia pestis* (Plague) *Rickettsia* (Typhus) VRE *Salmonella typhi* (Typhoid Fever) *B. burgdorferi* (Lyme disease) *Listeria* | *Mycobacterium tuberculosis* *Bacillus anthracis* (Anthrax) MRSA *Acinetobacter baumannii* *Mycobacterium leprae* (Leprosy) *Legionella* | *Clostridium difficile* *Klebsiella* *Vibrio cholerae* (cholera) *Salmonella* *Campylobacter* *Escherichia coli* |
| Viral Infections | Human Immunodeficiency Virus Hepatitis West Nile Virus Ebola (Hemorrhagic fever) Marburg virus Arenaviruses Dengue Fever Flaviviridae (Yellow Fever) | Influenza (H1N1, H5N1) SARS Variola (Smallpox) Adenovirus (cold, pneumonia) Morbillivirus (Measles) Varicella zoster virus (Chickenpox) Rubella (German Measles) | Norovirus Rotavirus Poliovirus |
| Parasitic/Fungal Infections | Plasmodium (malaria) | Aspergillus | Schitosoma Cryptosporidium Giardia |

TABLE 8

Representative Cancer and Medical Condition Applications

| | Cancer Biomarkers | Medical Condition or Disease Biomarkers |
|---|---|---|
| Protein Biomarkers | Ovarian cancer (HE4) Various cancer types (CA125, CEA) | Rheumatoid arthritis (Anti-CCP) Rheumatoid arthritis (Anti-RF) Pre-eclampsia (sFlt/PlGF) Heart failure (NT-proBNP) Acute coronary syndrome (Troponin T/Troponin I) Osteoporosis (b-crosslaps, P1NP) Growth disorders (hGH) Transplantation (MPA levels) |
| Genetic Biomarkers | Melanoma (BRAF Mutation) Colorectal cancer (KRAS) | Sepsis SeptiFast Test |

It is understood that the above list and subsequent descriptions are given by way of example only, and is not limitative to the scope of the present invention. "Pharmaceutically acceptable" in the context of the present invention means a device or composition that is generally safe, non-toxic and biologically acceptable for veterinary and human use. The invention also comprises many other unique capabilities. A partial list includes one or more of the following that can be used in an assay: a configurable oligonucleotide tag that can be lengthened to increase sensitivity, a configurable oligonucleotide tag that can have unique sequences to enable multiplexing, a sample preparation method that attaches tags to particles to increase sensitivity, a sample preparation method that employs magnetic particles to remove nonspecific materials that can cause false signals, a sample preparation method that can use one or more of filters, chemicals, and mechanical processes to extract analytes from a larger sample to increase sensitivity, an low cost biosensor that does not require difficult-to-fabricate nanoscale structures, a family of analyzer configurations, a developer kit that can reduce the time-to-market for developing a diagnostic application from years to months for any validated pair of antibodies, DNA probes or ligands, and a cartridge preparation instrument that allow developers to produce their own test cartridges in a few hours.

The starting sample may be embodied by any fluid which may contain an analyte, such as blood or other bodily fluids, liquefied solids or tissues, water or other liquids, or liquefied materials from air or gases. Examples include but are not limited to peripheral blood, plasma, serum, urine, saliva, nasal swab, tissue biopsy, surgical specimen, amniocentesis sample, autopsy material, body fluid, stool, surface, container, water, liquefied air particles, gases, food, food extracts, beverages, and other materials coming from human subjects, veterinary subjects, animals, rodents, lizards, fish, birds, insects, plants, and biological structures. Original samples may be taken from any source. A sample may also be a liquid derived from the original sample by removing or adding components.

The analyte may be any biological material of interest which one may wish to identify, detect or quantify. Examples of analytes include cells, bacteria, protozoa, fungi, virus particles, proteins, peptides, enzymes, hormones, haptens, cancer markers, nucleic acids, genes, oligonucleotides, DNA, RNA, small molecules, drugs, pesticides, organic chemicals, industrial chemicals and compounds. Analytes can be species-specific, strain-specific, genotype-specific, or cluster-specific. The use of the term "target" can be applied to indicate one of more specific analytes that one wishes to identify, detect or quantify.

In addition to biological analytes, the fluid sample may contain other non-specific materials such as non-target biological materials and non-biological materials. These non-specific materials are not the object of the determination being performed. Some of these non-specific materials can interfere with or aggregate with analytes to prevent the detection of analytes, causing undesirable false negative detection outcomes. Some of these non-specific materials including non-specific species of the analytes can be falsely detected in the absence of the analytes, causing false positive detection outcomes. As well the total sum of non-specific materials can outnumber the sum of analytes in a sample by several orders of magnitude to create substantial noise that prevents the detection signal generated from the analytes to be distinguished from said noise, causing undesirable false negative or inconclusive detection outcomes.

The level, amount, copies and/or concentration of an analyte can vary greatly in a sample. As would be understood by those skilled in the art, it is much more difficult to identify, detect and quantity low levels of analytes, particularly in the presence of much greater levels of non-specific materials. The expression "magnetic separation" refers to a process that physically separates analytes from non-specific materials by binding analytes to magnetically extractable particles. The material used for binding analytes with magnetic particles can include antibodies, monoclonal antibodies, polyclonal antibodies, amino acids, peptides, proteins, haptens, nucleic acids, oligonucleotides, DNA, RNA, aptamers, and combinations thereof. The expression "electrochemical system" refers to a system that determines the presence and/or quantity of a redox analyte through measurements of electrical signal in a solution between a working electrode and a counter electrode, such as induced by a redox reaction or electrical potential from the release or absorption of ions. The redox reaction refers to the loss of electrons (oxidation) or gain of electrons (reduction) that a material undergoes during electrical stimulation such as applying a potential. Redox reactions take place at the working electrode, and which, for chemical detection, is typically constructed from an inert material such as platinum or carbon. The potential of the working electrode is measured against a reference electrode, which is typically a stable, well-behaved electrochemical half-cell such as silver/silver chloride. The electrochemical system can be used to support many different techniques for determining the presence and concentration of the target biomolecules including, but not limited to, various types of voltammetry, amperometry, potentiometry, coulometry, conductometry, and conductimetry such as AC voltammetry, differential pulse voltammetry, square wave voltammetry, electrochemical impedance spectroscopy, anodic stripping voltammetry, cyclic voltammetry, and fast scan cyclic voltammetry. The electrochemical system may further include one or more negative control electrode, and positive control electrode. In the context of the present invention, a single electrochemical system may be used to detect and quantify more than one type of target analyte.

It will be readily understood by those skilled in the art that the amplification methods and devices of embodiments of the present invention may be used in combination with different types of detection devices than the one described above. For example, these can include detection devices that measure changes in electrical properties, light output or absorbance, mass, temperature, and size, shape and conductivity of a conductive channel in a field effect transistor, among others.

Self-Assembling Electrochemically Detectable Oligonucleotide Tags

Referring to FIG. 1A a graphic is provided illustrating an electrochemically detectable oligonucleotide tag for detecting and/or quantifying the level of one or more target analytes in a fluid sample. The tag consists of a single-stranded electrochemically detectable oligonucleotide 101 that temporarily binds to an analyte 102 directly as in 103a, or indirectly using one or more ligands 103b and particles 103c. a single-stranded electrochemically detectable oligonucleotide then self-assembles into a quadruplex electrochemically detectable oligonucleotide 104 when exposed to cations 105 that enable quadruplex self-assembly. In one embodiment the cations are Na+ and provided in an elution buffer such as 80 mM NaOAc (pH 9) and 95% formamide. In another embodiment the cations are Na+ and provided in a detection buffer of 0.2 M sodium acetate (pH 5.2). In other embodiments the cations could be K+ or other monovalent cations.

Figure 1B:
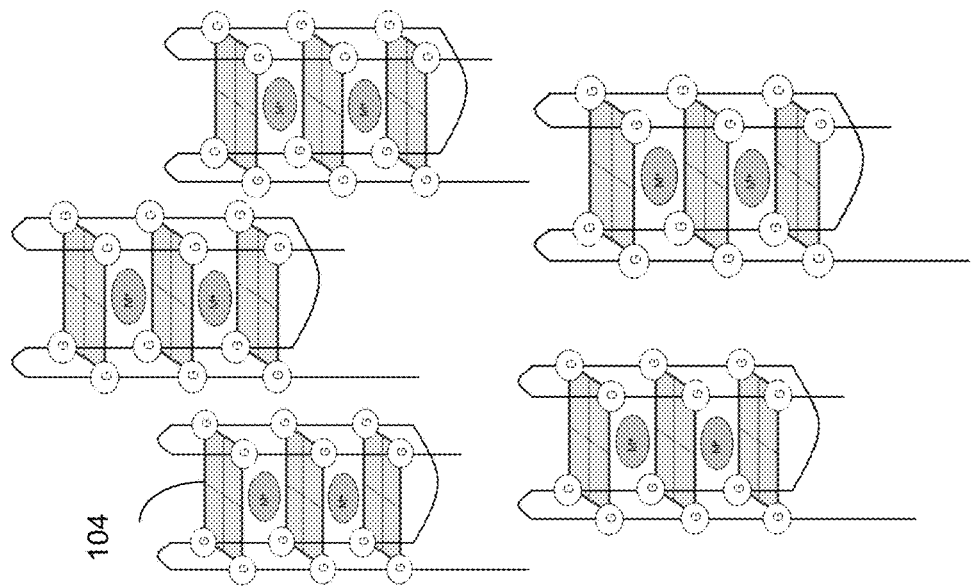
FIG. 1B is a schematic representation of quadruplex electrochemically detectable oligonucleotide tags binding to analytes directly or indirectly using a ligand or particle.
Figure 1B:
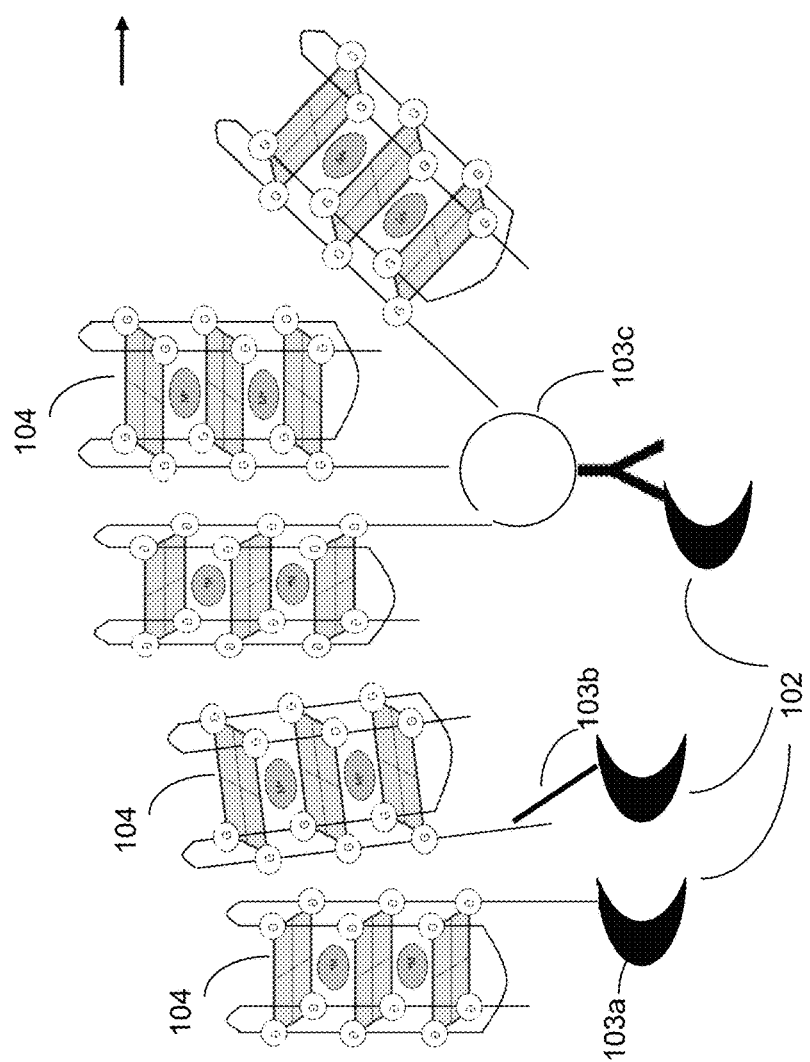

Referring to FIG. 1B, graphic is provided illustrating another embodiment where the tag consists of a quadruplex electrochemically detectable oligonucleotide 104 that temporarily binds to an analyte 102 directly as in 103a, or indirectly using one or more ligands 103b and particles 103c. The single-stranded electrochemically detectable oligonucleotides self-assemble into quadruplex electrochemically detectable oligonucleotide tags 104 before the tags are bound to the analytes. Referring again to FIG. 1A, the majority of the nucleotides within said single-stranded electrochemically detectable oligonucleotide tags 101 are guanine with at least 4 guanines in a consecutive sequence. The majority of the nucleotides within said single-stranded oligonucleotide detection tags are guanine, and when used for detecting and/or quantifying multiple analytes simultaneously from the same sample, the nucleotides within the single-stranded oligonucleotide detection tags are selected from the group consisting of guanine, adenine, thymine, and cytosine, and wherein the combination of said nucleotides produces a unique oligonucleotide tag that is used to detect and/or quantify a specific analyte or group of specific analytes.

FIGS. 2A and 2B provide two different chemical notations for the guanine molecule. Referring to FIGS. 2C and 2D, sets of 4 guanine self-assemble into square planar tetrad structures 110 bound by eight Hoogsteen hydrogen bonds. Two or more square planar tetrad structures 110 are stacked on top of each other and stabilized by pi-pi hydrophobic interactions, wherein between each square planar tetrad structure in the stack is a monovalent cation M+ 105 which is coordinated to the lone pairs of electrons of O6 111 in each guanine. In one embodiment of this invention, the electrochemical signals are produced from the oxidation and/or reduction of 8-oxoguanine from C8 of guanine 112 using a redox detection technique.

The quadruplex electrochemically detectable oligonucleotide tags can change in shape, structure, and performance by modifying one or more of the number of guanines, the number of nucleotides, the sequence of nucleotides, the cation molecule, the cation concentration, the temperature during self-assembly, the pH during self-assembly, the presence of chemicals during self-assembly, and the use of mechanical agitation. In another embodiment the majority of the nucleotides within the single-stranded electrochemically detectable oligonucleotide tags are adenine with at least 4 adenine in a consecutive sequence and the quadruplex electrochemically detectable oligonucleotides are exposed, adsorbed or hybridized to a biosensor working electrode surface wherein a redox detection technique oxidizes adenine and produces 8-oxoadenine signals.

Detection and Quantification Methods

Figure 3A:
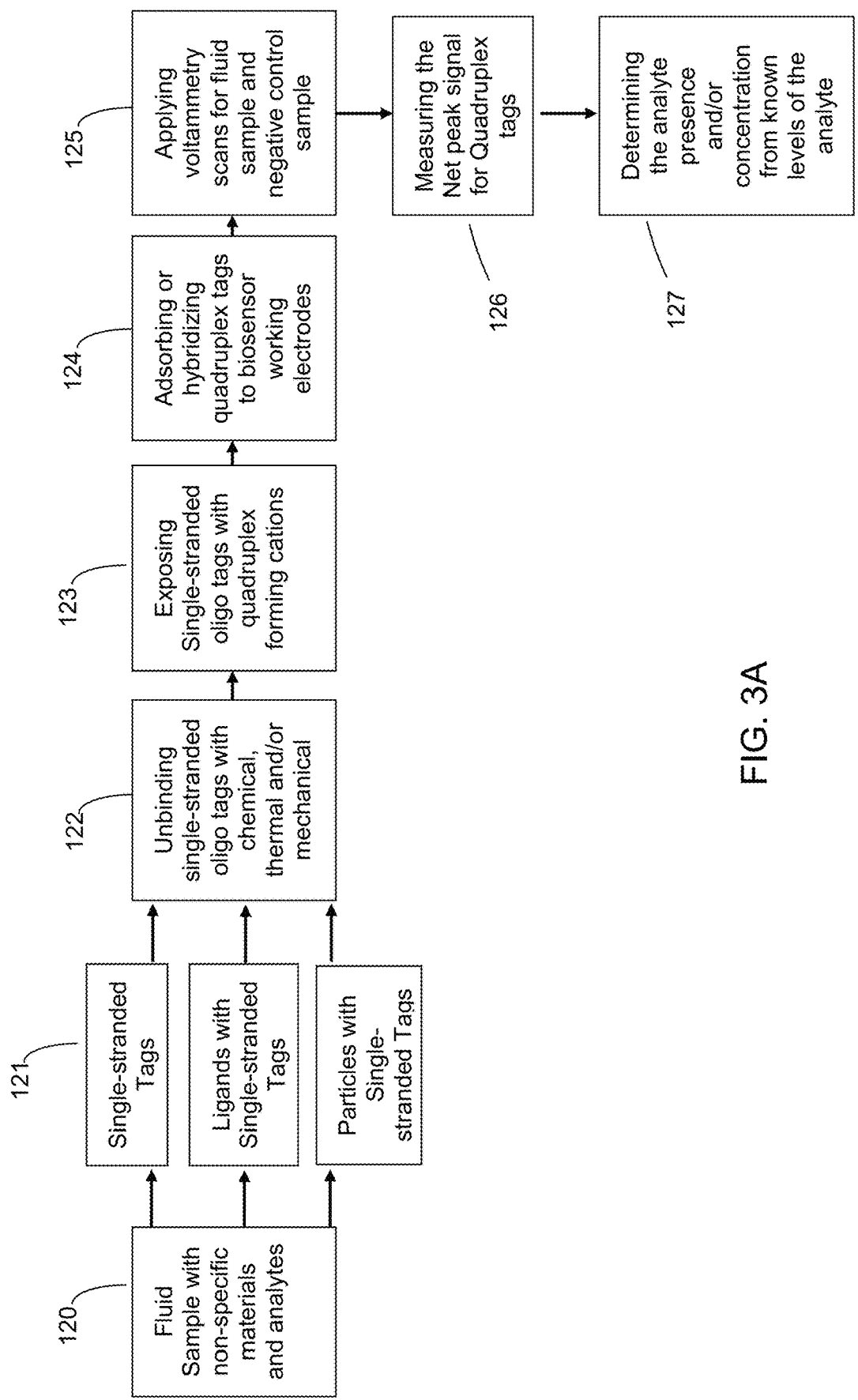
FIG. 3A shows a flow chart illustrating a detection method according to an embodiment of the present invention.

Referring to FIG. 3A, a flow chart is shown illustrating the main steps of a method for detecting and/or quantifying the level of one or more target analytes in a fluid sample. The method comprises the following steps performed sequentially: (a) providing a fluid sample that may contain non-specific materials and one or more analytes 120; (b) providing one or more sets of a plurality of single-stranded electrochemically detectable oligonucleotide tags that temporarily bind to an analyte directly, or indirectly using one or more of ligands and particles 121; (c) unbinding the single-stranded electrochemically detectable oligonucleotide tags from the analytes with one or more of chemicals, heat and mechanical processes 122; (d) exposing the single-stranded electrochemically detectable oligonucleotide tags to monovalent cations that enable the single-stranded electrochemically detectable oligonucleotide tags to self assemble into quadruplex electrochemically detectable oligonucleotide tags 123; and (e) providing one or more working electrodes and adsorbing or hybridizing quadruplex tags to the biosensor working electrodes for redox detection 124.

In another embodiment, the electrochemical detection technique in step (e) performs a redox detection scan on each working electrode 125, whereby (f) the generated signal from 8-oxoguanine oxidation or reduction is measured as the difference in the redox scan peak signal from a buffer containing cations and the self-assembled quadruplex electrochemically detectable oligonucleotide tags associated an analyte or group of analytes, minus the redox scan peak signal from a negative control of the buffer containing cations 126. In another step (g) the analyte is determined to be present if the generated signal from the associated electrochemically detectable oligonucleotide tags in step (a)

is positive and greater than the variation in signal due to noise 127; and (h) the level of an analyte is determined by comparing the generated electrochemical signal from an associated electrochemically detectable oligonucleotide tag in step (a) with predetermined signals from known levels of said analyte 127.

In another embodiment, the method further comprises steps to remove self-assembly inhibitors: (i) before (d) the fluid sample may optionally be treated by one or more of the following: a membrane, a chemical, and a disaggregation technique to remove materials that inhibit the self-assembly of single-stranded electrochemically detectable oligonucleotide tags into quadruplex electrochemically detectable oligonucleotide tags when exposed to cations that enable quadruplex self-assembly, and (j) the exclusion of any reagents that inhibit the self-assembly of single-stranded electrochemically detectable oligonucleotide tags into quadruplex electrochemically detectable oligonucleotide tags when exposed to cations that enable quadruplex self-assembly. In another embodiment, the method further comprises steps to increase the number of single-stranded electrochemically detectable oligonucleotide tags per analyte to amplify the detection signal by replacing step (b) with: (k) providing one or more sets of magnetic particles, wherein each set comprises a plurality of a magnetic particle conjugated with a plurality of a first analyte binding material to create analyte-magnetic particle complexes if an associated analyte is present, and (l) providing one or more sets of nonmagnetic particles, wherein each set comprises a plurality of a nonmagnetic particle conjugated with a plurality of a second analyte binding material that is a matched pair with the first analyte binding material and is also conjugated with a plurality of a single-stranded electrochemically detectable oligonucleotide tag in greater amounts than the bound associated analyte to create single stranded-electrochemically detectable oligonucleotide tag-nonmagnetic particle-analyte-magnetic particle structures if an associated analyte is present.

Figure 3B:
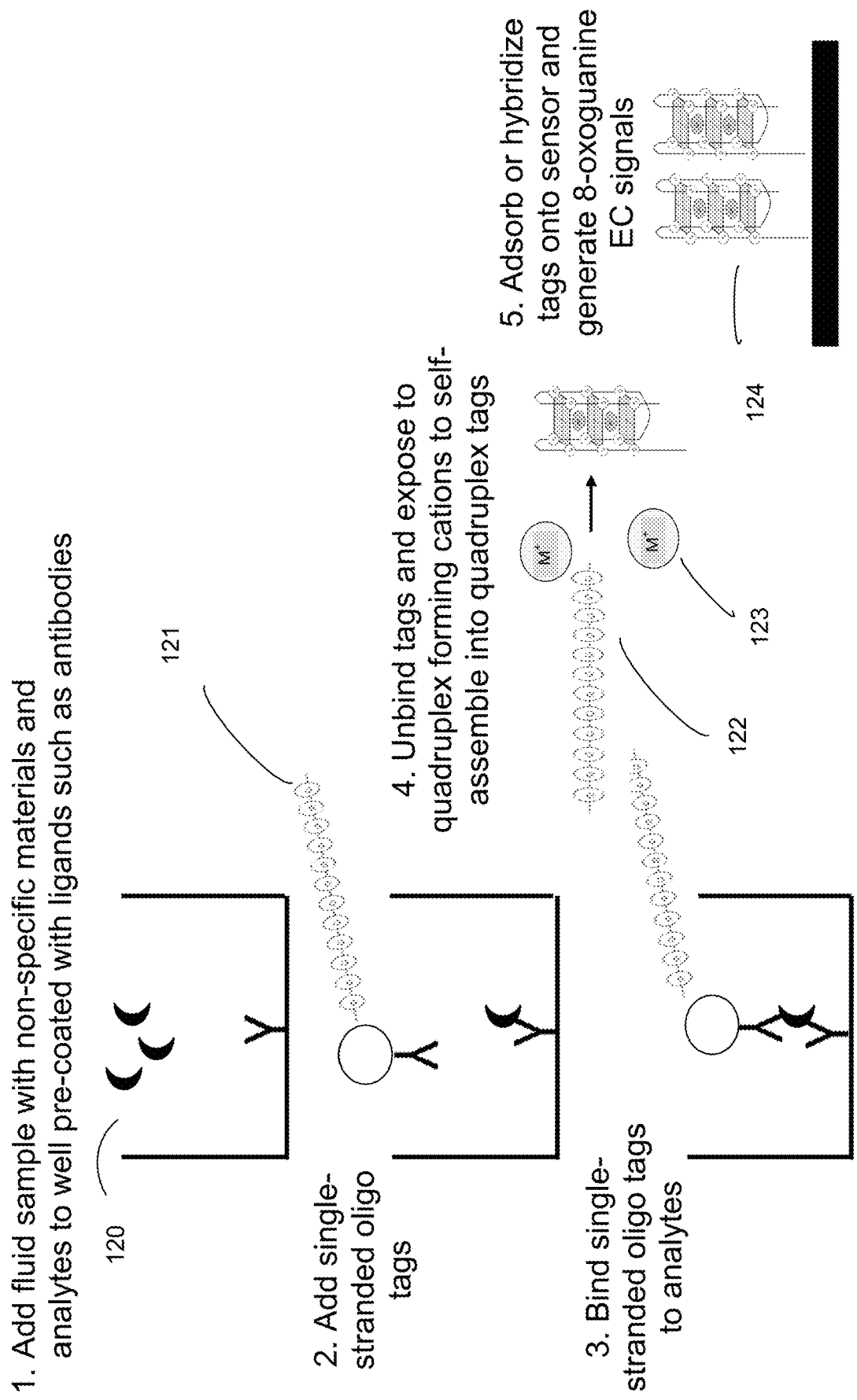
FIG. 3B shows a detection method according to another embodiment of the present invention.

Referring to FIG. 3B, a modified flow chart is shown illustrating another embodiment of the method for detecting and/or quantifying the level of one or more target analytes in a fluid sample. The method begins by (1) providing a fluid sample that may contain non-specific materials and one or more analytes 120. This can involve adding 100 μL sample to a microtiter well pre-coated with antibodies or other ligand and incubated for 30 minutes. The well is washed with a wash buffer to remove nonspecific materials. (2) The method further provides one or more sets of a plurality of single-stranded electrochemically detectable oligonucleotide tags that temporarily bind to an analyte directly, or indirectly using one or more of ligands and particles 121. Referring to FIG. 3B, the single-stranded oligonucleotide tags are bound to particles along with antibodies that are base pairs with the antibodies in step (1), and incubated for 30 minutes. In the case of multiplexing, multiple sets of ligand pairs and unique tag sequences can be used. (3) If analytes are present in the sample, sandwiches are formed with a top layer comprising the single-stranded oligonucleotide with the particles and antibodies, a middle later of the analytes, and a bottom layer with the antibodies pre-coated to the floor and walls of a microtiter well. The wells are washed with a wash buffer to remove unattached tags. (4) The single-stranded electrochemically detectable oligonucleotide tags are unbound from the sandwiches with one or more of chemicals, heat and mechanical processes 122, and then the single-stranded electrochemically detectable oligonucleotide tags are exposed to monovalent cations that enable the single-stranded electrochemically detectable oligonucleotide tags to self assemble into quadruplex electrochemically detectable oligonucleotide tags 123. In one embodiment, single-stranded electrochemically detectable oligonucleotide tags compositing 20-mer guanine were eluted from particles while heated at 90° C. for 10 minutes using 100 μL of 80 mM NaOAc (pH 9) and 95% formamide buffer to provide Na+ cations which allowed single-stranded electrochemically detectable oligonucleotide tags to self-assemble into quadruplex electrochemically detectable oligonucleotide tags. (5) The quadruplex electrochemically detectable oligonucleotide tags are delivered to one or more biosensor working electrodes where they adsorb or hybridize to the working electrodes for redox detection 124. In one embodiment, 100 μL elution supernatant was transferred to a screen printed carbon working electrode in a 96-well microtiter (DropSens, Spain), adsorbed for 10 minutes.

The method continues by generating 8-oxoguanine EC signals using a redox technique. In one embodiment, a square wave voltammetry scan was applied with a 1400 mV/sec scan rate with the following settings: scan increment 5 mV, frequency of 280 Hz (0.0035/sec), pulse height 20 mV, equilibrium time 3 sec, initial E−0.35V, and final E−1.2 V). Referring to FIG. 4A, electrochemical signal versus potential is plotted for oligonucleotide tag concentrations of 5 pM, 0.5 pM and 0.05 pM. A negative control of buffer with no oligonucleotide tag is also provided and indicated as 0 pM. The 8-oxoguanine peak occurs are approximately 0.47V and indicates a higher peak signal for greater concentrations of 20-mer guanine quadruplex electrochemically detectable oligonucleotide tags.

Figure 4B:
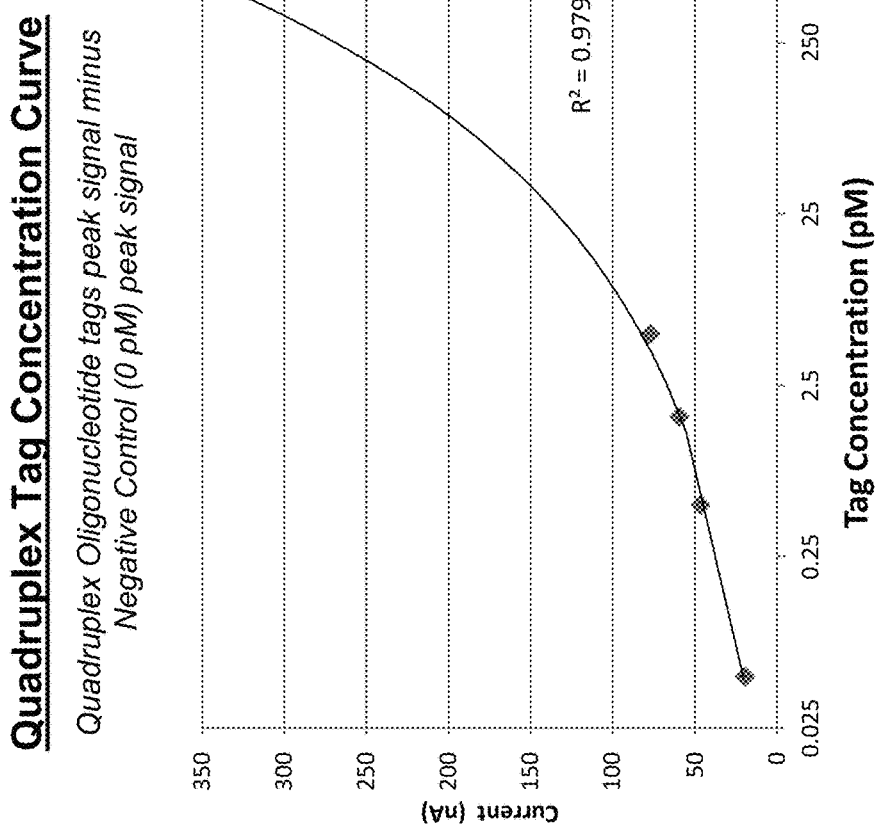
FIG. 4B is a graph of Current vs. Tag Concentration.
Figure 4A:
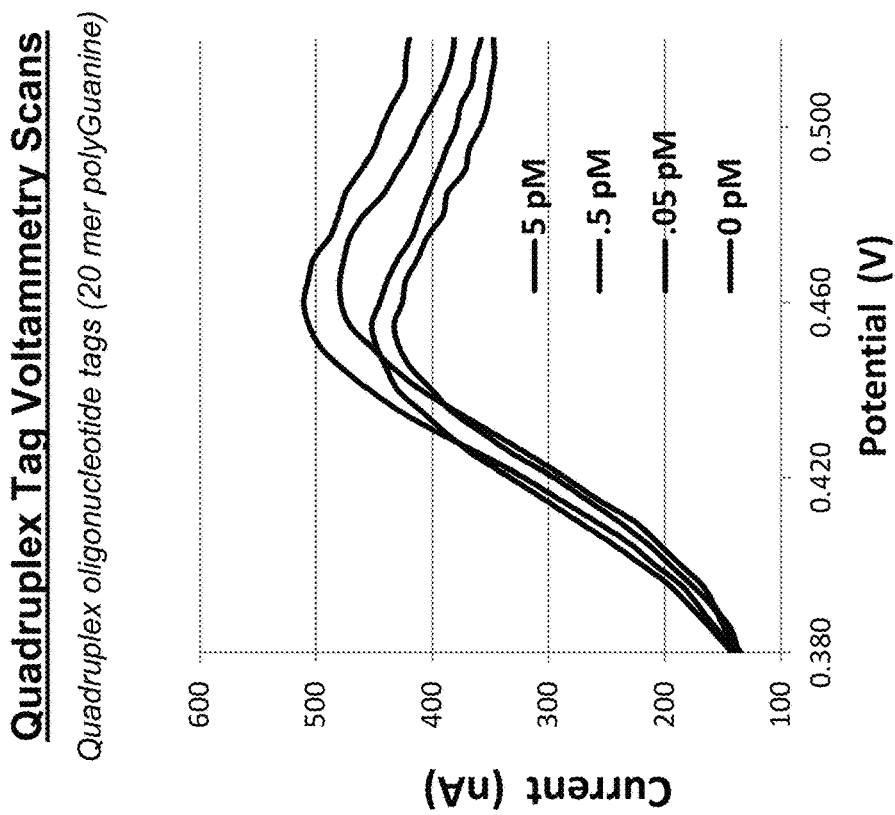
FIG. 4A is a graph of Current vs. Potential for different concentrations of electrochemically detectable tags.

Referring to FIG. 4B, the analyte signals for different tag concentrations are plotted and create a concentration curve with an R2 of 0.9799. This can use used to predict tags and analyte concentrations from unknown samples. A net signal is calculated as the peak current from an unknown sample minus the peak from the negative control. For example a net signal of 100 nA corresponds to about 20 pM of analyte.

Figure 8:
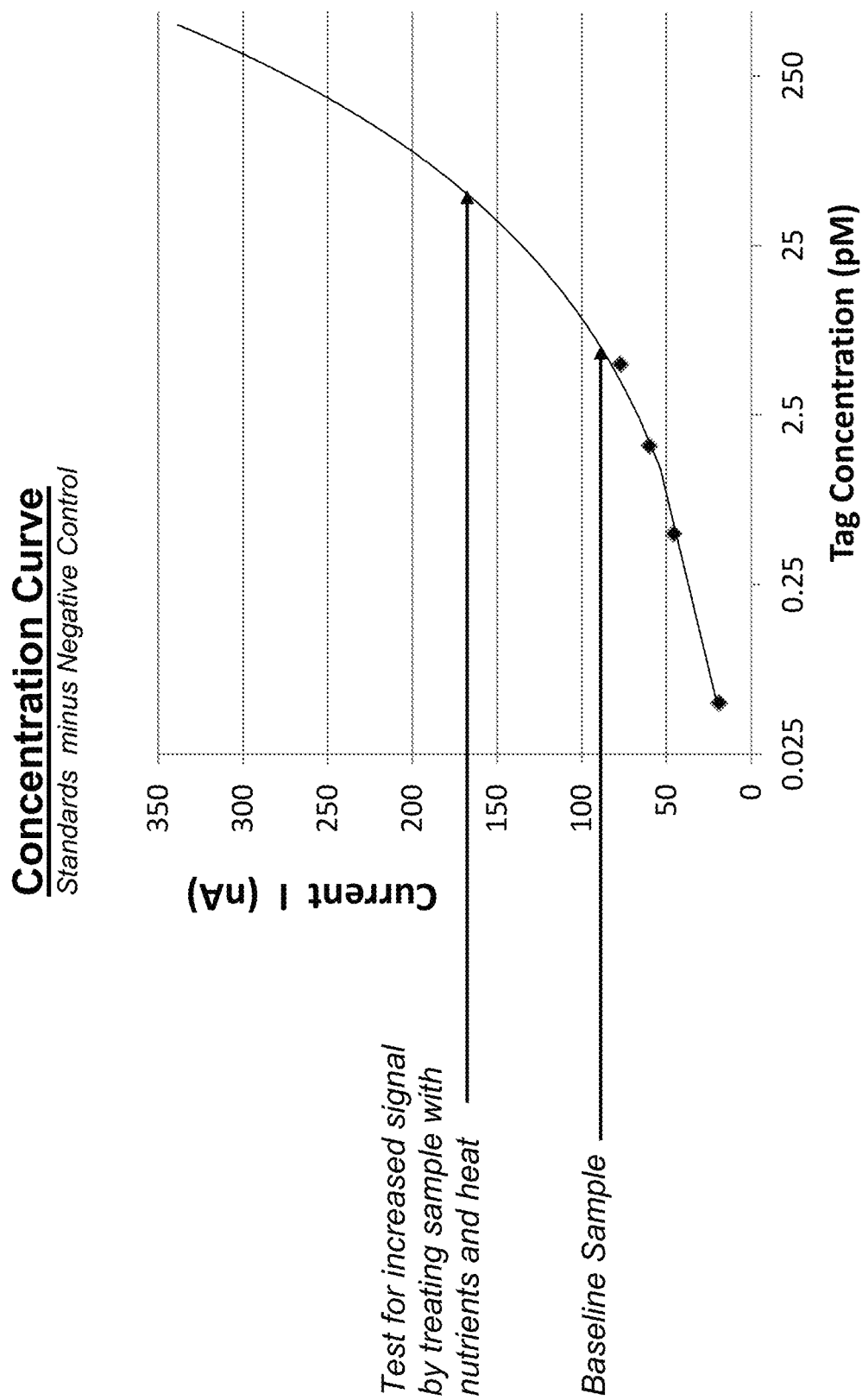
FIG. 8 is a graph of Current vs. Tag Concentration for a baseline sample and a sample treated with nutrients and heat that allow viable pathogens to replicate.

As known by one skilled in the art, FIG. 3B corresponds to the steps of a sandwich ELISA which has been modified with the invention's electrochemically detectable tags, methods and devices for detecting and/or quantifying extremely low levels of one or more target analytes in a fluid sample. In another embodiment, the steps performed sequentially for providing a fluid sample, analytes, single-stranded electrochemically detectable oligonucleotide tags, ligands, and particles correspond with the steps performed sequentially in a direct ELISA, an indirect ELISA, a sandwich ELISA, and a competitive ELISA. In another embodiment of the invention, two samples are taken from the same source to determine if a certain microorganism is present in the source, and if so, is available and can reproduce. One of the samples, referred to the baseline sample, is tested immediately with the method in FIGS. 3A and 8 to determine the electrochemical signal associated with microorganism concentration. The second sample is incubated with nutrients and heat for about 6 reproduction cycles. For example if the microorganism is *E. coli* O157:H7 which duplicates every 15 minutes, then the time 6 reproduction cycles would be about 1.5 hours to determine viability, which is much shorter than the 24 hours typically used in culture tests.

Detection Device

Figure 9:
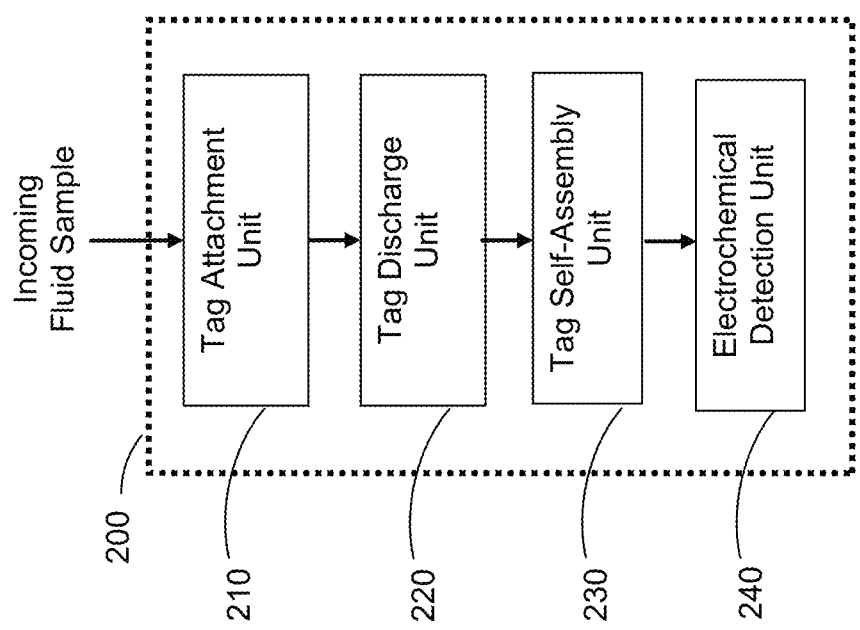
FIG. 9 is a schematic representation of the main units of an analyte detection device according to an embodiment of the present invention.

With reference to FIG. 9, the main units are shown of a device 200 for detecting and/or quantifying the level of one or more target analytes in a fluid sample. The device first includes a tag attachment unit 210 configured to bind one or more single-stranded electrochemically detectable oligonucleotide tags directly to an analyte, or indirectly to an analyte using a ligand, or indirectly to an analyte using a particle, if said analyte is present in a fluid sample. An incoming fluid sample that may contain non-specific materials and one or more analytes is separated into an outgoing target analyte with single-stranded tags condensate and a non-specific waste solution containing non-specific materials that could interfere with detection or cause false detection outcomes. The tag attachment unit may also comprise a magnet for magnetically extracting said complexes if the embodiment used magnetic separation.

The device also includes a tag discharge unit 220 comprising a system for unbinding the single-stranded electrochemically detectable oligonucleotide tags from the analytes. An incoming target analyte with single-stranded tag condensate the electrochemically detectable tags is separated into a single-stranded tag condensate containing the released tags and a waste solution containing debris. The device next includes tag self-assembly unit 230 configured to enable single-stranded electrochemically detectable oligonucleotide tags to self-assemble into quadruplex electrochemically detectable oligonucleotide by providing monovalent cations that enable quadruplex formation. The device further includes an electrochemical detection unit 240 with at least one biosensor working electrode configured to measure detection signals from the quadruplex electrochemically detectable oligonucleotide tags.

Electrochemical Detection Unit

Figure 10:
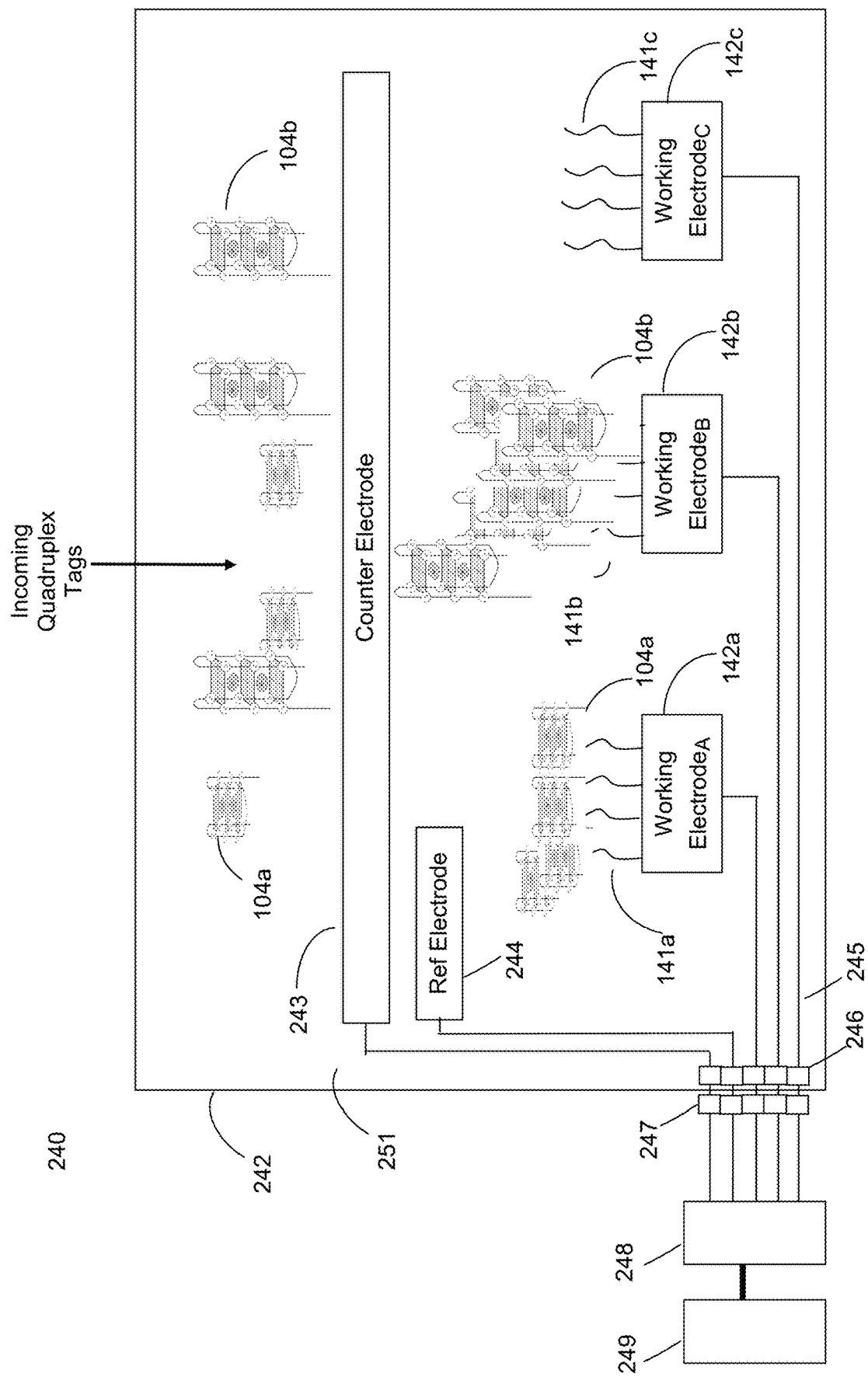
FIG. 10 is a schematic representation of an electrochemical biosensor according to one embodiment of the invention.
Figure 11:
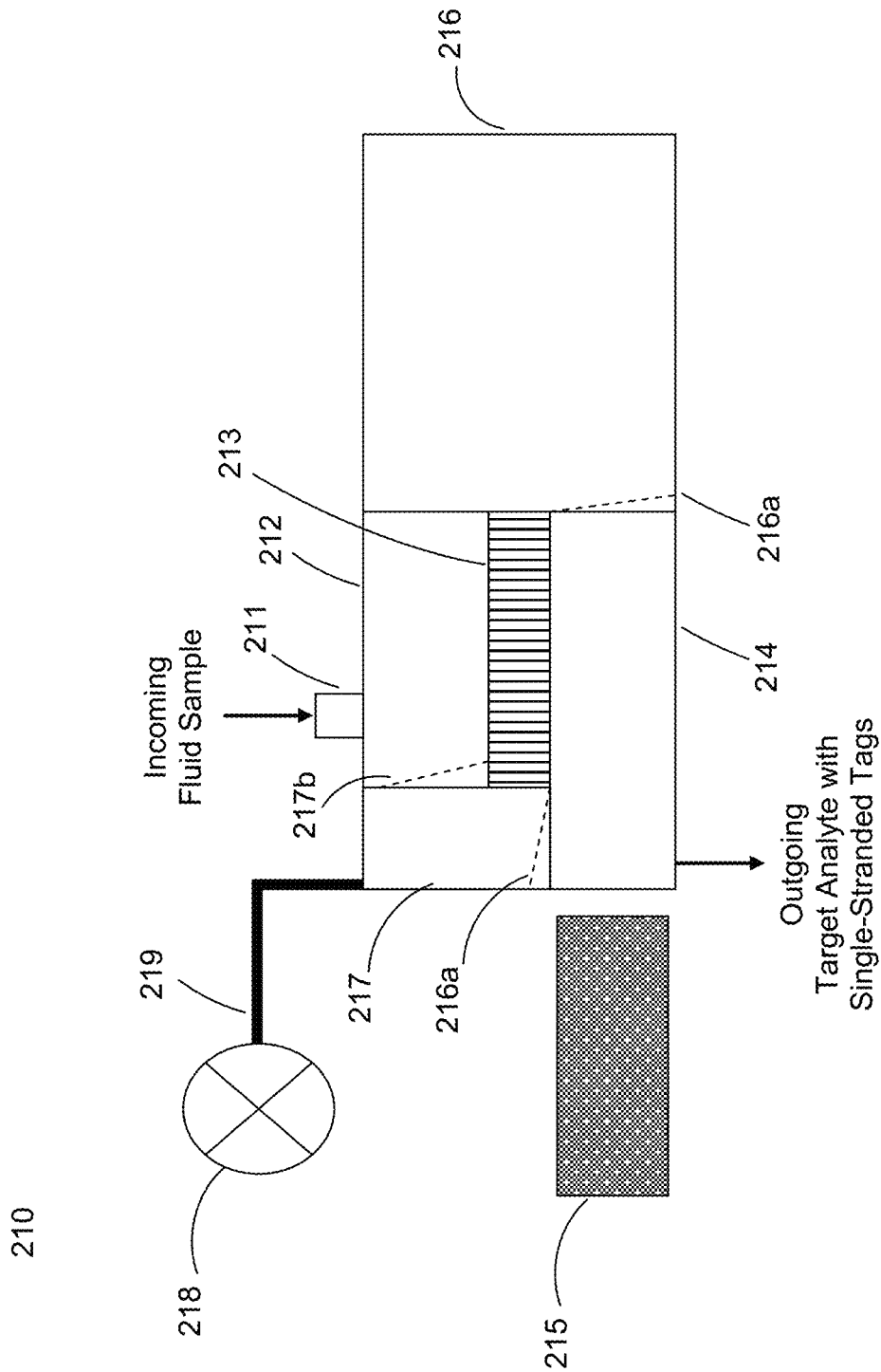
FIG. 11 is a schematic representation of a tag attachment unit according to one embodiment of the invention.
Figure 12:
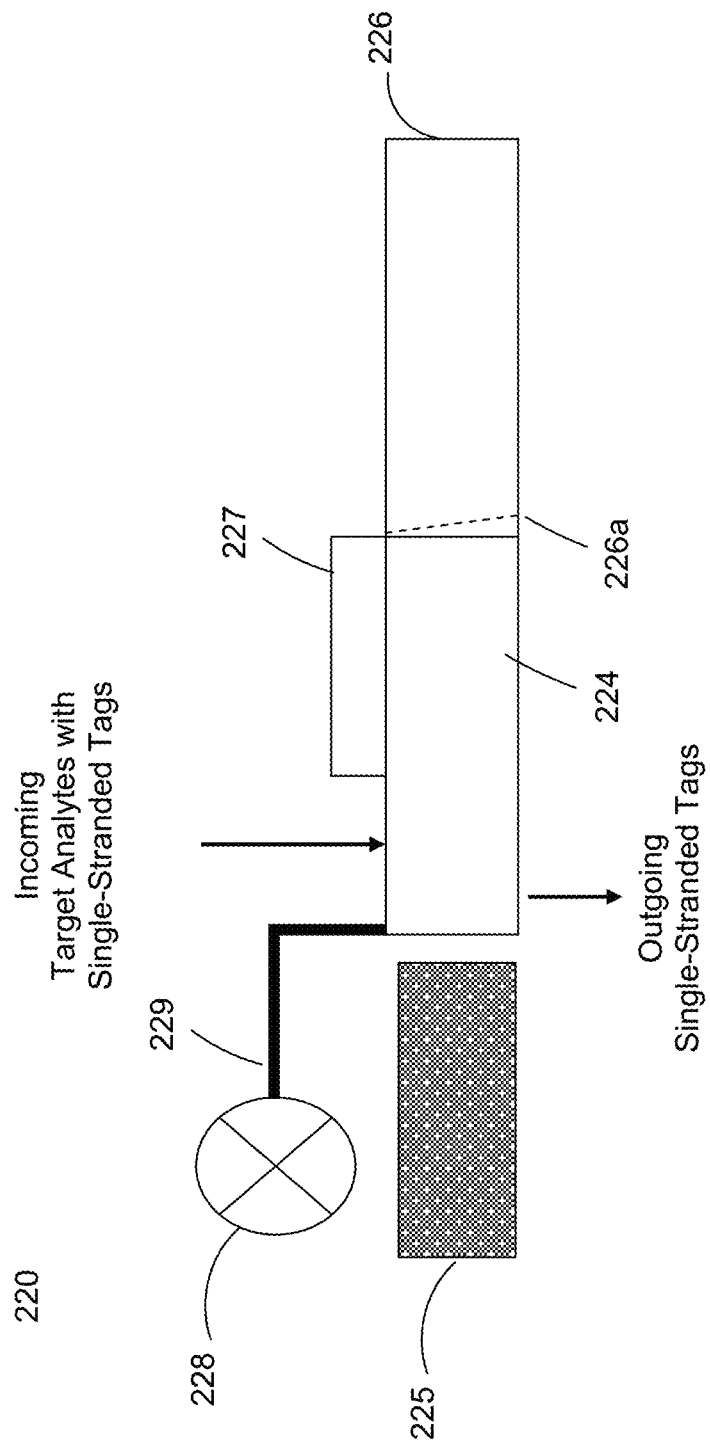
FIG. 12 is a schematic representation of a tag discharge unit according to one embodiment of the invention.
Figure 13:
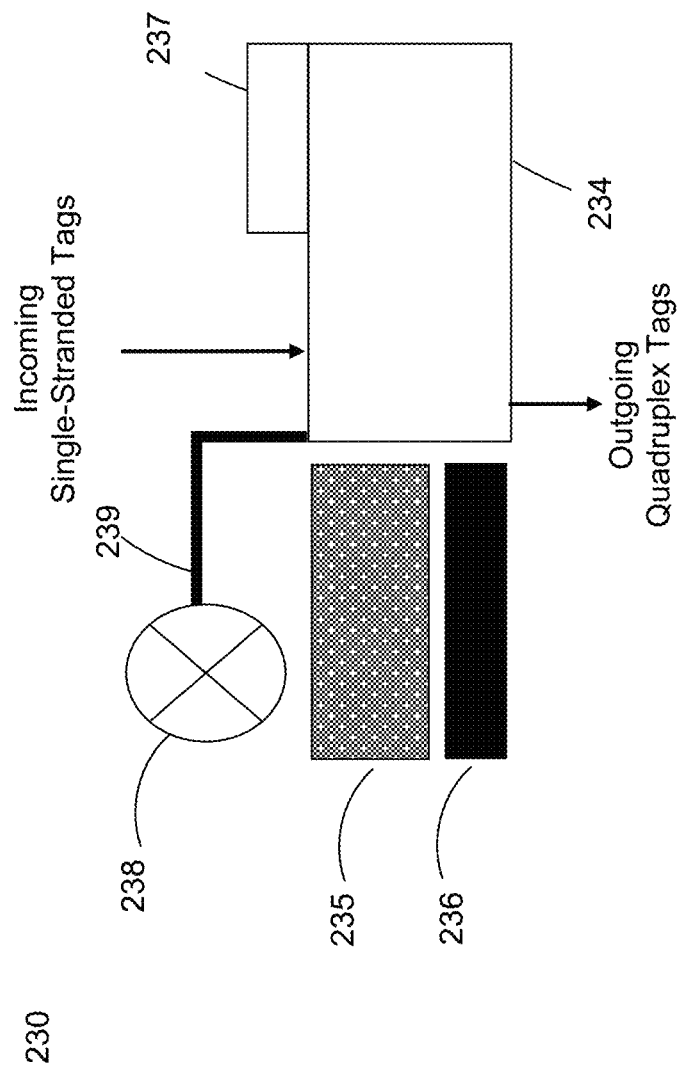
FIG. 13 is a schematic representation of a tag self-assembly unit according to one embodiment of the invention.

With reference to FIG. 10, there is shown an electrochemical detection unit 240 according to an embodiment of the invention. The incoming quadruplex electrochemically detectable tag condensate fills an enclosed mixing chamber 242 containing one or more working electrodes 142. In an example of one embodiment there are 3 working electrodes 142a, 142b, 142c corresponding with three target analytes: analyte A 101a, analyte B 101b, and analyte C 101c. The electrochemical detection unit further provides one or more sets of recognition probes attached to the surface of one or more working electrodes. In the above embodiment, each of the three working electrodes contains a set of recognition probes 141a, 141b, 141c bound to the working electrode surfaces 142a, 142b, 142c. Each set of recognition probes can hybridize with its complementary quadruplex electrochemically detectable tags 104a, 104b, 104c, should said tags be present in the incoming amplified tag condensate. Complementary tags and probes form tag-probe complexes that become immobilized near the surface of the working electrodes.

Figure 14:
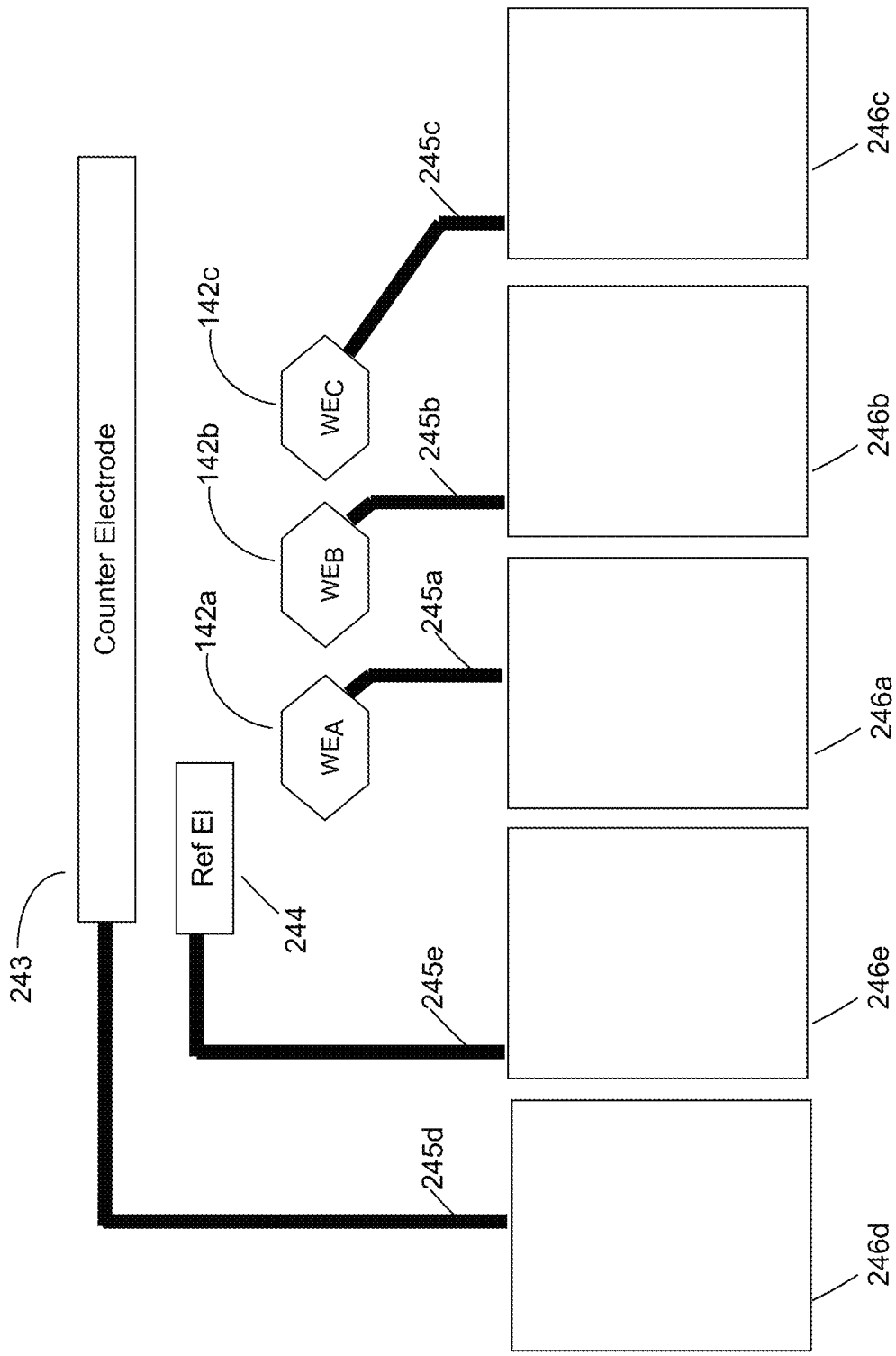
FIG. 14 is a schematic representation of an electrochemical biosensor according to one embodiment of the invention.

The electrochemical detection unit further provides at least one counter electrode 243 and one reference electrode 244 which are used to facilitate electrochemical detection as is known to those skilled in the art. The electrochemical detection unit also provides electronic circuitry 245 that electrically connect each electrode to corresponding connection pads 246. Referring to FIG. 14, an embodiment can contain the working electrodes, counter electrode, reference electrode, electronic circuitry and connector pads as an independent biosensor. In one embodiment there can be one or multiple biosensors contained in an electrochemical detection unit.

Referring to FIG. 10, the connector pads 246 can physically and electrically connect to corresponding connection pads 247. The connection pads 247 are needed to electrically attach the electrochemical detection unit and/or biosensor to a potentiostat 248 or other instrument that can generate an electrical source such as potential to the electrochemical detection unit and measure the resulting electrical signal, such as current that is provided if guanine or other redox materials oxidize. The potentiostat is connected to other apparatuses 249 that may be needed to support the electrochemical detection unit as will be described below. Other electrochemical techniques and configurations can be supported as would be obvious to those skilled in the art.

Another unique aspect of this invention is the ability to support different types of biosensors. Referring to FIG. 15A, in one embodiment, the working electrode 142 is a solid conductive structure fabricated into a non-conductive or semi-conductive base 261 as is commonly used in a low-cost disposable glucose test strip. In this embodiment the surface area can be approximately $10^{-2}$ cm$^2$. Recognition probes 141 are bound to the working electrode surface to facilitate hybridization with electrochemically detectable tags. The benefit of this biosensor is its low cost and may have adequate sensitivity should the amplification method provide a sufficient amplified level of detectable tags.

Figure 15B:
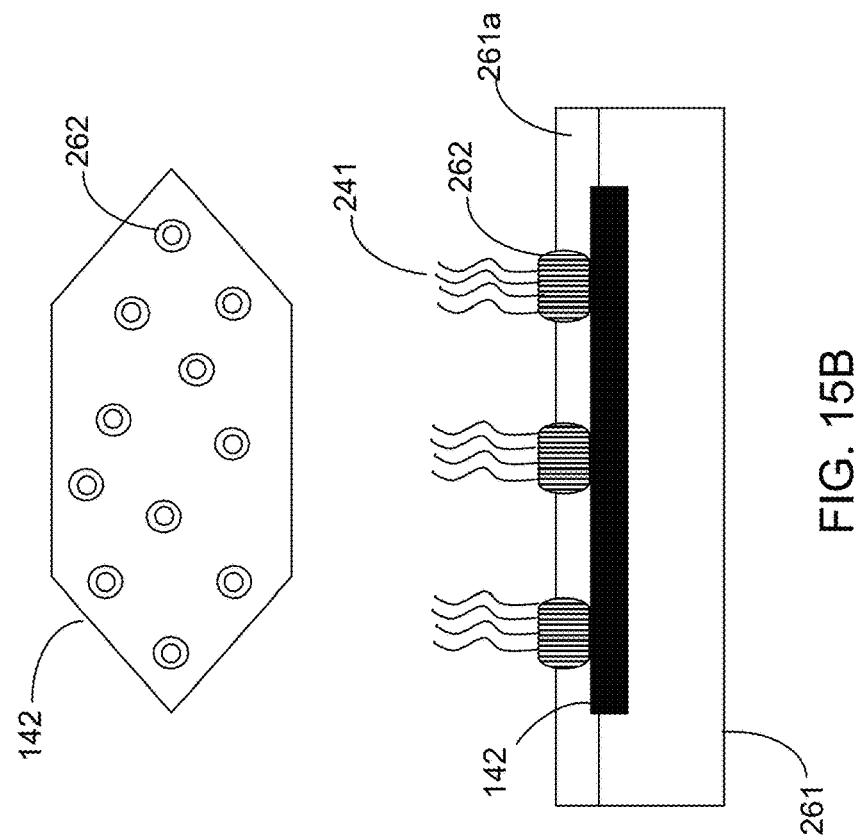
FIG. 15B is a schematic representations of an electrochemical biosensor with a low density of microscale structures.
Figure 15A:
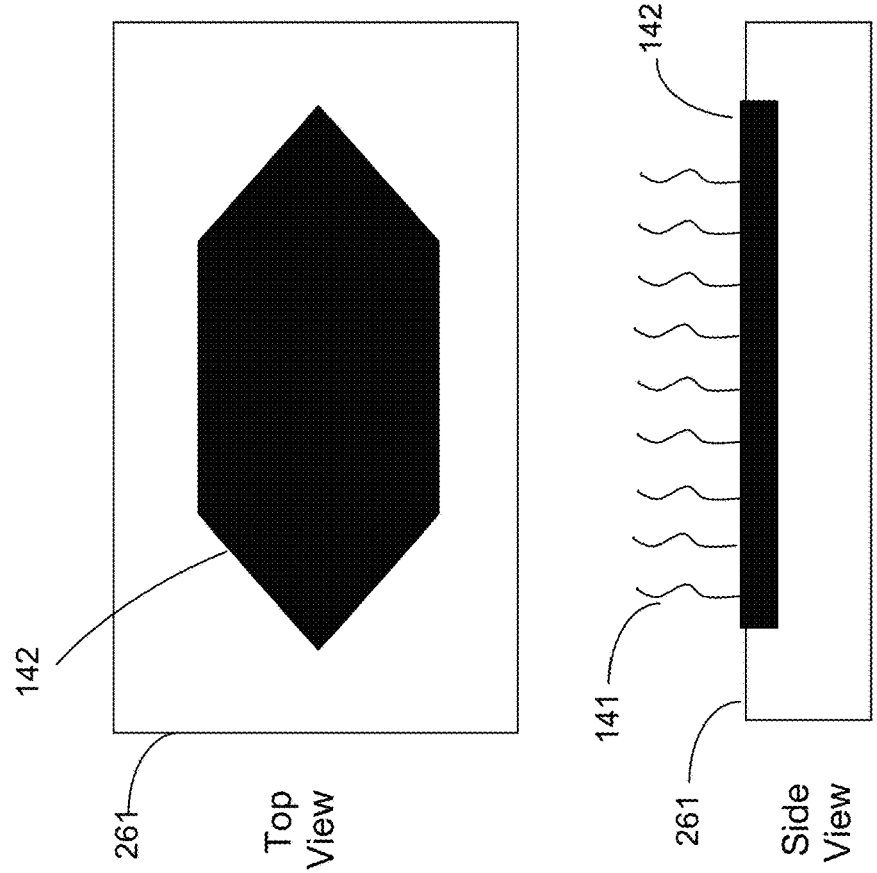
FIG. 15A is a schematic representations of an electrochemical biosensor with a solid electrode surface.

Referring to FIG. 15B, in another embodiment, the working electrode 142 is a microscale structure electrode surface comprising a low density plurality of electrically conductive microscale structures 262 fabricated on an electrode surface 142. Each microscale structure is encapsulated on its side walls with a non-conductive material 261a. The volume between each microscale structure is filled with said non-conductive material, leaving the tips of the microscale structure as the only exposed portions of the working electrode. This reduces the active surface area of the working electrode to the area of the exposed tips of said microscale structures, which is much smaller than the underlying working electrode. The improved signal-to-noise resolution provides an improved detection limit for the biosensor. The benefit of this biosensor is a greater sensitivity than the solid working electrode in FIG. 15A and can be employed when an improved detection level is desirable, at a slightly higher cost per sensor. Other types of biosensors can also be supported.

Other Configurations

The above invention can also take the form of other configurations that provide beneficial aspects for particular applications. In some embodiments some or all of the reagents and beads can stored in a central location of the analyzer and added to the cartridge or panel as required.

Point of Care/Point of Use Device

Figure 16:
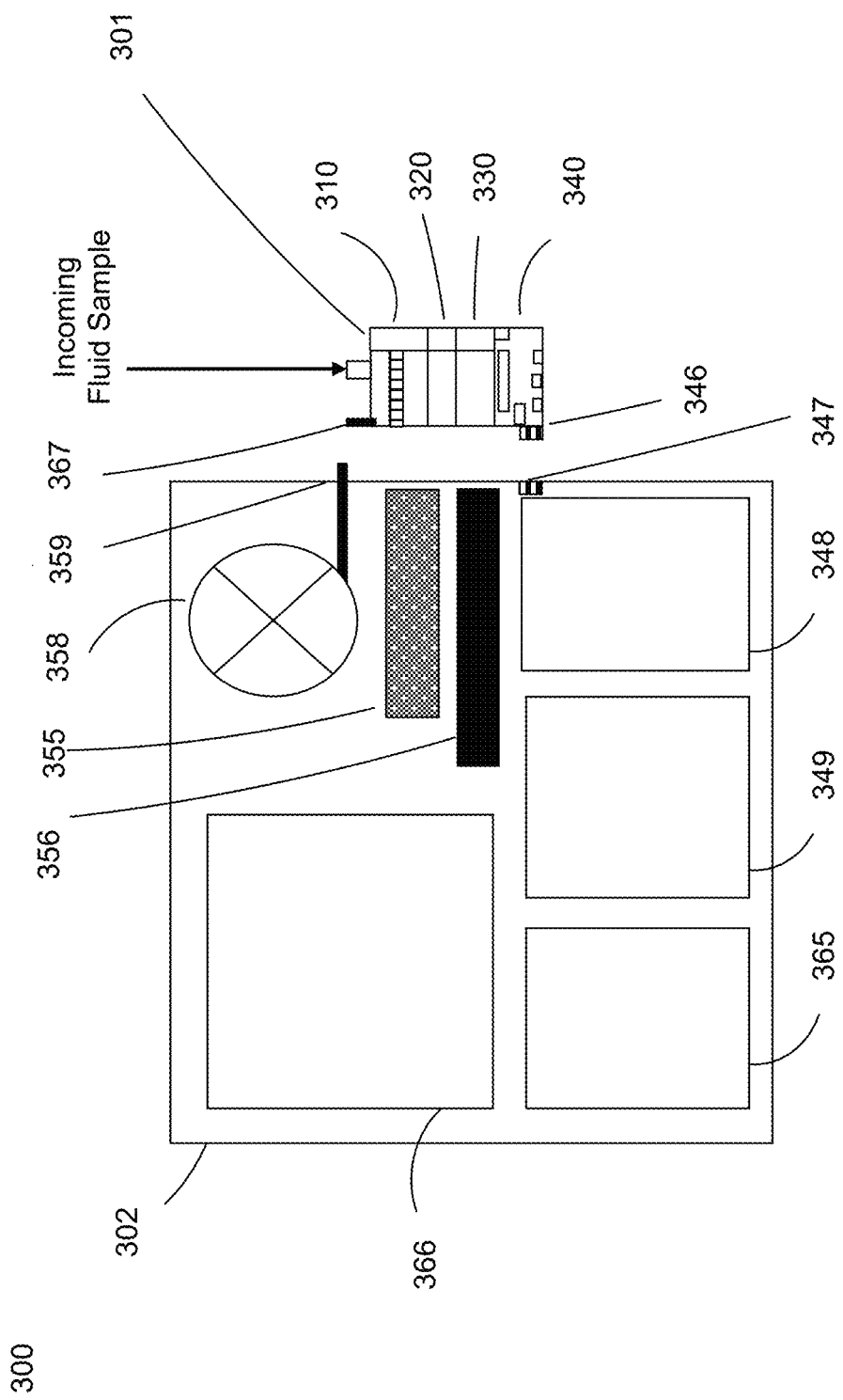
FIG. 16 is a schematic representation of a point of care/point of use analyte analyzer and consumable test cartridge according to one embodiment of the invention.

With reference to FIG. 16, the main units are shown of a point of care/point of use device 300 for detecting and/or quantifying the level of one or more target analytes in a fluid sample according to an embodiment of the invention. The device first includes a consumable test cartridge 301 that consolidates all of the non-reusable portions of the above-mentioned device 200 which are required to process a fluid sample. Said cartridge comprises a tag attachment compartment 310, a tag discharge compartment 320, a tag discharge compartment 330, and an electrochemical detection compartment 340. The tag attachment compartment 310 is configured to bind one or more single-stranded electrochemically detectable oligonucleotide tags directly to an analyte, or indirectly to an analyte using a ligand, or indirectly to an analyte using a particle, if said analyte is present in a fluid sample. The tag discharge compartment 320 is configured to unbind single-stranded electrochemically detectable oligonucleotide tags from the analytes. The tag self-assembly compartment 330 is configured to enable single-stranded electrochemically detectable oligonucleotide tags to self-assemble into quadruplex electrochemically detectable oligonucleotide by providing monovalent cations that enable quadruplex formation, and the electrochemical detection compartment 340 with at least one biosensor working electrode is configured to measure detection signals from the quadruplex electrochemically detectable oligonucleotide tags. The device next includes an analyzer 302 that consolidates all reusable portions of the abovementioned device 200 which are required to operate a consumable test cartridge 301 for processing a test sample. Said analyzer provides a mechanical system 358 with a mechanical connector 359 that connects to the cartridge connector 367, a magnet 355 if magnetic separation is used, and a tag release system 356 which may include a heater. The analyzer further provides an electrochemical signal generation and signal measurement system 348 with electrical connection 347 to the cartridge connector 346. The analyzer further provides other systems to support the operations, which may include a central processing unit 349, a power supply 365, and a user interface 366.

Low Volume Device

Figure 17:
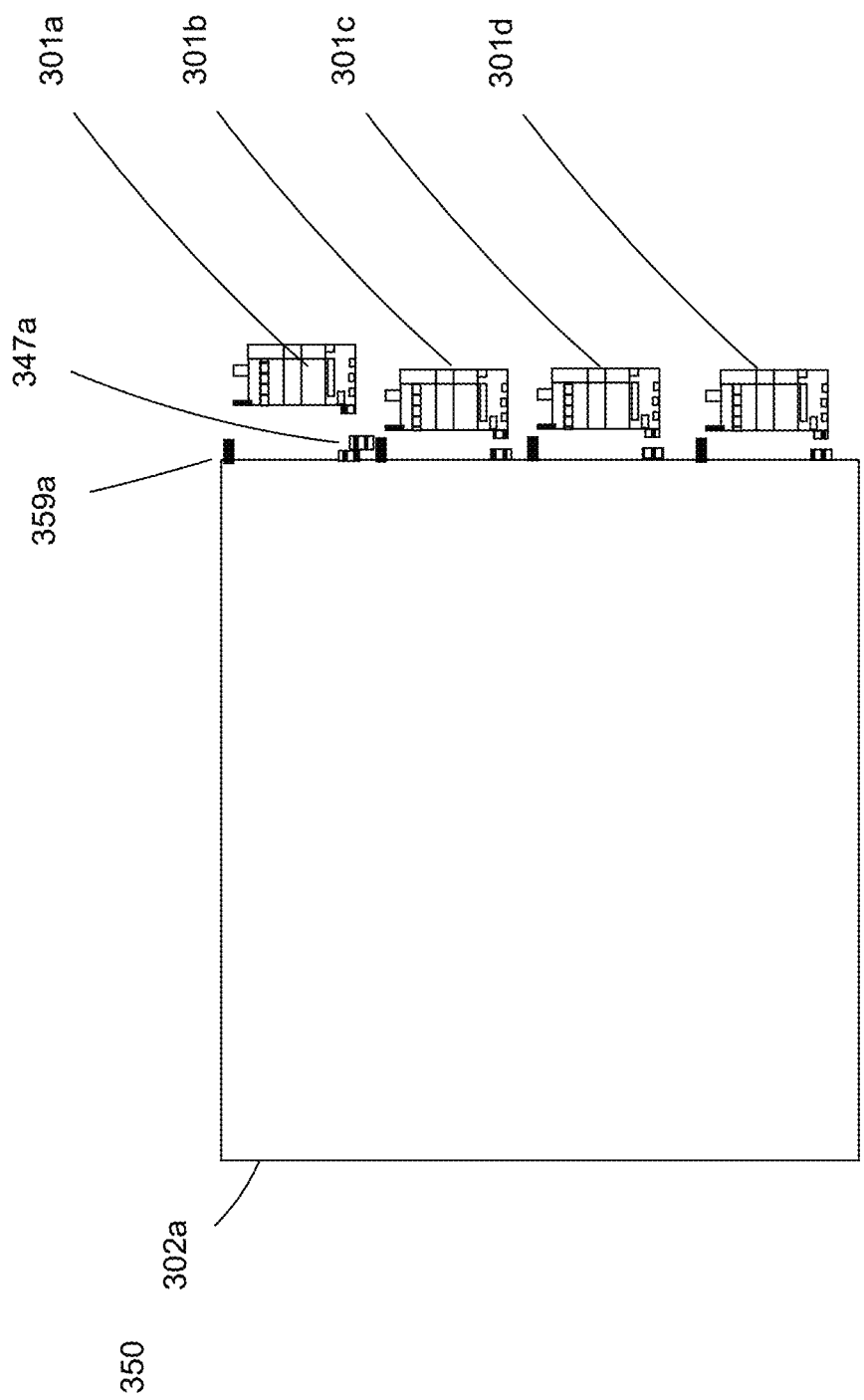
FIG. 17 is a schematic representation of a low volume analyte analyzer that can process one or more consumable test cartridges according to one embodiment of the invention.

With reference to FIG. 17, the main units are shown of a low volume device 350 for detecting and/or quantifying the level of one or more target analytes in one or more fluid samples according to an embodiment of the invention. The device first includes one or more consumable test cartridges 301a, 301b, 301c, 301d, . . . that consolidate all non-reusable portions of the abovementioned device 200 which are required to process a fluid sample. Each cartridge comprises a tag attachment compartment, a tag discharge compartment, a tag discharge compartment, and an electrochemical detection compartment. The device next includes an analyzer 302a that consolidates all reusable portions of the abovementioned device 200 which are required to simultaneously operate one or more consumable test cartridges 301a, 301b, 301c, 301d, . . . for processing one or more test samples. Said analyzer provides one or more mechanical systems with mechanical connectors 359a, . . . that connect to the cartridge connectors, magnet, and tag release system which includes a heater. The analyzer further provides one or more electrochemical signal generation and signal measurement system with electrical connections 347a, . . . to the cartridge connectors. The analyzer further provides other systems to support the operations, which may include a central processing unit, power supply, and user interface.

High Throughput Device

Figure 18:
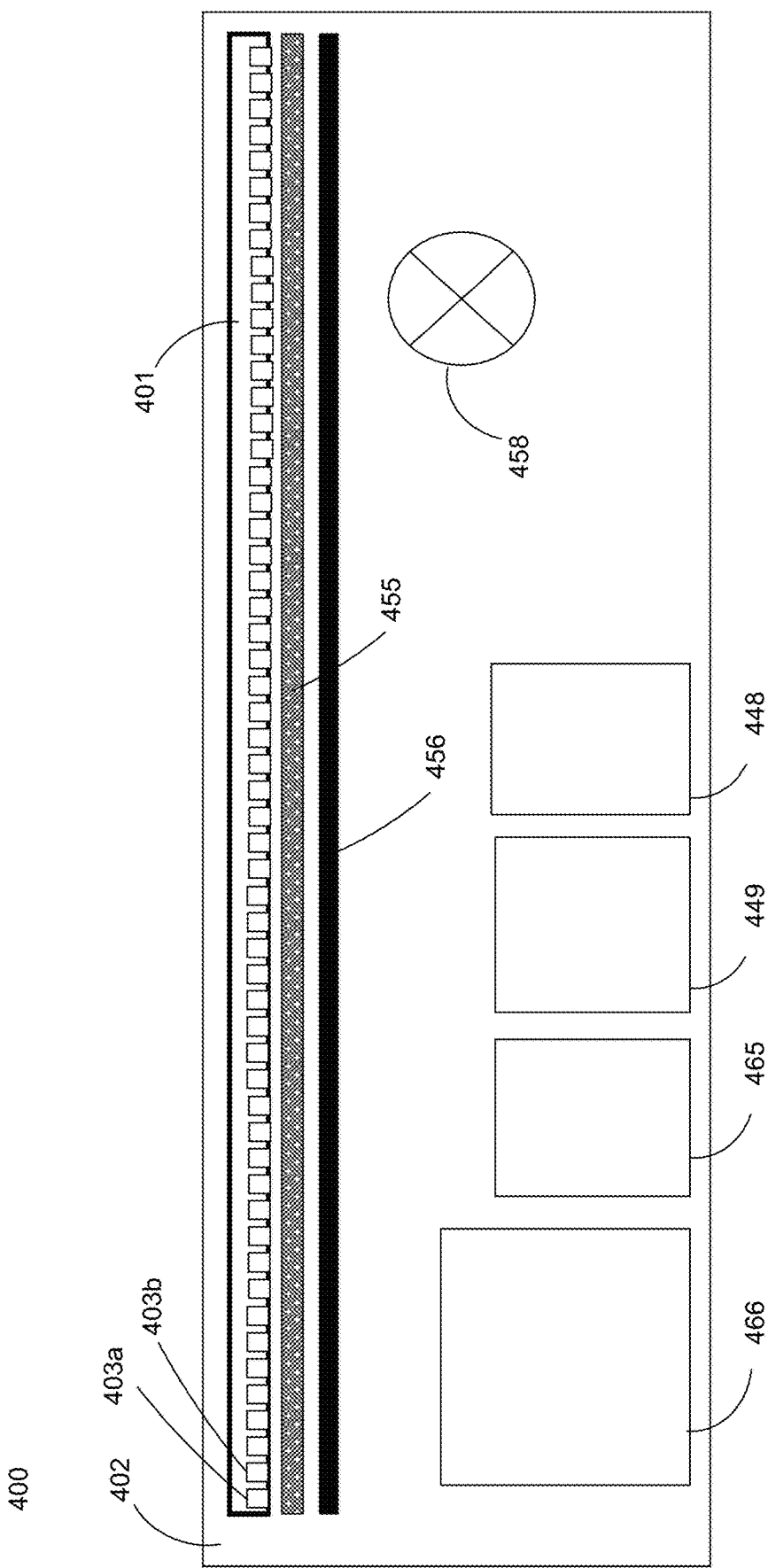
FIG. 18 is a schematic representation of a high throughput analyte analyzer and high throughput test panel according to one embodiment of the invention.

With reference to FIG. 18, the main units are shown of a high throughput device 400 for detecting and/or quantifying the level of one or more target analytes in a plurality of fluid samples according to an embodiment of the invention. The device first includes a high throughput test panel 401 comprising a plurality of wells 403a, 403b, . . . that consolidate all non-reusable portions of the abovementioned device 200 which are required to process a fluid sample. Each well comprises a tag attachment compartment, a tag discharge compartment, a tag discharge compartment, and an electrochemical detection compartment. The tag attachment compartment is configured to bind one or more single-stranded electrochemically detectable oligonucleotide tags directly to an analyte, or indirectly to an analyte using a ligand, or indirectly to an analyte using a particle, if said analyte is present in a fluid sample. The tag discharge compartment is configured to unbind single-stranded electrochemically detectable oligonucleotide tags from the analytes. The tag self-assembly compartment is configured to enable single-stranded electrochemically detectable oligonucleotide tags to self-assemble into quadruplex electrochemically detectable oligonucleotide by providing monovalent cations that enable quadruplex formation, and the electrochemical detection compartment with at least one biosensor working electrode is configured to measure detection signals from the quadruplex electrochemically detectable oligonucleotide tags. The device next includes a high throughput analyzer 402 that consolidates all reusable portions of the abovementioned device 200 which are required to operate a high throughput test panel 401 comprising a plurality of wells 403a, 403b, . . . for processing test samples. Said analyzer provides one or more mechanical systems 458 that connect to the wells, a magnet 455, and tag release system which may include one or more heater 456. The analyzer further provides one or more electrochemical signal generation and signal measurement system 448 with electrical connections to the wells. The analyzer further provides other systems to support the operations, which may include one or more central processing unit 449, power supply 465, and user interface 466.

Autonomous Networked Device

Figure 19:
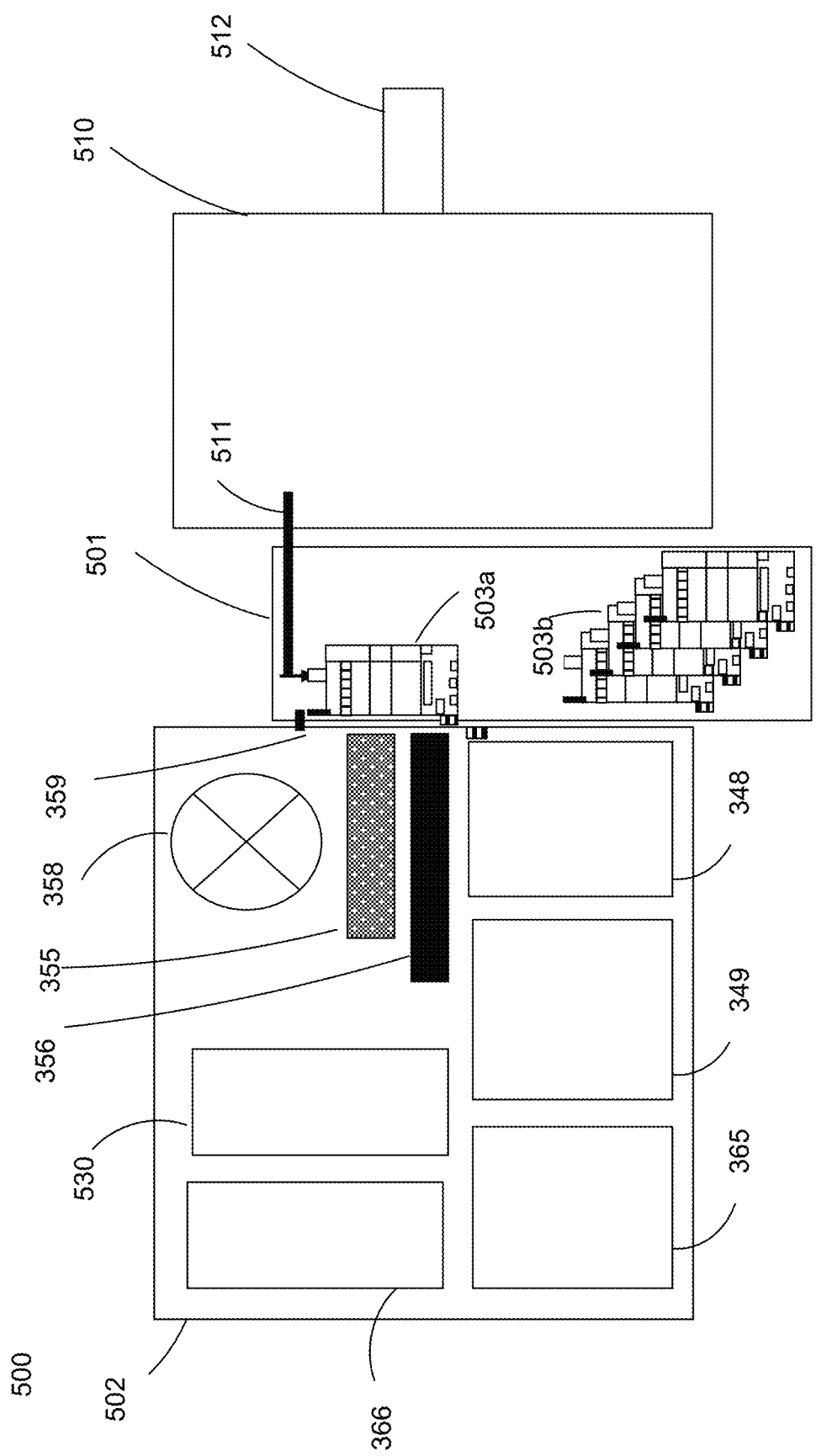
FIG. 19 is a schematic representation of an autonomous networked analyzer, consumable test cartridges, and sample collection and concentration unit according to one embodiment of the invention.

With reference to FIG. 19, the main units are shown of an autonomous networked device 500 capable of integrating with an automated sampling and concentration instrument to remotely analyze field samples without a technician in an autonomous networked application for detecting and/or quantifying the level of one or more target analytes in a fluid sample according to an embodiment of the invention. The device first includes a test cartridge assembly 501 that includes one or more test cartridges 503a, 503b, . . . that consolidate all non-reusable portions of the abovementioned device 200 which are required to process a fluid sample. Each cartridge comprises a tag attachment compartment, a tag discharge compartment, a tag discharge compartment, and an electrochemical detection compartment. The tag attachment compartment is configured to bind one or more single-stranded electrochemically detectable oligonucleotide tags directly to an analyte, or indirectly to an analyte using a ligand, or indirectly to an analyte using a particle, if said analyte is present in a fluid sample. The tag discharge compartment is configured to unbind single-stranded electrochemically detectable oligonucleotide tags from the analytes. The tag self-assembly compartment is configured to enable single-stranded electrochemically detectable oligonucleotide tags to self-assemble into quadruplex electrochemically detectable oligonucleotide by providing monovalent cations that enable quadruplex formation, and the electrochemical detection compartment with at least one biosensor working electrode is configured to measure detection signals from the quadruplex electrochemically detectable oligonucleotide tags.

The device next includes an analyzer 502 that consolidates all reusable portions of the abovementioned device 200 which are required to operate a consumable test cartridge 501 for processing a test sample. Said analyzer provides a mechanical system 358 with a mechanical connector 359 that connects to the cartridge connector, a magnet 355, and a tag release system 356 which includes a heater. The analyzer further provides an electrochemical signal generation and signal measurement system 348 with electrical connection to the cartridge connector. The analyzer further provides other systems to support the operations, which may include a central processing unit 349, a power supply 365, and a user interface 366. An optional communications capability 530 may be included in the analyzer 502 or as a separate unit to communicate test results and other information through wireless or wired communications. The device next includes a sample collection and concentration unit 510 that automatically samples and/or concentrates air, water, or other media through an input mechanism 512. Said sample collection and concentration unit delivers a processed and/or concentrated sample to the inlet 511 of an unused test cartridge 503.

Developer Kit

Figure 20B:
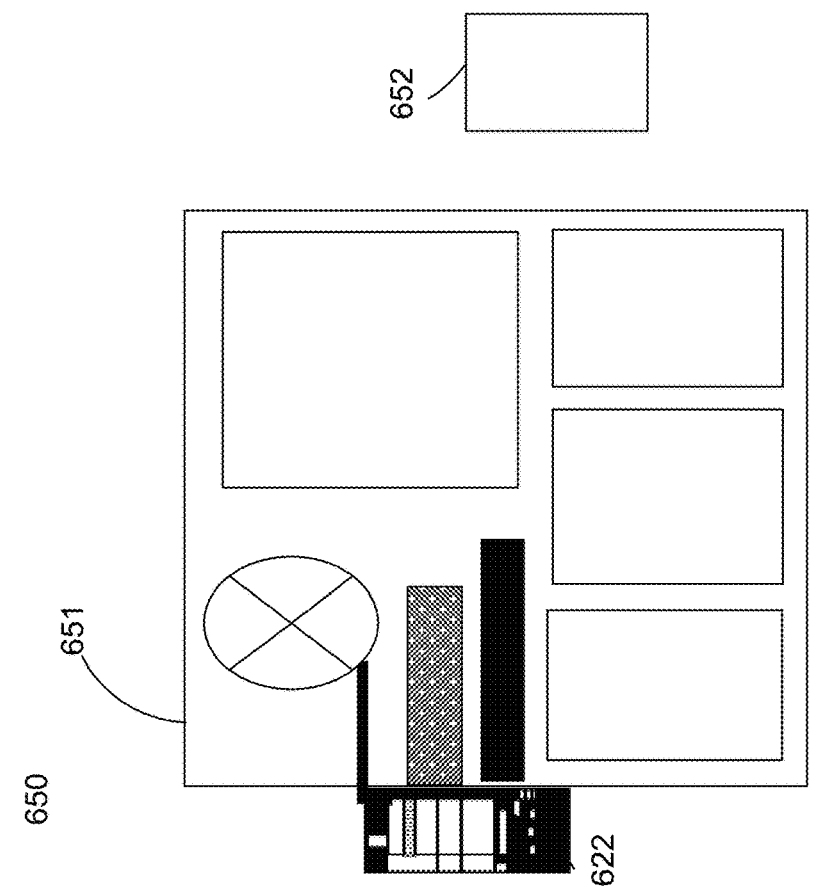
FIGS. 20A and 20B are a schematic representation of a developer kit according to one embodiment of the invention comprising a cartridge preparation instrument in FIG. 20A and a cartridge validation instrument in FIG. 20B.
Figure 20A:
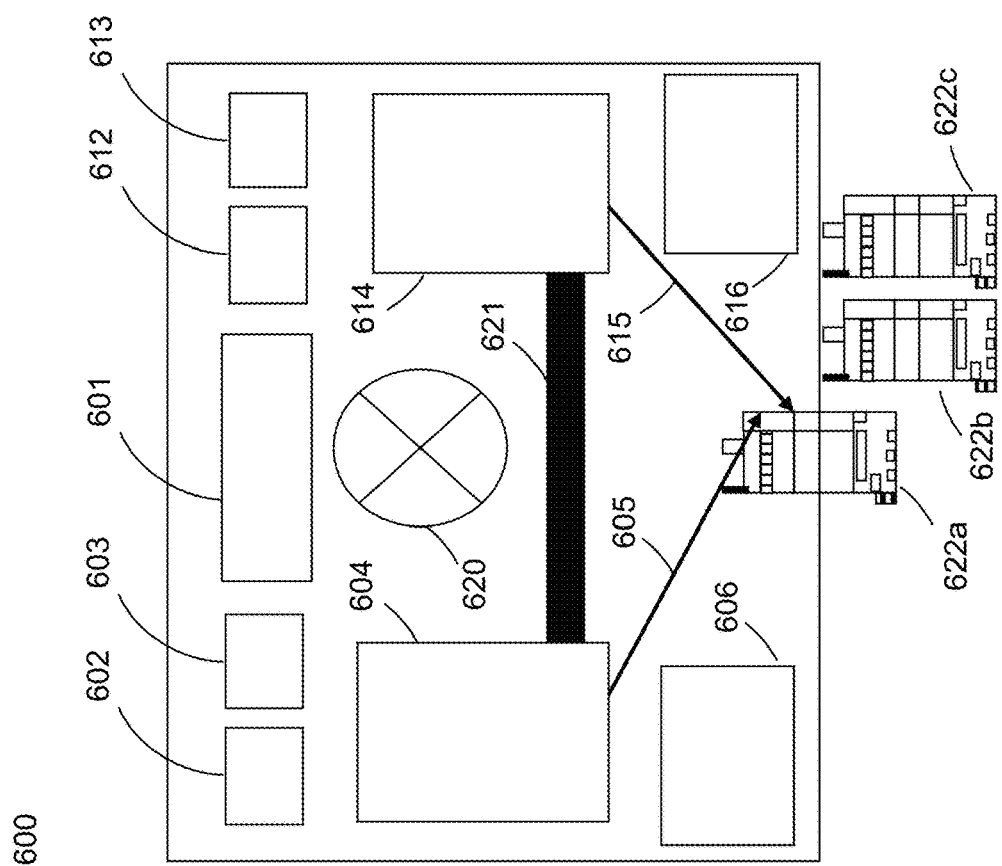

With reference to FIGS. 20A and 20B, the main units are shown of a developer kit for developing test cartridges and test panels for applications of the invention. The kit can be used for validating different antibodies, DNA probes, ligands and process protocols. The kit can also be used for producing low volume batches of test cartridges and test panels.

Referring to FIG. 20 in an embodiment, the tag attachment unit, the tag discharge unit, the tag self-assembly unit, and the electrochemical detection unit are configured to comprise: (a) one or more consumable development cartridges 622a . . . and 623, comprising portions of the device units for processing one or more samples; (b) a development analyzer 600 comprising portions of the device units for operating the one or more consumable development cartridges to process one or more samples; and (c) algorithms for measuring the effectiveness of analyte binding materials, tag elution, and tag-probe hybridization, algorithms for generating concentration curves, and algorithms for identifying information associated with specific consumable development cartridges. The consumable development cartridge 622 comprises one or more of microfluidics, a specimen inlet, reservoirs containing reagents, channels and mixing chambers, biosensors or nanobiosensors, heaters, magnet, valves, inlets for air connections, electrical connectors and circuitry for signal measurements and electrical systems, bar code, and Quick Response (QR) code.

The kit first includes a cartridge preparation instrument 600 that automates one or more standard protocols for conjugating antibodies and DNA probes to directly or indirectly to analytes such as the protocol used in the Pierce Direct Magnetic IP and Co-IP Kit (Thermo Fisher Scientific, Pierce Antibodies, Rockford, Ill.). The instrument comprises a reagent storage compartment 601, a single-stranded oligonucleotide tag storage compartment 602, an antibody or DNA probe storage compartment 603, and a preparation chamber 604. The antibodies or DNA probes to be validated are provided by the developer. Said instrument provides a mechanical system 620 and a heater 621. The instrument further provides other systems to support the various operations, which may include a central processing unit, power supply, and user interface. Once the conjugation protocol is completed, the single-stranded oligonucleotide tags are transferred out 605 of the preparation chamber 604 and inserted into a portion of a developer kit test cartridge 622a. The instrument further comprises a tag attachment compartment 612, a tag discharge compartment 613, a tag discharge compartment 614, and an electrochemical detection compartment.

Once the conjugation single-stranded oligonucleotide tag binding protocol is completed, the conjugated single-stranded oligonucleotide tags are transferred out 615 of the preparation chamber 614 and inserted into a portion of a developer kit test cartridge 622a. After the conjugated single-stranded oligonucleotide tags are inserted, the developer kit test cartridge 622a would be sealed, have an identification code printed on its surface and be ready for validation testing as a developer kit validation cartridge 623. In applications which require multiplexing, there would be sets of single-stranded oligonucleotide tags required for each target analyte. The instrument further reagent storage compartment 606 and a single-stranded oligonucleotide tag storage compartment 616 to temporarily store conjugated single-stranded oligonucleotide tags while other sets are being separately conjugated. Once all of the sets are conjugated they could be inserted into the appropriate portion of a developer kit test cartridge 622a. As would be understood by those skilled in the art, the cartridge preparation instrument 600 can be configured to produce a plurality of developer kit test cartridges 622a, 622b, 622c, . . . in the same batch. The instrument 600 can further be configured to prepare and transfer conjugated magnetic particles and conjugated nonmagnetic particles to a high throughput test panel 401.

The developer kit 600 next includes a cartridge validation instrument 651 that consolidates all reusable portions of the abovementioned device 200 which are required to operate one or more consumable test cartridge 301, or developer kit validation cartridge 623 for processing a test sample. Said instrument provides one or more mechanical systems with mechanical connectors that connect to the cartridge connectors, magnet, and tag release system which includes a heater. The instrument further provides one or more electrochemical signal generation and signal measurement system with electrical connections to the cartridge connectors. The instrument further provides other systems to support the operations, which may include a central processing unit, power supply, and user interface. The instrument also further provides software 652 that allows a developer to select and configure the process protocols to process the sample, that analyzes test data and generates statistical test results for the developer, and that produces standard curves.

EXAMPLES

In order that this invention may be better understood, the following examples are set forth. These examples are provided solely for the purpose of further illustrating certain specific aspects and embodiments of the invention. Although embodiments of the invention have been disclosed for illustrative purposes, those skilled in the art will appreciate that various modifications, additions and substitutions are possible, without departing from the scope of the invention as herein described, and all are included within the scope of the invention.

Example 1

Sandwich ELISA with Electrochemically Detectable Oligonucleotide Tags

As an example of an embodiment of this invention, test samples were evaluated for low levels of *Cryptosporidium parvum* oocysts in drinking water. In 1993 Milwaukee experienced the largest documented drinking water outbreak in US history caused by the chlorine-resistant parasite Cryptosporidium parvum, which sickened over 400,000 people and killed 100, mostly HIV/AIDS patients. Low level detection is important because cryptosporidium has an infective dose as low as 10 oocysts/mL which is below the detection limit of most assays. In this example, reagents were procured in advance of the experiments including ELISA microtiter wells coated with anti-cryptosporidium antibodies to capture the analytes and a BSA blocking agent to block potential binding sites from non-specific materials. 1-micron polystyrene microparticles (PB) were conjugated with single-stranded electrochemically detectable oligonucleotide tags (20-mer PolyG), and also with anti-cryptosporidium antibodies using biotin-streptavidin chemistry. Other reagents and equipment included PBS wash buffer, 80 mM NaOAc (pH 9) with 95% formamide elution buffer to supply Na+ cations, microtiter rotator, and microtiter with screen-printed carbon electrodes. A summary of the protocol is in Table 9.

TABLE 9

Protocol Summary for Sandwich ELISA with Electrochemically Detectable Oligonucleotide Tags

| Sandwich Creation | Tag Elution and Self Assembly | Tag Measurement and Analyte Concentration |
|---|---|---|
| Attach Tags in Sandwiches<br>1. Add 100 μL sample to microtiter well coated with capture antibodies and incubate for 30 minutes<br>2. Add 1,000,000 PB conjugated with single-stranded oligonucleotide tags and antibodies and incubate for 30 minutes<br>3. Wash with PBS wash buffer (to Step 4) | Elute Tags<br>4. Add 250 μL of 80 mM NaOAc (pH 9) with 95% formamide elution buffer and apply 90° C. heat for 10 min to enable self-assembly<br>5. Remove supernatant and transfer to biosensor (to Step 6) | Quantify Analytes<br>6. Adsorb tags in supernatant to biosensor<br>7. Apply SWV (1,400 mV/s)<br>8. Measure sample peak amplitude<br>9. Compare sample amplitude vs. concentration standards to determine concentration |

A 100 μL sample is placed in a microtiter well coated with anti-cryptosporidium antibodies and 200 μL PBS buffer is added. The contents are incubated for 30 minutes to allow the cryptosporidium analytes to bind with the antibodies. The supernatant is discarded and the well is washed with PBS wash buffer to leave the cryptosporidium-antibody complexes in the well. Next, a solution containing 1,000,000 (10 μL) polystyrene microbeads (PB) pre-conjugated with coated with anti-cryptosporidium antibodies and single-stranded electrochemically detectable oligonucleotides is added to the well along with 200 μL PBS buffer. The contents are incubated for 30 minutes to allow the PB to bind the cryptosporidium analytes in a sandwich. The supernatant is discarded and the well is washed with PBS wash buffer leaving the sandwiches in the well. A 250 μL elution buffer containing 80 mM NaOAc (pH 9) with 95% formamide is added to the well and 90° C. heat is applied for minutes. This elutes the single-stranded electrochemically detectable oligonucleotide tags from the sandwiches and subsequently enables the tags to self-assemble into quadruplex electrochemically detectable oligonucleotide tags. The elution supernatant containing the tags is removed and transferred to a biosensor working electrode. The quadruplex electrochemically detectable oligonucleotide tags are allowed to adsorb for 10 minutes. A SWV scan is applied with a scan rate of 1400 mV/s. Other potentiostat settings include: scan increment of 5 mV, frequency of 280 Hz (0.0035/sec), pulse height of 20 mV, equilibrium time of 3 sec, initial E of −0.4 V, and final E of −1.2 V. A predetermined standard curve was prepared from known concentrations of tags. Positive and negative controls were used to adjust the concentration curve for antibody recovery from the sample. The net signal from the tags is measured as the tags signal associated with the analytes minus the negative control. The peak signal from around 0.47 V is used to convert the net peak signal to analyte concentration.

Example 2

Microbead Sandwich Assay with Electrochemically Detectable Oligonucleotide Tags

As a further example of an embodiment of this invention, test samples in Example 1 were found to have a high level of nonspecific materials that interfered with detection. The protocol in Table 9 was modified to add an additional step for magnetic separation to remove the nonspecific materials. In this example, reagents were procured in advance of the experiments including magnetic microparticles (MB) coated with anti-cryptosporidium antibodies to capture the analytes and a BSA blocking agent to block potential binding sites from non-specific materials. 1-micron polystyrene microparticles (PB) were conjugated with single-stranded electrochemically detectable oligonucleotide tags (20-mer PolyG), and also with anti-cryptosporidium antibodies using biotin-streptavidin chemistry. Other reagents and equipment included PBS wash buffer, 80 mM NaOAc (pH 9) with 95% formamide elution buffer, microtiter rotator, IMS separator, and microtiter with screen-printed carbon electrodes. A summary of the protocol is in Table 10.

TABLE 10

Protocol for Microbead Sandwich Assay with Electrochemically Detectable Oligonucleotide Tags

| Magnetic Separation | Tag Attachment | Tag Elution and Self Assembly | Tag Measurement and Analyte Concentration |
|---|---|---|---|
| Extract Analytes from Sample<br>1. Mix 500 μL sample with 500 μL PBS and 500,000 MB conjugated with capture antibodies for 30 min<br>2. Apply IMS then stand 3 min<br>3. Discard supernatant, wash with PBS, re-suspend | Attach Tags in Sandwiches<br>4. Mix re-suspended sample with 1 mL PBS and 2,000,000 PB conjugated with single-stranded oligonucleotide tags and antibodies | Elute Tags<br>7. Add 250 μL of 80 mM NaOAc (pH 9) with 95% formamide elution buffer and apply 90° C. heat for 10 min | Quantify Analytes<br>9. Adsorb tags in supernatant to biosensor<br>10. Apply SWV (1,400 mV/s)<br>11. Measure sample peak |

TABLE 10-continued

Protocol for Microbead Sandwich Assay
with Electrochemically Detectable Oligonucleotide Tags

| Magnetic Separation | Tag Attachment | Tag Elution and Self Assembly | Tag Measurement and Analyte Concentration |
|---|---|---|---|
| (to Step 4) | for 30 min<br>5. Apply IMS then stand 3 min<br>6. Discard supernatant, wash with PBS, re-suspend (to Step 7) | to enable self-assembly<br>8. Remove supernatant and transfer to biosensor (Step 9) | amplitude<br>12. Compare sample amplitude vs. concentration standards to determine concentration |

Figure 21B:
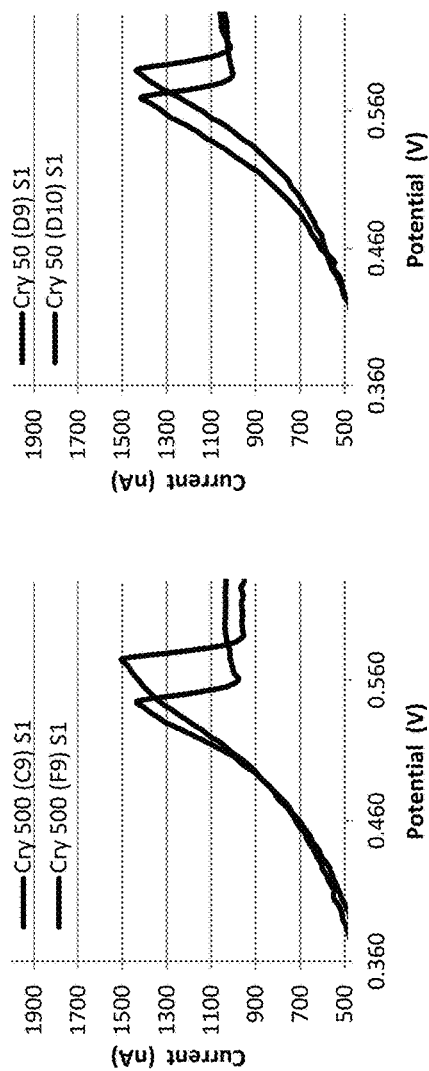
FIG. 21B contains peak signals from duplicate samples.

In this example, a 500 µL sample is placed in a 2 mL well or a tube along with 500,000 (5 µL) magnetic particles (MB) conjugated with anti-cryptosporidium antibodies and 500 µL PBS buffer. The contents are mixed for 30 minutes with a rotator using gentle agitation. The tube is placed in an IMS separator, inverted several times and allowed to stand for 3 minutes. The supernatant is discarded, and the magnetic bead-analyte complexes are washed with PBS. 500 µL wash buffer is added to re-suspend the magnetic bead-analyte complexes. Additional washes and a second magnetic bead step can also be applied to increase low yield of complexes. The re-suspended magnetic bead-analyte complexes are then combined with 2,000,000 (20 µL) polystyrene microbeads (PB) pre-conjugated with anti-cryptosporidium antibodies and single-stranded electrochemically detectable oligonucleotide tags, and 1 mL PBS wash buffer. The contents are mixed for 30 minutes with a rotator using gentle agitation. The tube is placed in an IMS separator, inverted several times and allowed to stand for 3 minutes. The supernatant is discarded, and the magnetic bead-analyte-polystyrene bead sandwiches are washed with PBS. PBS wash buffer is added to re-suspend the sandwiches. Additional washes and a second polystyrene bead step can also be applied to increase low yield of sandwiches. A 250 µL elution buffer containing 80 mM NaOAc (pH 9) with 95% formamide is added to the well and 90° C. heat is applied for 10 minutes. This elutes the single-stranded electrochemically detectable oligonucleotide tags from the sandwiches and subsequently enables the tags to self-assemble into quadruplex electrochemically detectable oligonucleotide tags. The elution supernatant containing the tags is removed and transferred to a biosensor working electrode. The quadruplex electrochemically detectable oligonucleotide tags are allowed to adsorb for 10 minutes. A SWV scan is applied with a scan rate of 1400 mV/s. Other potentiostat settings include: scan increment of 5 mV, frequency of 280 Hz (0.0035/sec), pulse height of 20 mV, equilibrium time of 3 sec, initial E of −0.4 V, and final E of −1.2 V. Referring to FIG. 21A, a predetermined standard curve was prepared from known concentrations of cryptosporidium. Positive and negative controls were used to adjust the concentration curve for antibody recovery from the sample. The peak signal from the scan is used to determine the analyte concentration from the corresponding signal on the concentration curve. Referring to FIG. 21B, samples were evaluated in duplicate and the average of the peak signals scans was measured against the concentration curve to determine the concentration of the samples.

Example 3

Multiplexing Microbead Sandwich Assay for Detecting Multiple Analytes in a Group In another example, an assay described in Example 2 is used to detect Cryptosporidium and *E. coli* O157:H7. There is provided a set of magnetic microparticles conjugated with antibodies that bind Cryptosporidium, and another set of magnetic microparticles conjugated with antibodies that bind *E. coli* O157:H7. There is also a set of polystyrene microparticles conjugated with antibodies that bind Cryptosporidium and millions of a unique guanine-rich oligonucleotide tag, and another set of polystyrene microparticles conjugated with antibodies that bind *E. coli* O157:H7 and millions of the same unique guanine-rich oligonucleotide tag. The protocol in Table 10 is used and all of the eluted tags are delivered to a common biosensor working electrode. The signal generated in Step 11 will exceed the negative control if a detectable concentration is present for Cryptosporidium, or *E. coli* O157:H7 or both pathogens.

Example 4

Multiplexing Microbead Assay for Detecting Multiple Analytes Individually

In another example, an assay described in Example 2 is used to detect Cryptosporidium and *E. coli* O157:H7. There is provided a set of magnetic microparticles conjugated with antibodies that bind Cryptosporidium, and another set of magnetic microparticles conjugated with antibodies that bind *E. coli* O157:H7. There is also a set of polystyrene microparticles conjugated with antibodies that bind Cryptosporidium and millions of a unique guanine-rich oligonucleotide tag, and another set of polystyrene microparticles conjugated with antibodies that bind *E. coli* O157:H7 and millions of a different unique guanine-rich oligonucleotide tag. Each oligonucleotide is designed to enable the single-stranded oligonucleotide to self assemble into quadruplexes. The protocol in Table 10 is used and all of the eluted tags are delivered to a well or chamber containing two different biosensor working electrodes. One working electrode is bound with a cytosine rich probe that is complementary with the Cryptosporidium oligonucleotide tags, and a second working electrode bound with a cytosine rich probe that is complementary with the *E. coli* oligonucleotide tags. Two separate signals are generated in Step 11, one associated with the Cryptosporidium working electrode and a second signal associate with the *E. coli* O157:H7 working electrode to measure the quantity of each analyte.

Example 5

Antimicrobial Susceptibility Test

In another example, an assay described in Example 2 is used to detect Extended spectrum β-lactamases (ESBL)-producing Enterobacteriaceae (EPE) such as E. coli producing CTX-M enzymes. In this example, urine samples are first exposed to Cefotaxime antibiotic and incubated for about 45 minutes at 35° C. to produce CTX-M enzymes if E. coli is present, viable and CTX-M producing. After the E. coli are lysed, a sandwich assay using the protocol in Table 10 applies a capture antibody on magnetic microparticles to magnetically extract CTX-M from non-specific materials, and a detection antibody on polystyrene microparticles to bind CTX-M with millions of oligonucleotide tags rich in electroactive guanine using the protocol in Table 10. Single-stranded oligonucleotide tags are eluted in a Na+ cationic buffer which causes the tags to self-assemble into quadruplexes that are adsorbed at the biosensor surface. When voltage is applied, guanine-quadruplexes produce 8-oxoguanine oxidation signals proportional to CTX-M concentration.

Example 6

Hybridization Assay

In another example, an assay described in Example 2 is used to detect 16S rRNA. There is provided a set of magnetic microparticles conjugated with DNA probes that hybridize with one end of the 16S rRNA target, and a set of polystyrene microparticles conjugated with DNA probes that hybridize with the other end of the 16S rRNA target and are also conjugated with millions of a unique guanine-rich oligonucleotide tag. The protocol in Table 10 is used to measure 8-oxoguanine oxidation signals proportional to analyte concentration. In another example, the protocol in Table 9 and Table 10 can be modified to improve the detection limit and reduce the incidence of non-specific binding that can negatively affect the clinical sensitivity and specificity. These can include one or more of increasing the contact time for attachment of antibodies or DNA probes to analytes, applying a 2-stage process for magnetic separation (i.e. apply a second magnetic separation to extract targets in the wash), reduce the size of the magnetic particles to sub-micron diameter, increase or decrease the number of magnetic microparticles and polystyrene microparticles, apply a 2-stage process for tag attachment (i.e. apply a second batch of polystyrene microparticles to the re-suspended tag attachment solution and repeat the tag attachment protocol), add more washes to remove non-specific materials and unattached tags, change the antibodies or DNA probes, replace a single ligand with a cocktail of multiple ligands, extend the DNA probes with longer linkers, change the elution buffer with a different Na+ or K+ cation solution, and change the oligonucleotide tag (longer, more guanine, different sequence).

What is claimed is:

1. A conjugate for detecting and/or quantifying an analyte in a fluid sample, wherein said conjugate comprises one or more ligands and a plurality of quadruplex electrochemically detectable oligonucleotide tags, wherein said quadruplex electrochemically detectable oligonucleotide tag comprises at least 4 guanine in a square tetrad structure, and said conjugate is configured to produce an 8-oxoguanine signal when subjected to an electrochemical detection technique.

2. A method for detecting and/or quantifying an analyte in a fluid sample comprising:
   (a) providing a fluid sample that may contain non-specific materials and an analyte;
   (b) providing a plurality of electrochemically detectable oligonucleotide tags that are quadruplexes or single-stranded, and said tags bind to the analyte directly, or indirectly using one or more ligands and particles;
   (c) unbinding said electrochemically detectable oligonucleotide tags from said analyte, or ligands and particles;
   (d) optionally exposing electrochemically detectable oligonucleotide tags that are single-stranded to monovalent cations that enable said tags to self assemble into quadruplexes;
   (e) providing a biosensor working electrode and adsorbing or hybridizing said electrochemically detectable oligonucleotide tags to said biosensor working electrode; and
   (f) providing an electrochemical detection technique that produces a peak electrochemical signal on the biosensor working electrode in proportion to the quantity of said analyte;
   wherein said quadruplex electrochemically detectable oligonucleotide tag comprises at least 4 guanine in a square tetrad structure, and said electrochemical detection technique produces an 8-oxoguanine signal.

3. The method of claim 2, wherein the electrochemical detection technique in step (f) further comprises:
   (g) said analyte is determined to be present when the peak electrochemical signal in step (f) exceeds a cut-off signal; and
   (h) the quantity of said analyte is determined by comparing the generated peak electrochemical signal in step (f) with predetermined signals from known quantities of said analyte.

4. The method of claim 2, wherein the method further comprises after step (a) the fluid sample is treated with one or more of a membrane, a chemical, and a disaggregation technique.

5. The method of claim 2, wherein the method further comprises replacing step (b) with:
   (b1) (i) providing magnetic particles conjugated with a first ligand to create magnetic particle-analyte complexes, and (ii) providing nonmagnetic particles conjugated with a second ligand and a plurality of electrochemically detectable oligonucleotide tags in greater amounts than the bound analyte to create magnetic particle-analyte-nonmagnetic particle sandwiches, wherein the electrochemically detectable oligonucleotide tags are quadruplexes or single-stranded.

6. The method of claim 2, wherein the method further comprises after step (b):
   (b2) providing a well pre-coated with ligands to capture analyte-tag complexes in a modified direct enzyme-linked immunosorbent assay, an indirect enzyme-linked immunosorbent assay, a sandwich enzyme linked immunosorbent assay, or a competitive enzyme linked immunosorbent assay.

7. The method of claim 2, wherein the method further comprises repeating steps (a) to (f) with one or more samples to produce a cumulative peak electrochemical signal.

8. The method of claim 2, wherein the ligand is selected from the group consisting of antibodies, monoclonal antibodies, polyclonal antibodies, amino acids, peptides, proteins, haptens, nucleic acids, oligonucleotides, DNA, RNA, aptamers, matched pairs thereof and combinations thereof, and the analyte is selected from the group consisting of cells, bacteria, protozoa, fungi, virus particles, proteins, peptides, enzymes, hormones, haptens, cancer markers, nucleic acids, genes, oligonucleotides, DNA, RNA, small molecules, drugs, pesticides, organic chemicals, industrial chemicals and compounds, and combinations thereof.

9. A device for detecting and/or quantifying an analyte in a fluid sample comprising consumable reagents and an instrument for processing the fluid sample and consumable reagents, wherein said device comprises:
(a) a tag attachment unit comprising a plurality of electrochemically detectable oligonucleotide tags that are quadruplexes or single-stranded, and said tags bind to the analyte directly, or indirectly using one or more ligands and particles;
(b) a tag discharge unit for unbinding said electrochemically detectable oligonucleotide tags from said analyte, or ligands and particles;
(c) optionally, a tag self-assembly unit for exposing electrochemically detectable oligonucleotide tags that are single-stranded to monovalent cations that enable said tags to self assemble into quadruplexes; and
(d) an electrochemical detection unit comprising a biosensor working electrode for adsorbing or hybridizing said quadruplexes to said biosensor working electrode, and for providing an electrochemical detection technique that produces a peak electrochemical signal on the biosensor working electrode in proportion to the quantity of said analyte and produces an 8-oxoguanine signal;
wherein said quadruplex electrochemically detectable oligonucleotide tag comprises at least 4 guanine in a square tetrad structure and are configured to produce an 8-oxoguanine signal when subjected to an electrochemical detection technique, and said electrochemical detection unit is configured to detect an 8-oxoguanine signal.

10. The device of claim 9, wherein:
(a) the consumable reagents are provided in one or more consumable test cartridges; and
(b) the instrument for processing the fluid sample and consumable reagents is a portable analyzer.

11. The device of claim 9, wherein:
(a) the consumable reagents are provided in one or more consumable high throughput test panels; and
(b) the instrument for processing the fluid sample and consumable reagents is a high throughput analyzer.

12. The device of claim 9, wherein:
(a) the consumable reagents are provided in one or more consumable test cartridges or consumable high throughput test panels; and
(b) the instrument for processing the fluid sample and consumable reagents comprises one or more of an autonomous networked analyzer, a sample collection unit, a sample concentration unit, and a communications unit.

13. The device of claim 10, 11, or 12, wherein the consumable test cartridges and/or the consumable high throughput panels comprises one or more of microfluidics, a specimen inlet, reservoirs containing reagents, channels and mixing chambers, biosensors or nanobiosensors, heaters, valves, inlets for air connections, electrical connectors and circuitry for signal measurements and electrical systems, bar code, and Quick Response (QR) code.

14. The device of claim 9, wherein the device is integrated with an associated instrument for the automated delivery of drugs or chemicals, and said device measures the analyte presence and/or quantity which triggers the release of drugs or chemicals.

15. The electrochemically detectable oligonucleotide tag of claim 1, and/or the method of claim 2, and/or the device of claim 9, wherein the electrochemically detectable oligonucleotide tag is a quadruplex that (a) does not comprise at least 4 guanine in a tetrad structure but instead comprises at least 4 adenine in a tetrad structure, and an electrochemical detection technique produces 8-oxoadenine signals, or (b) does not comprise at least 4 guanine in a tetrad structure but instead comprises at least 4 thymine in a tetrad structure, and an electrochemical detection technique produces 8-oxothymine signals, or (c) does not comprise at least 4 guanine in a tetrad structure but instead comprises at least 4 cytosine in a tetrad structure, and an electrochemical detection technique produces 6-oxocytosine signals, or (d) comprises one or more quadruplex tetrads formed on different segments of the same electrochemically detectable oligonucleotide tag and an electrochemical technique produces multiple signals from the oxidation of one or more different oxo derivatives and/or nucleotides.

16. The electrochemically detectable oligonucleotide tag of claim 1, and/or the method of claim 2, and/or the device of claim 9, wherein the electrochemically detectable oligonucleotide tag can change in shape, structure, and/or performance by modifying one or more of the number of guanine per tag, the number of nucleotides per tag, the sequence of the nucleotides, the cation molecule, the cation concentration, the temperature during tag self-assembly, the pH during tag self-assembly, the presence of chemicals during tag self-assembly, and the use of mechanical agitation during tag self-assembly.

17. The method of claim 2, wherein multiple different analytes can be detected and/or quantified in a fluid sample:
(i) as multiple different analytes measured individually at unique biosensor working electrodes associated with each different analyte by replacing (a), (b) and
(e) with (a1), (b1) and (e1) wherein:
(a1) providing a fluid sample that may contain non-specific materials and an analyte or multiple different analytes;
(b1) providing one or more sets of particles conjugated with a ligand for binding one individual analyte and a plurality of individual electrochemically detectable oligonucleotide tags associated with said individual analyte, wherein each individual electrochemically detectable oligonucleotide tag comprises a first nucleotide sequence that is or self assembles into a quadruplex, and a second nucleotide sequence that is distinctive from electrochemically detectable oligonucleotide tags used for other individual analytes;
(e1) providing one or more individual biosensor working electrodes conjugated with a plurality of an oligonucleotide probe that is complementary to the second nucleotide sequence of said individual electrochemically detectable oligonucleotide tag associated with said individual analyte, and hybridizing said individual electrochemically detectable oligonucleotide tags to said individual biosensor working electrode associated with said individual analyte;
or
(ii) as multiple different analytes measured as a group at a common biosensor working electrode associated with any analyte in said group of multiple different analytes by replacing (a), (b) and (e) with (a2), (b2) and (e2) wherein:

(a2) providing a fluid sample that may contain non-specific materials and an analyte or multiple different analytes;

(b2) providing one or more sets of particles conjugated with one or more ligands for binding one or more analytes in said group and a plurality of common electrochemically detectable oligonucleotide tags associated with any analyte in said group, wherein each common electrochemically detectable oligonucleotide tag comprises a first nucleotide sequence that is or self assembles into a quadruplex, and a second nucleotide sequence that is distinctive from electrochemically detectable oligonucleotide tags used for other groups;

(e2) providing one or more common biosensor working electrodes conjugated with a plurality of an oligonucleotide probe that is complementary to the second nucleotide sequence of said common electrochemically detectable oligonucleotide tag associated with one or more analytes in said group, and hybridizing said common electrochemically detectable oligonucleotide tags to said common biosensor working electrode associated with one or more analytes in said group.

18. The device of claim 9, wherein multiple different analytes can be detected and/or quantified in a fluid sample:

(i) as multiple different analytes measured individually at unique biosensor working electrodes associated with each different analyte by replacing (a) and (d) with (a1) and (d1) wherein:

(a1) a tag attachment unit for providing one or more sets of particles conjugated with a ligand for binding one individual analyte and a plurality of individual electrochemically detectable oligonucleotide tags associated with said individual analyte, wherein each individual electrochemically detectable oligonucleotide tag comprises a first nucleotide sequence that is or self assembles into a quadruplex, and a second nucleotide sequence that is distinctive from electrochemically detectable oligonucleotide tags used for other individual analytes;

(d1) an electrochemical detection unit for providing one or more individual biosensor working electrodes conjugated with a plurality of an oligonucleotide probe that is complementary to the second nucleotide sequence of said individual electrochemically detectable oligonucleotide tag associated with said individual analyte, and hybridizing said individual electrochemically detectable oligonucleotide tags to said individual biosensor working electrode associated with said individual analyte, and for providing an electrochemical detection technique that produces a peak electrochemical signal on each biosensor working electrode in proportion to the quantity of said individual analyte; or (ii) as multiple different analytes measured as a group at a common biosensor working electrode associated with any analyte in said group of multiple different analytes by replacing (a) and (d) with (a2) and (d2) wherein:

(a2) a tag attachment unit for providing one or more sets of particles conjugated with one or more ligands for binding one or more analytes in said group and a plurality of common electrochemically detectable oligonucleotide tags associated with any analyte in said group, wherein each common electrochemically detectable oligonucleotide tag comprises a first nucleotide sequence that is or self assembles into a quadruplex, and a second nucleotide sequence that is distinctive from electrochemically detectable oligonucleotide tags used for other groups;

(d2) an electrochemical detection unit for providing one or more common biosensor working electrodes conjugated with a plurality of an oligonucleotide probe that is complementary to the second nucleotide sequence of said common electrochemically detectable oligonucleotide tag associated with one or more analytes in said group, and hybridizing said common electrochemically detectable oligonucleotide tags to said common biosensor working electrode associated with one or more analytes in said group.

19. The device of claim 9, wherein the electrochemical detection unit comprising (a) an electrochemical biosensor or nanobiosensor comprising one or more working electrodes, wherein each working electrode is associated with an individual analyte or group of multiple different analytes and wherein each working electrode is uncoated or is conjugated with a plurality of an oligonucleotide probe to adsorb or hybridize associated quadruplex electrochemically detectable oligonucleotide tags that are complementary to the oligonucleotide probes, and (b) an electrochemical detection system that produces electrochemical signals on each working electrode in proportion to the level of an associated analyte or group of multiple different analytes.

* * * * *